US010858653B2

(12) United States Patent
Olayioye et al.

(10) Patent No.: US 10,858,653 B2
(45) Date of Patent: Dec. 8, 2020

(54) MAMMALIAN CELLS FOR PRODUCING A SECRETED PROTEIN

(71) Applicant: Boehringer Ingelheim International GmbH, Ingelheim am Rhein (DE)

(72) Inventors: Monilola Olayioye, Ulm (DE); Angelika Hausser, Stuttgart (DE); Lisa Pieper, Biberach an der Riss (DE); Michaela Strotbek, Asperg (DE); Till Wenger, Ulm (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/083,982

(22) PCT Filed: Feb. 10, 2017

(86) PCT No.: PCT/EP2017/053043
§ 371 (c)(1),
(2) Date: Sep. 11, 2018

(87) PCT Pub. No.: WO2017/157593
PCT Pub. Date: Sep. 21, 2017

(65) Prior Publication Data
US 2020/0165605 A1    May 28, 2020

(30) Foreign Application Priority Data
Mar. 18, 2016 (EP) ..................... 16161253

(51) Int. Cl.
C12N 15/85 (2006.01)
C12N 15/113 (2010.01)
C07K 14/47 (2006.01)
C07K 16/00 (2006.01)
C12N 9/10 (2006.01)
C12N 9/22 (2006.01)
C12N 15/11 (2006.01)

(52) U.S. Cl.
CPC ........ *C12N 15/113* (2013.01); *C07K 14/4705* (2013.01); *C07K 16/00* (2013.01); *C12N 9/1088* (2013.01); *C12N 9/22* (2013.01); *C12N 15/11* (2013.01); *C12N 15/1137* (2013.01); *C12Y 205/01018* (2013.01); *C07K 2319/00* (2013.01); *C12N 2310/122* (2013.01); *C12N 2310/14* (2013.01); *C12N 2310/20* (2017.05); *C12N 2310/531* (2013.01); *C12N 2510/02* (2013.01); *C12N 2800/80* (2013.01)

(58) Field of Classification Search
CPC ..................... C12N 15/111; C12N 2510/02
See application file for complete search history.

(56) References Cited

FOREIGN PATENT DOCUMENTS

WO    2009062789    5/2009
WO    2013182553    12/2013

OTHER PUBLICATIONS

Strotbek et al. Metabolic Engineering (2013), vol. 20, 157-166. (Year: 2013).*
Florin, Lore et al. "Heterologous expression of the lipid transfer protein CERT increases therapeutic protein productivity of mammalian cells" (2009) Journal of Biotechnology, 141, 84-90.
Grosch, Sabine et al. "Chain length-specific properties of ceramides" (2012) Progress in Lipid Research, 51, 50-62.
Hanada, Kentaro et al. "Molecular machinery for non-vesicular trafficking of ceramide" (2003) Nature, vol. 426, 803-809.
Hausser, Angelika et al. "Protein kinase D regulates vesicular transport by phosphorylation and activation of phosphatidylinositol-4 kinase III ß at the Golgi complex" (2005) Nat Cell Biol., 7(9): 880-886.
International Search Report for PCT/EP2017/053043 filed Feb. 10, 2017.
Nishimiya, Daisuke et al. "Overexpression of CHOP alone and in combination with chaperones is effective in improving antibody production in mammalian cells" (2013) Appl Microbiol Biotechnol, 97: 2531-2539.
Ohya, Tomoshi et al. "Improved Production of Recombinant Human Antithrombin III in Chinese Hamster Ovary Cells by ATF4 Overexpression" (2008) Biotechnology and Bioengineering, vol. 100, No. 2, 317-324.
Romero, Nahuel et al. "Rab1b overexpression modifies Golgi size and gene expression in HeLa cells and modulates the thyrotrophin response in thyroid cells in culture" (2013) Molecular Biology of the Cell, vol. 24, 617-632.
Thuerauf, Donna J. et al. "Effects of the Isoform-specific Characteristics of ATF6a and ATF6ß on Endoplasmic Reticulum Stress Response Gene Expression and Cell Viability" (2007) The Journal of Biological Chemistry, vol. 282, No. 31, 22865-22878.
Thuerauf, Donna J. et al. "Opposing Roles for ATFßa and ATF6ß in Endoplasmic Reticulum Stress Response Gene Induction" (2004) The Journal of Biological Chemistry, vol. 279, No. 20, 21078-21084.

(Continued)

*Primary Examiner* — J. E Angell
(74) *Attorney, Agent, or Firm* — Atabak R. Royaee

(57) ABSTRACT

The invention relates to the field of cell culture technology. It concerns the knockdown, using RNA interference, or gene knockout, of activating transcription factor 6 beta (ATF6B), or the combination of ceramide synthase 2 (CERS2) and TBC1 domain family member 20 (TBC1 D20) proteins, which play central roles in the cellular secretion pathway. This downregulation leads to improved secretion of biopharmaceutically relevant products produced in mammalian cells. The invention specifically relates to mammalian cells having enhanced secretion of a recombinant therapeutic protein compared to a control cell, a method of producing said mammalian cell, a method for the production of a recombinant secreted therapeutic protein and the use of said mammalian cell for increasing the yield of a recombinant secreted therapeutic protein.

6 Claims, 20 Drawing Sheets
Specification includes a Sequence Listing.

(56) References Cited

OTHER PUBLICATIONS

Tigges, Marcel et al. "Xbpl-based engineering of secretory capacity enhances the productivity of Chinese hamster ovary cells" (2006) Metabolic Engineering, 8: 264-272.

Yamamoto, Keisuke et al. "Transcriptional Induction of Mammalian ER Quality Control Proteins is Mediated by Single or Combined Action of ATF6a and XBP1" (2007) Developmental Cell, 13, 365-376.

* cited by examiner

| miRNA screen hit | NGS hit RefSeq | NGS hit Locus | Gene symbol | Gene description | normalized fold change gene expression (\|log2\|) |
|---|---|---|---|---|---|
| hsa-miR-1287 SEQ ID NO:32 | XM_003508493.1 | NW_003614548 | Atf6b | activating transcription factor 6 beta | 2,16 (1.11) |
| hsa-miR-1978 SEQ ID NO:33 | XM_003498655.1 | NW_003613699 | Cers2 | ceramide synthase 2 | 2,54 (1.34) |
| | XM_003511491.1 | NW_006879419 | Tbc1d20 | TBC1 domain family, member 20 | 2,28 (1.19) |

FIG. 1A

| siRNA | Sequence | SEQ ID NO |
|---|---|---|
| siAtf6b#1 | CCUCCUCAGGUUCAGUUCA | SEQ ID NO: 9 |
| siAtf6b#2 | GCAGCGAAUGAUCAAGAAC | SEQ ID NO: 10 |
| siAtf6b#3 | AGACACCUUCUAUGUUGUC | SEQ ID NO: 11 |
| siTbc1D20#1 | AGAACUAAUCGACAUUAUC | SEQ ID NO: 7 |
| siCerS2#1 | AGAGUCGGCUCCUAUCUAA | SEQ ID NO: 8 |
| shRNA | Antisense target site | |
| shAtf6b#1 | UCCAUCUUCACACUGAGGACC | SEQ ID NO: 15 |
| shTbc1D20#1 | AAUCCUUGCUCAACUGUCGAA | SEQ ID NO: 12 |
| shCerS2#1 | UUAAGUUCACAGGCAGCCAUA | SEQ ID NO: 13 |
| shCerS2#2 | UGAUGUAGAGGUCUGAGGCUU | SEQ ID NO: 14 |

FIG. 1B

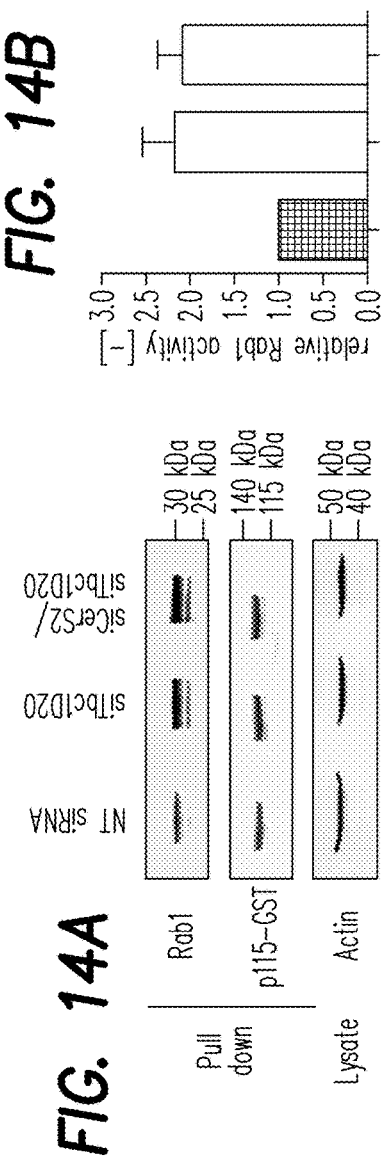
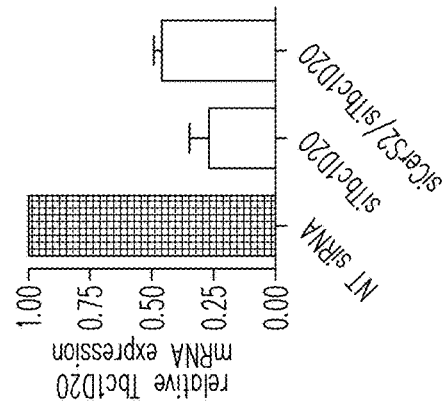
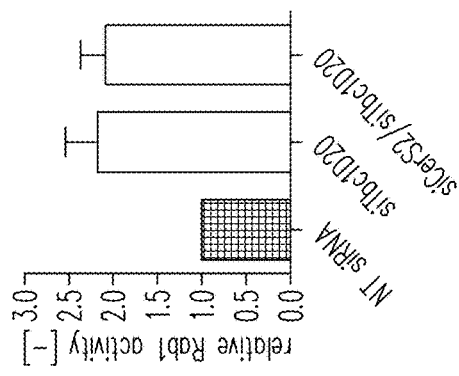
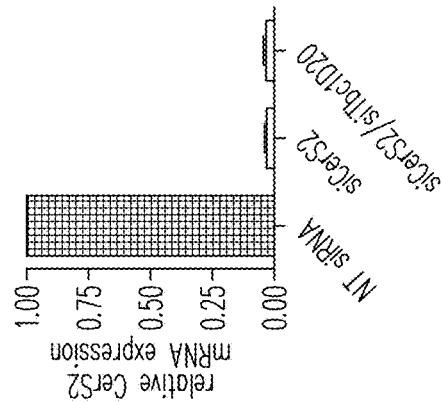
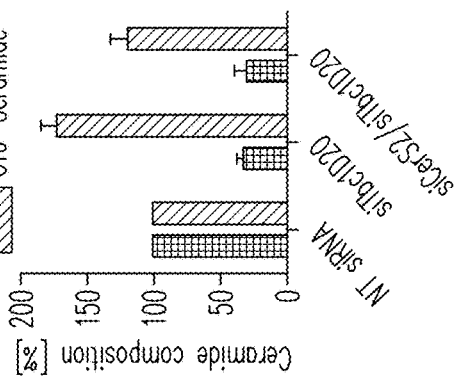
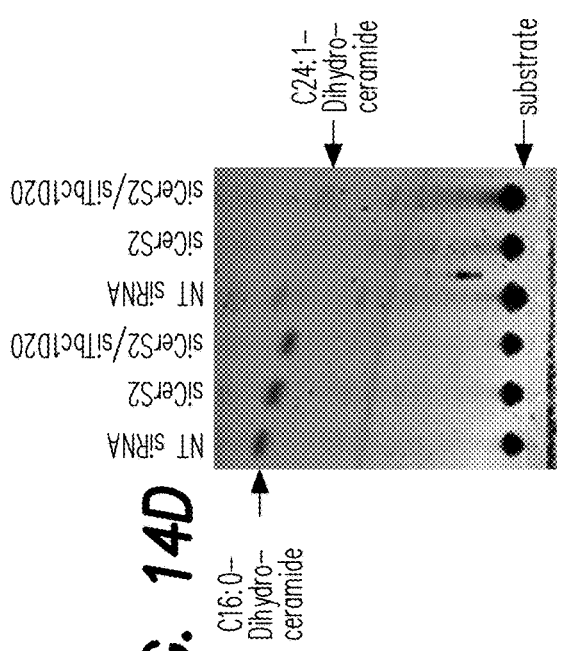

SEQUENCE LISTING

<160> NUMBER OF SEQ ID NOS: 53

<210> SEQ ID NO 1
<211> LENGTH: 3330
<212> TYPE: DNA
<213> ORGANISM: Cricetulus griseus
<220> FEATURE:
<223> OTHER INFORMATION: Tbc1d20 cDNA

<400> SEQUENCE: 1

| | | | | | | |
|---|---|---|---|---|---|---|
| cgcgcctgcg | cgtcgcaggc | cgacagagac | cagcctgtcc | cggccgcagt | ggggttacac | 60 |
| ccgcggtgga | agccgcgtct | caggctccgc | cgccagccgg | ggctcgggct | ggggcccggg | 120 |
| cccccgggga | tggccctccg | gccctcacag | ggcgacggct | ccgcgggccg | ctggaactgt | 180 |
| ggcttgggaa | aggcagactt | taatgccaaa | aggaaaaaga | aggtggcgga | aatacaccag | 240 |
| gccctgaaca | gtgatcccac | cgacgtggct | gcccttcgac | gaatggcgat | cagtgaggga | 300 |
| gggctcctga | ctgatgagat | caggtgccag | gtgtggccca | agctcctcaa | tgtcaacacc | 360 |
| tgtgagccac | cgcctgtgtc | aaggaaggat | cttcgacagt | tgagcaagga | ttaccagcaa | 420 |
| gtactgctgg | atgtcaggcg | gtctcttcgg | cgcttccctc | ctggcatgcc | agatgagcag | 480 |
| agagaagggc | ttcaggaaga | actaatcgac | attatcctcc | tcatcttgga | tcgcaaccct | 540 |
| cagctccact | actaccaggg | ctaccatgac | atcgtggtca | cctttctgct | ggtggtgggc | 600 |
| gagaggctgg | caacatcctt | ggtagaaaaa | ttatctaccc | atcacctcag | ggatttcatg | 660 |
| gatcccacaa | tggacaatac | caagcacatt | ctaaattatc | tgatgcccat | cattgaccaa | 720 |
| gtgaacccag | aactccatga | cttcatgcag | agtgctgagg | tggggaccat | ctttgccctc | 780 |
| agctggctta | tcacctggtt | tgggcacgtc | ctgtcagact | tcaggcacgt | tgtgcggtta | 840 |
| tacgacttct | tcctggcctg | ccacccactc | atgcccattt | actttgcagc | tgtgattgtg | 900 |
| ctgtaccggg | agcaggaagt | cctggactgt | gactgtgaca | tggcctctgt | ccaccacctg | 960 |
| ttgtctcaga | tccctcagga | cctgccctat | gagacgctca | tcagcagagc | aggagacctc | 1020 |
| tttgttcagt | tcccccttc | tgaacttgca | agggaggcag | ctgcacagca | agaggctgaa | 1080 |
| agaacggcag | cctctacttt | caaagacttt | gagctggcat | cagcccagca | gaggccagat | 1140 |
| atggtgctgc | ggcagcggtt | tcggggactt | ctgcggcctg | agactcgaac | aaaagatgtc | 1200 |
| ctgaccaaac | caaggaccaa | ccgctttgtg | aaactggcag | tgatggggct | aacggtggca | 1260 |
| cttggagcag | cagcactagc | agtggtgaag | agtgccctgg | agtgggcccc | taagttccag | 1320 |
| ctgcagctgt | tccctgaac | tcagccccag | gagccacttc | cgtacccagt | gcaccaagct | 1380 |
| ctccccattc | ccagaaaggc | actagagggt | gggattgctg | tcattaaagg | gttcctgtca | 1440 |
| ggggtgttct | gttctgccac | ccttggcagc | ttgtcttttg | gctttgtggc | taatggcaac | 1500 |
| actgcctgac | actgggttta | gtggaccctga | gtgctctgtg | ctcctcaact | gctgcaagtg | 1560 |
| gctgtggtgc | ccctggctac | ccaattcact | gcctagaaga | aagttgggcc | cgaagatgcc | 1620 |
| ctccttaccg | caccacgtgt | cctgcatctc | ctagacaaag | caggcaggag | ctgccaacaa | 1680 |
| agtctagcct | tgggatgaaa | gcgaggggag | aggactgtag | cttgggggcc | agttggttag | 1740 |
| agacaggcat | gagctgggtt | ctagttaaat | tttatgatcc | cagcctagag | atcacttgca | 1800 |
| gaggaatgtt | aacccccctg | aacggtgttg | cctgtgtctc | cctatttctc | tacaagccac | 1860 |
| atgacattac | ctataaagac | attttttaata | ctatttttat | gattgtatac | tacaccaaac | 1920 |
| atagcgagta | ttctcactta | agaaaaatga | cttatatatg | tatgcaggtg | tccacagagg | 1980 |
| ccagaagtgg | acttgagatt | tcatggagcc | tggtgtgggt | gctggtatct | gagtgctggt | 2040 |

```
cctctactaa agctcaagca ggaagtgctc tcaactgttg agccatctct ccggcctcct   2100
cactcacaca gttccttcat ggagaagcta tcagtgatga gcttatattg gcctgacatt   2160
tgtttccttt tttggagggg aatagaaccc agggccttgt acatgtgagg caagtgttct   2220
accactgagt agtaccaaac ttttagtag tttttatttt tgagacaggg tctatttaag   2280
ttacccaggc tagccttgaa cttttgatcc tcctgcctca gctcccgatt atctgggagg   2340
acagggttgc acctgagata tattccctgc tcagtttagc caaagttgct ttgtgaacag   2400
ccccacgccc cagtgtcgcc cccatctcac tttctgattt cccactcatc acccacttgg   2460
cctgtgtatt gatctcctca gctgctggtc tcaggctggg aatgtccttg gaaacttgcc   2520
agcatgtaga caggttttgg caggaatccc ataccaccag cctcgcttac ccctgggctc   2580
ctccaggagg gcacatggga tccatgggat cactcggtct tcctaggatg ctttgttaa    2640 aagcaaggcc aggtttgttt tgaagagact ctggcttgaa acaaaagtg ccttttgctg    2700 ctctaaagag tgtatagtag gaagcatctg catgcctcca tctcctgatc attcctgggc   2760
actcttctcc agtcatacca gtccagacc cagtgtgtcc ctgtgcccgc cgcatgccgt    2820
ggacactctg tgtgctgggc agccacaagc cagagcacat agaaggtgtc caggctgaat   2880
cacacaaagc actttaacca aatcaagctg gagtggttaa gtcattctcc acacaggagc   2940
cctgcctaga gtgagtgatt cacagggatt agttcaggac aaaggaggat tttccaggat   3000
ccagagtgat aaggtgacaa atactgttta gtctcccaca ggagcttgtc atctgtacct   3060
ctagcaagca tacttgaaga gctgtaggaa gtgtgctggc tgaggggagg ggcatgggcc   3120
cagggtccaa gccacaattc tgcatccaaa caagcaggtg gcactggctt gtgctgagct   3180
gaagagtggt gtgtgcccat accaggactc ccctgctact aagaagcgtt gtcaatttac   3240
cttcaggtac ttacttaact ctgtaaagat atgtgtagat gttttgtaca gagccctgta   3300
tgaaataaac acccttatgt ggttcctaat                                    3330
```

<210> SEQ ID NO 2
<211> LENGTH: 1305
<212> TYPE: DNA
<213> ORGANISM: Cricetulus griseus
<220> FEATURE:
<223> OTHER INFORMATION: CerS2 cDNA

<400> SEQUENCE: 2

```
gcgtggccag ctctgggagc agcagctggt gaaactagct ttacgggcgg gcggtaactt     60
gctaattact ggctcagagg ccctcgagct agcttgctcc ctgcaggatg ctgcagacct    120
tgtatgacca cttctggtgg gaccgactat ggctgcctgt gaacttaacc tgggctgatc    180
tagaagacag agatggacgt gtctatgcca aagcctcaga cctctacatc acacttcccc    240
tggccttggt cttccttgtc attcgatact tctttgagct ttatgtggct acacccctgg    300 ctgcccctcct gaatgttaag gagaaaaccc gactacgagc acctcccaat gtcaccttag    360
aacatttcta cctgaccaac ggcaagcagc ccaagcaggt ggaggttgag cttttgtctc    420
ggcagagtgg gctctctggc cgccagatag aacgctggtt ccgccgccgc cgcaaccagg    480
acaggcccag ccttctcaag aagttccgag aagccagttg gagattcaca ttttacctga    540
ttgcctttgt tgcgggcatg gctgtcattg tggataaacc ctggttctat gacttgagga    600
aagtttggga gggctatccc atacagagca tcgtcccttc tcagtattgg tactacatga    660
ttgaactctc cttctactgg tccctgctct tcagcattgc ttctgatgtc aagcgaaagg    720
attttaagga acagatcatc caccacgtgg ccaccatcat tctcctcagc ttctcctggt    780
```

```
ttgccaatta tgtccgagca gggactctca tcatggctct gcatgactct tctgactacc    840
tgctggagtc cgccaagatg tttaactacg cgggatggaa aaacacctgc aataacatct    900
tcattgtctt cgccatcgtt ttcatcatta ctcgactggt tatcatgcct ttctggatcc    960
tacactgcac gctggtatac ccactggagc tctaccctgc cttctttggc tattacttct   1020
tcaacatcat gatggcagtg ctacagatgc tgcatatctt ctgggcctac ttcattttgc   1080
gcatggccca aagttcata actggaaagc tggtagaaga tgaacgcagt gaccgagaag    1140
aaacagagag ctcagagggg gaggaggctg cagctgggc aggagcaaag agtcggctcc    1200
tatctaatgg ccaccccatc ctcaataaca atcatcctaa gaatgactga accattgtcc   1260
tagctgcctc ccacattaat acacgaagcc aagaaactag ccaac                   1305
```

<210> SEQ ID NO 3
<211> LENGTH: 2172
<212> TYPE: DNA
<213> ORGANISM: Cricetulus griseus
<220> FEATURE:
<223> OTHER INFORMATION: Atf6b cDNA

<400> SEQUENCE: 3

```
cacaggttcc tggagtaggg gaggtcctca gtgtgaagat ggagtcctta gcacctccac     60
tctgcctgct gggagacgat ccagcatccc catttgaaac ggtccaaatc accgtgggtt    120
ctgtcgctga tgacccctca gatatccaga ccaaggtaga acccgcctct ccatcttctt    180
ctgtcaactc cgaggcctcc ctgctctcag cagactctcc cagccaggct tttataggag    240
aggaggttct ggaagtgaag acggagtccc catctcctcc ggggtgcctc ctgtgggatg    300
tcccagctcc ttcacttgga gctgtccaga tcagcatggg cccatcacct gttagttcct    360
cagggaaagc tccagccact cggaagcctc cactgcagcc caagcctgtg gtgctaacca    420
cagttcaggt gccacctaga gctgggcctc ccagcactac tgtccttttg cagccctcg    480 tccagcagcc cgcagtgtcc ccagttgtcc tcatccaagg tgctattcga gtccagcctg    540
aagggccagc ccctgcagtt ccacggcccg aaaggaagag cattgtccct gctcctctgc    600
ctgggaactc ctgccctcct gaagtggacg caaagctgct gaagcgtcag cagcgaatga    660
tcaagaacag agagtcggcc tgccagtccc gccggaagaa gaaagagtat ctgcagggac    720
tggaggccag actgcaggct gtgctggcag acaaccagca actgcgcagg gagaatgctg    780
ccctccggcg gcggctggag accctgctga cagagaacag tgagctcaag ctgggctctg    840
ggaacaggaa agttgtctgc atcatggtct tccttctctt cattgccttc aactttggac    900
ctgtgagcat tagtgagcca cctccagctc ccatctctcc tcggatgagc agggaggaag    960
ctcgacccag gagacacctg ctggagttct ccgagcaggg gccagctcat ggtgttgaac   1020
ccctccagaa agctgcccgg ggcccagagg agcggcagcc cagccctgca ggcaggccca   1080
gcttcagaaa cctgacagcc ttccctggcg gggccaagga gctgctgctg agagacctgg   1140
accagctctt cctcgcctct gactgccgcc acttcaaccg cacggagtcc ctgaggcttg   1200
ctgatgagct gagtggctgg gtgcagcgtc accagagagg tcgacggagg atgcctcaca   1260
gggcccagga gagacagaag tctcagctac ggaagaagtc accgccagtg aaaccagtcc   1320
ccacccaacc tccaggacct cctgagaggg accctgtggg gcagctgcag ctctaccgcc   1380
acccaggccg ttcgcagcct gagtttctag atgcaatcga ccggcgggaa gacaccttct   1440
atgttgtctc cttccgaagg gaccacttgc tgctcccggc catcagccac aacaagacgt   1500
ccagacccaa gatgtcccctg gtgatgccag ccatggcccc caatgagacc gtgtcaggcc   1560
```

```
gggggccccc agggggactat gaggagatga tgcagatcga gtgtgaggtc atggacacca    1620
gggtgattca catcaagacc tccacggtgc cccctcact ccggaagcag ccatccccaa     1680
ccccaggcaa taccacaggt ggccccctgc cagcttctgc agccagtcag gccagtcagg    1740
cctcccacca gccctctac ctcaaccacc cctgacctct gcagctcacg ttggcttaga     1800
actggtttgg gggagcctgg tccttgaact tgggggtaat tggtaaagga aagcagggtg    1860
tatgggatcc agcacttaat gggagtaggg tgggtggctc acctctcctt acctcttcag    1920
aatatagggc tcctctcctt cctgcaaacc cccaggcccc ctctttctct gagagaacct    1980
cctcaggttc agttcaggt gggtagcttc ccatagcctc tttgttcttt ggtttatcta     2040
ttcaggagta gaggtgggac tttggtcccc aggtgggaca agagatgctc ttgggtggtg    2100
gaagtcagtc tgtgtgtgta ttatctttt tattattact aaataaataa cccagaggga     2160
gctaaaggaa tg                                                         2172
```

<210> SEQ ID NO 4
<211> LENGTH: 402
<212> TYPE: PRT
<213> ORGANISM: Cricetulus griseus
<220> FEATURE:
<223> OTHER INFORMATION: TBC1D20

<400> SEQUENCE: 4

```
Met Ala Leu Arg Pro Ser Gln Gly Asp Gly Ser Ala Gly Arg Trp Asn
1               5                   10                  15

Cys Gly Leu Gly Lys Ala Asp Phe Asn Ala Lys Arg Lys Lys Lys Val
            20                  25                  30

Ala Glu Ile His Gln Ala Leu Asn Ser Asp Pro Thr Asp Val Ala Ala
        35                  40                  45

Leu Arg Arg Met Ala Ile Ser Glu Gly Gly Leu Leu Thr Asp Glu Ile
    50                  55                  60

Arg Cys Gln Val Trp Pro Lys Leu Leu Asn Val Asn Thr Cys Glu Pro
65                  70                  75                  80

Pro Pro Val Ser Arg Lys Asp Leu Arg Gln Leu Ser Lys Asp Tyr Gln
                85                  90                  95

Gln Val Leu Leu Asp Val Arg Arg Ser Leu Arg Arg Phe Pro Pro Gly
            100                 105                 110

Met Pro Asp Glu Gln Arg Glu Gly Leu Gln Glu Glu Leu Ile Asp Ile
        115                 120                 125

Ile Leu Leu Ile Leu Asp Arg Asn Pro Gln Leu His Tyr Tyr Gln Gly
    130                 135                 140

Tyr His Asp Ile Val Val Thr Phe Leu Leu Val Val Gly Glu Arg Leu
145                 150                 155                 160

Ala Thr Ser Leu Val Glu Lys Leu Ser Thr His His Leu Arg Asp Phe
                165                 170                 175

Met Asp Pro Thr Met Asp Asn Thr Lys His Ile Leu Asn Tyr Leu Met
            180                 185                 190

Pro Ile Ile Asp Gln Val Asn Pro Glu Leu His Asp Phe Met Gln Ser
        195                 200                 205

Ala Glu Val Gly Thr Ile Phe Ala Leu Ser Trp Leu Ile Thr Trp Phe
    210                 215                 220

Gly His Val Leu Ser Asp Phe Arg His Val Val Arg Leu Tyr Asp Phe
225                 230                 235                 240

Phe Leu Ala Cys His Pro Leu Met Pro Ile Tyr Phe Ala Ala Val Ile
                245                 250                 255
```

```
Val Leu Tyr Arg Glu Gln Glu Val Leu Asp Cys Asp Cys Asp Met Ala
            260                 265                 270

Ser Val His His Leu Leu Ser Gln Ile Pro Gln Asp Leu Pro Tyr Glu
        275                 280                 285

Thr Leu Ile Ser Arg Ala Gly Asp Leu Phe Val Gln Phe Pro Pro Ser
        290                 295                 300

Glu Leu Ala Arg Glu Ala Ala Gln Gln Glu Ala Glu Arg Thr Ala
305                 310                 315                 320

Ala Ser Thr Phe Lys Asp Phe Glu Leu Ala Ser Ala Gln Gln Arg Pro
                325                 330                 335

Asp Met Val Leu Arg Gln Arg Phe Arg Gly Leu Leu Arg Pro Glu Thr
            340                 345                 350

Arg Thr Lys Asp Val Leu Thr Lys Pro Arg Thr Asn Arg Phe Val Lys
            355                 360                 365

Leu Ala Val Met Gly Leu Thr Val Ala Leu Gly Ala Ala Leu Ala
            370                 375                 380

Val Val Lys Ser Ala Leu Glu Trp Ala Pro Lys Phe Gln Leu Gln Leu
385                 390                 395                 400

Phe Pro

<210> SEQ ID NO 5
<211> LENGTH: 380
<212> TYPE: PRT
<213> ORGANISM: Cricetulus griseus
<220> FEATURE:
<223> OTHER INFORMATION: CERS2

<400> SEQUENCE: 5

Met Leu Gln Thr Leu Tyr Asp His Phe Trp Trp Asp Arg Leu Trp Leu
1               5                   10                  15

Pro Val Asn Leu Thr Trp Ala Asp Leu Glu Asp Arg Asp Gly Arg Val
            20                  25                  30

Tyr Ala Lys Ala Ser Asp Leu Tyr Ile Thr Leu Pro Leu Ala Leu Val
        35                  40                  45

Phe Leu Val Ile Arg Tyr Phe Phe Glu Leu Tyr Val Ala Thr Pro Leu
50                  55                  60

Ala Ala Leu Leu Asn Val Lys Glu Lys Thr Arg Leu Arg Ala Pro Pro
65                  70                  75                  80

Asn Val Thr Leu Glu His Phe Tyr Leu Thr Asn Gly Lys Gln Pro Lys
                85                  90                  95

Gln Val Glu Val Glu Leu Leu Ser Arg Gln Ser Gly Leu Ser Gly Arg
            100                 105                 110

Gln Ile Glu Arg Trp Phe Arg Arg Arg Asn Gln Asp Arg Pro Ser
        115                 120                 125

Leu Leu Lys Lys Phe Arg Glu Ala Ser Trp Arg Phe Thr Phe Tyr Leu
130                 135                 140

Ile Ala Phe Val Ala Gly Met Ala Val Ile Val Asp Lys Pro Trp Phe
145                 150                 155                 160

Tyr Asp Leu Arg Lys Val Trp Glu Gly Tyr Pro Ile Gln Ser Ile Val
                165                 170                 175

Pro Ser Gln Tyr Trp Tyr Tyr Met Ile Glu Leu Ser Phe Tyr Trp Ser
            180                 185                 190

Leu Leu Phe Ser Ile Ala Ser Asp Val Lys Arg Lys Asp Phe Lys Glu
        195                 200                 205
```

-continued

```
Gln Ile Ile His His Val Ala Thr Ile Ile Leu Leu Ser Phe Ser Trp
    210                 215                 220

Phe Ala Asn Tyr Val Arg Ala Gly Thr Leu Ile Met Ala Leu His Asp
225                 230                 235                 240

Ser Ser Asp Tyr Leu Leu Glu Ser Ala Lys Met Phe Asn Tyr Ala Gly
                245                 250                 255

Trp Lys Asn Thr Cys Asn Asn Ile Phe Ile Val Phe Ala Ile Val Phe
            260                 265                 270

Ile Ile Thr Arg Leu Val Ile Met Pro Phe Trp Ile Leu His Cys Thr
                275                 280                 285

Leu Val Tyr Pro Leu Glu Leu Tyr Pro Ala Phe Phe Gly Tyr Tyr Phe
    290                 295                 300

Phe Asn Ile Met Met Ala Val Leu Gln Met Leu His Ile Phe Trp Ala
305                 310                 315                 320

Tyr Phe Ile Leu Arg Met Ala His Lys Phe Ile Thr Gly Lys Leu Val
                325                 330                 335

Glu Asp Glu Arg Ser Asp Arg Glu Glu Thr Glu Ser Ser Glu Gly Glu
            340                 345                 350

Glu Ala Ala Ala Gly Ala Gly Ala Lys Ser Arg Leu Leu Ser Asn Gly
                355                 360                 365

His Pro Ile Leu Asn Asn Asn His Pro Lys Asn Asp
    370                 375                 380
```

<210> SEQ ID NO 6
<211> LENGTH: 578
<212> TYPE: PRT
<213> ORGANISM: Cricetulus griseus
<220> FEATURE:
<223> OTHER INFORMATION: ATF6b

<400> SEQUENCE: 6

```
Met Glu Ser Leu Ala Pro Pro Leu Cys Leu Leu Gly Asp Asp Pro Ala
1               5                   10                  15

Ser Pro Phe Glu Thr Val Gln Ile Thr Val Gly Ser Val Ala Asp Asp
            20                  25                  30

Pro Ser Asp Ile Gln Thr Lys Val Glu Pro Ala Ser Pro Ser Ser Ser
        35                  40                  45

Val Asn Ser Glu Ala Ser Leu Leu Ser Ala Asp Ser Pro Ser Gln Ala
    50                  55                  60

Phe Ile Gly Glu Glu Val Leu Glu Val Lys Thr Glu Ser Pro Ser Pro
65                  70                  75                  80

Pro Gly Cys Leu Leu Trp Asp Val Pro Ala Pro Ser Leu Gly Ala Val
                85                  90                  95

Gln Ile Ser Met Gly Pro Ser Pro Val Ser Ser Gly Lys Ala Pro
            100                 105                 110

Ala Thr Arg Lys Pro Pro Leu Gln Pro Lys Pro Val Val Leu Thr Thr
        115                 120                 125

Val Gln Val Pro Pro Arg Ala Gly Pro Pro Ser Thr Thr Val Leu Leu
    130                 135                 140

Gln Pro Leu Val Gln Pro Ala Val Ser Pro Val Leu Ile Gln
145                 150                 155                 160

Gly Ala Ile Arg Val Gln Pro Glu Gly Pro Ala Pro Ala Val Pro Arg
                165                 170                 175

Pro Glu Arg Lys Ser Ile Val Pro Ala Pro Leu Pro Gly Asn Ser Cys
            180                 185                 190
```

Pro Pro Glu Val Asp Ala Lys Leu Leu Lys Arg Gln Gln Arg Met Ile
                195                 200                 205

Lys Asn Arg Glu Ser Ala Cys Gln Ser Arg Arg Lys Lys Lys Glu Tyr
210                 215                 220

Leu Gln Gly Leu Glu Ala Arg Leu Gln Ala Val Leu Ala Asp Asn Gln
225                 230                 235                 240

Gln Leu Arg Arg Glu Asn Ala Ala Leu Arg Arg Arg Leu Glu Thr Leu
            245                 250                 255

Leu Thr Glu Asn Ser Glu Leu Lys Leu Gly Ser Gly Asn Arg Lys Val
            260                 265                 270

Val Cys Ile Met Val Phe Leu Leu Phe Ile Ala Phe Asn Phe Gly Pro
            275                 280                 285

Val Ser Ile Ser Glu Pro Pro Pro Ala Pro Ile Ser Pro Arg Met Ser
        290                 295                 300

Arg Glu Glu Ala Arg Pro Arg Arg His Leu Leu Glu Phe Ser Glu Gln
305                 310                 315                 320

Gly Pro Ala His Gly Val Glu Pro Leu Gln Lys Ala Ala Arg Gly Pro
                325                 330                 335

Glu Glu Arg Gln Pro Ser Pro Ala Gly Arg Pro Ser Phe Arg Asn Leu
            340                 345                 350

Thr Ala Phe Pro Gly Gly Ala Lys Glu Leu Leu Arg Asp Leu Asp
            355                 360                 365

Gln Leu Phe Leu Ala Ser Asp Cys Arg His Phe Asn Arg Thr Glu Ser
        370                 375                 380

Leu Arg Leu Ala Asp Glu Leu Ser Gly Trp Val Gln Arg His Gln Arg
385                 390                 395                 400

Gly Arg Arg Arg Met Pro His Arg Ala Gln Glu Arg Gln Lys Ser Gln
                405                 410                 415

Leu Arg Lys Lys Ser Pro Pro Val Lys Pro Val Pro Thr Gln Pro Pro
            420                 425                 430

Gly Pro Pro Glu Arg Asp Pro Val Gly Gln Leu Gln Leu Tyr Arg His
            435                 440                 445

Pro Gly Arg Ser Gln Pro Glu Phe Leu Asp Ala Ile Asp Arg Arg Glu
450                 455                 460

Asp Thr Phe Tyr Val Val Ser Phe Arg Arg Asp His Leu Leu Leu Pro
465                 470                 475                 480

Ala Ile Ser His Asn Lys Thr Ser Arg Pro Lys Met Ser Leu Val Met
                485                 490                 495

Pro Ala Met Ala Pro Asn Glu Thr Val Ser Gly Arg Gly Pro Pro Gly
            500                 505                 510

Asp Tyr Glu Glu Met Met Gln Ile Glu Cys Glu Val Met Asp Thr Arg
            515                 520                 525

Val Ile His Ile Lys Thr Ser Thr Val Pro Pro Ser Leu Arg Lys Gln
530                 535                 540

Pro Ser Pro Thr Pro Gly Asn Thr Thr Gly Gly Pro Leu Pro Ala Ser
545                 550                 555                 560

Ala Ala Ser Gln Ala Ser Gln Ala Ser His Gln Pro Leu Tyr Leu Asn
                565                 570                 575

His Pro

<210> SEQ ID NO 7
<211> LENGTH: 19
<212> TYPE: RNA
<213> ORGANISM: Artificial Sequence

```
<220> FEATURE:
<223> OTHER INFORMATION: siRNA siTbc1D20#1

<400> SEQUENCE: 7
agaacuaauc gacauuauc                                                  19

<210> SEQ ID NO 8
<211> LENGTH: 19
<212> TYPE: RNA
<213> ORGANISM: Artificial Sequence
<220> FEATURE:
<223> OTHER INFORMATION: siRNA siCerS2#1

<400> SEQUENCE: 8
agagucggcu ccuaucuaa                                                  19

<210> SEQ ID NO 9
<211> LENGTH: 19
<212> TYPE: RNA
<213> ORGANISM: Artificial Sequence
<220> FEATURE:
<223> OTHER INFORMATION: siRNA siArtf6b#1

<400> SEQUENCE: 9
ccuccucagg uucaguuca                                                  19

<210> SEQ ID NO 10
<211> LENGTH: 19
<212> TYPE: RNA
<213> ORGANISM: Artificial Sequence
<220> FEATURE:
<223> OTHER INFORMATION: siRNA siAtf6b#2

<400> SEQUENCE: 10
gcagcgaaug aucaagaac                                                  19

<210> SEQ ID NO 11
<211> LENGTH: 19
<212> TYPE: RNA
<213> ORGANISM: Artificial Sequence
<220> FEATURE:
<223> OTHER INFORMATION: siRNA siAtf6b#3

<400> SEQUENCE: 11
agacaccuuc uauguuguc                                                  19

<210> SEQ ID NO 12
<211> LENGTH: 21
<212> TYPE: RNA
<213> ORGANISM: Artificial Sequence
<220> FEATURE:
<223> OTHER INFORMATION: shRNA shTbc1D20#1

<400> SEQUENCE: 12
aauccuugcu caacugucga a                                               21

<210> SEQ ID NO 13
<211> LENGTH: 21
<212> TYPE: RNA
<213> ORGANISM: Artificial Sequence
<220> FEATURE:
<223> OTHER INFORMATION: shRNA shCerS2#1
```

<400> SEQUENCE: 13
uuaaguucac aggcagccau a                                              21

<210> SEQ ID NO 14
<211> LENGTH: 21
<212> TYPE: RNA
<213> ORGANISM: Artificial Sequence
<220> FEATURE:
<223> OTHER INFORMATION: shRNA shCerS2#2

<400> SEQUENCE: 14
ugauguagag gucugaggcu u                                              21

<210> SEQ ID NO 15
<211> LENGTH: 21
<212> TYPE: RNA
<213> ORGANISM: Artificial Sequence
<220> FEATURE:
<223> OTHER INFORMATION: shRNA shAtf6b#1

<400> SEQUENCE: 15
uccaucuuca cacugaggac c                                              21

<210> SEQ ID NO 16
<211> LENGTH: 64
<212> TYPE: DNA
<213> ORGANISM: Artificial Sequence
<220> FEATURE:
<223> OTHER INFORMATION: shTbc1D20#1_oligonucleotide_forward

<400> SEQUENCE: 16
tgctgaatcc ttgctcaact gtcgaagttt tggccactga ctgacttcga caggagcaag    60
gatt                                                                 64

<210> SEQ ID NO 17
<211> LENGTH: 64
<212> TYPE: DNA
<213> ORGANISM: Artificial Sequence
<220> FEATURE:
<223> OTHER INFORMATION: shTBC1F20#1_oligonucleotide_reverse

<400> SEQUENCE: 17
cctgaatcct tgctcctgtc gaagtcagtc agtggccaaa acttcgacag ttgagcaagg    60
attc                                                                 64

<210> SEQ ID NO 18
<211> LENGTH: 64
<212> TYPE: DNA
<213> ORGANISM: Artificial Sequence
<220> FEATURE:
<223> OTHER INFORMATION: shCerS2#1_oligonucleotide_forward

<400> SEQUENCE: 18
tgctgttaag ttcacaggca gccatagttt tggccactga ctgactatgg ctgtgtgaac    60
ttaa                                                                 64

<210> SEQ ID NO 19
<211> LENGTH: 64
<212> TYPE: DNA
<213> ORGANISM: Artificial Sequence
<220> FEATURE:
<223> OTHER INFORMATION: shCerS2#1_oligonucleotide_reverse

```
<400> SEQUENCE: 19
cctgttaagt tcacacagcc atagtcagtc agtggccaaa actatggctg cctgtgaact    60
taac                                                                  64

<210> SEQ ID NO 20
<211> LENGTH: 64
<212> TYPE: DNA
<213> ORGANISM: Artificial Sequence
<220> FEATURE:
<223> OTHER INFORMATION: shCerS2#2_oligonucleotide_forward

<400> SEQUENCE: 20
tgctgtgatg tagaggtctg aggcttgttt tggccactga ctgacaagcc tcacctctac    60
atca                                                                  64

<210> SEQ ID NO 21
<211> LENGTH: 64
<212> TYPE: DNA
<213> ORGANISM: Artificial Sequence
<220> FEATURE:
<223> OTHER INFORMATION: shCerS2#2_oligonucleotide_reverse

<400> SEQUENCE: 21
cctgtgatgt agaggtgagg cttgtcagtc agtggccaaa acaagcctca gacctctaca    60
tcac                                                                  64

<210> SEQ ID NO 22
<211> LENGTH: 64
<212> TYPE: DNA
<213> ORGANISM: Artificial Sequence
<220> FEATURE:
<223> OTHER INFORMATION: shAtf6b#1_oligonucleotide_forward

<400> SEQUENCE: 22
tgctgtccat cttcacactg aggaccgttt tggccactga ctgacggtcc tcagtgaaga    60
tgga                                                                  64

<210> SEQ ID NO 23
<211> LENGTH: 64
<212> TYPE: DNA
<213> ORGANISM: Artificial Sequence
<220> FEATURE:
<223> OTHER INFORMATION: shAtf6b#1_oligonucleotide_reverse

<400> SEQUENCE: 23
cctgtccatc ttcactgagg accgtcagtc agtggccaaa acggtcctca gtgtgaagat    60
ggac                                                                  64

<210> SEQ ID NO 24
<211> LENGTH: 463
<212> TYPE: PRT
<213> ORGANISM: Artificial Sequence
<220> FEATURE:
<223> OTHER INFORMATION: mAb1 heavy chain

<400> SEQUENCE: 24
```

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Lys
            20                  25                  30

-continued

```
Pro Gly Gly Ser Leu Arg Leu Ser Cys Ala Ala Ser Gly Phe Thr Phe
             35                  40                  45
Ser Ser Tyr Asp Met Ser Trp Val Arg Gln Ala Pro Gly Lys Gly Leu
 50                  55                  60
Glu Trp Val Ser Thr Ile Ser Ser Gly Gly Ser Tyr Thr Tyr Tyr Leu
 65                  70                  75                  80
Asp Ser Ile Lys Gly Arg Phe Thr Ile Ser Arg Asp Asn Ala Lys Asn
                 85                  90                  95
Ser Leu Tyr Leu Gln Met Asn Ser Leu Arg Ala Glu Asp Thr Ala Val
                100                 105                 110
Tyr Tyr Cys Ala Arg Gln Gly Leu Asp Tyr Trp Gly Arg Gly Thr Leu
            115                 120                 125
Val Thr Val Ser Ser Ala Ser Thr Lys Gly Pro Ser Val Phe Pro Leu
130                 135                 140
Ala Pro Ser Ser Lys Ser Thr Ser Gly Gly Thr Ala Ala Leu Gly Cys
145                 150                 155                 160
Leu Val Lys Asp Tyr Phe Pro Glu Pro Val Thr Val Ser Trp Asn Ser
                165                 170                 175
Gly Ala Leu Thr Ser Gly Val His Thr Phe Pro Ala Val Leu Gln Ser
                180                 185                 190
Ser Gly Leu Tyr Ser Leu Ser Ser Val Val Thr Val Pro Ser Ser Ser
            195                 200                 205
Leu Gly Thr Gln Thr Tyr Ile Cys Asn Val Asn His Lys Pro Ser Asn
210                 215                 220
Thr Lys Val Asp Lys Lys Val Glu Pro Lys Ser Cys Asp Lys Thr His
225                 230                 235                 240
Thr Cys Pro Pro Cys Pro Ala Pro Glu Leu Leu Gly Gly Pro Ser Val
                245                 250                 255
Phe Leu Phe Pro Pro Lys Pro Lys Asp Thr Leu Met Ile Ser Arg Thr
                260                 265                 270
Pro Glu Val Thr Cys Val Val Val Asp Val Ser His Glu Asp Pro Glu
            275                 280                 285
Val Lys Phe Asn Trp Tyr Val Asp Gly Val Glu Val His Asn Ala Lys
290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Pro Ala Pro Ile Glu Lys Thr Ile
                340                 345                 350
Ser Lys Ala Lys Gly Gln Pro Arg Glu Pro Gln Val Tyr Thr Leu Pro
            355                 360                 365
Pro Ser Arg Asp Glu Leu Thr Lys Asn Gln Val Ser Leu Thr Cys Leu
370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
                420                 425                 430
```

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
    450                 455                 460

<210> SEQ ID NO 25
<211> LENGTH: 233
<212> TYPE: PRT
<213> ORGANISM: Artificial Sequence
<220> FEATURE:
<223> OTHER INFORMATION: mAb1 light chain

<400> SEQUENCE: 25

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Tyr Gln Gln Lys Pro Gly Gln Ala Pro Arg
    50                  55                  60

Leu Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 26
<211> LENGTH: 470
<212> TYPE: PRT
<213> ORGANISM: Artificial Sequence
<220> FEATURE:
<223> OTHER INFORMATION: mAb2 heavy chain

<400> SEQUENCE: 26

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Val Ser Gly Tyr Ser Ile
        35                  40                  45

Thr Ser Gly Tyr Ser Trp Asn Trp Ile Arg Gln Ala Pro Gly Lys Gly
 50                  55                  60

Leu Glu Trp Val Ala Ser Ile Thr Tyr Asp Gly Ser Thr Asn Tyr Asn
 65                  70                  75                  80

Pro Ser Val Lys Gly Arg Ile Thr Ile Ser Arg Asp Asp Ser Lys Asn
                 85                  90                  95

Thr Phe Tyr Leu Gln Met Asn Ser Leu Arg Ala Glu Asp Thr Ala Val
                100                 105                 110

Tyr Tyr Cys Ala Arg Gly Ser His Tyr Phe Gly His Trp His Phe Ala
            115                 120                 125

Val Trp Gly Gln Gly Thr Leu Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

```
Ser Val Met His Glu Ala Leu His Asn His Tyr Thr Gln Lys Ser Leu
    450                 455                 460

Ser Leu Ser Pro Gly Lys
465             470

<210> SEQ ID NO 27
<211> LENGTH: 237
<212> TYPE: PRT
<213> ORGANISM: Artificial Sequence
<220> FEATURE:
<223> OTHER INFORMATION: mAb2 light chain

<400> SEQUENCE: 27

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Ile Thr Cys Arg Ala Ser Gln Ser Val
        35                  40                  45

Asp Tyr Asp Gly Asp Ser Tyr Met Asn Trp Tyr Gln Gln Lys Pro Gly
    50                  55                  60

Lys Ala Pro Lys Leu Leu Ile Tyr Ala Ala Ser Tyr Leu Glu Ser Gly
65                  70                  75                  80

Val Pro Ser Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Ser His Glu Asp Pro Tyr Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 28
<211> LENGTH: 66
<212> TYPE: DNA
<213> ORGANISM: Artificial Sequence
<220> FEATURE:
<223> OTHER INFORMATION: hsa-miRNA-1287_oligonucleotide_forward

<400> SEQUENCE: 28
tgctgtgctg gatcagtggt tcgagtcgtt ttggccactg actgacgact cgaaccacat    60
ccagca                                                               66
```

```
<210> SEQ ID NO 29
<211> LENGTH: 66
<212> TYPE: DNA
<213> ORGANISM: Artificial Sequence
<220> FEATURE:
<223> OTHER INFORMATION: hsa-miR-1287_oligonucleotide_reverse

<400> SEQUENCE: 29
cctgtgctgg atgtggttcg agtcgtcagt cagtggccaa aacgactcga accactgatc      60
cagcac                                                                66

<210> SEQ ID NO 30
<211> LENGTH: 64
<212> TYPE: DNA
<213> ORGANISM: Artificial Sequence
<220> FEATURE:
<223> OTHER INFORMATION: hsa-miRNA-1978_oligonucleotide_forward

<400> SEQUENCE: 30
tgctgggttt ggtcctagcc tttctagttt tggccactga ctgactagaa aggctaacca      60
aacc                                                                  64

<210> SEQ ID NO 31
<211> LENGTH: 64
<212> TYPE: DNA
<213> ORGANISM: Artificial Sequence
<220> FEATURE:
<223> OTHER INFORMATION: hsa-miR-1978_oligonucleotide_reverse

<400> SEQUENCE: 31
cctgggtttg gttagccttt ctagtcagtc agtggccaaa actagaaagg ctaggaccaa      60
accc                                                                  64

<210> SEQ ID NO 32
<211> LENGTH: 22
<212> TYPE: RNA
<213> ORGANISM: Homo sapiens
<220> FEATURE:
<223> OTHER INFORMATION: hsa-miRNA-1287

<400> SEQUENCE: 32
ugcuggauca gugguucgag uc                                              22

<210> SEQ ID NO 33
<211> LENGTH: 21
<212> TYPE: RNA
<213> ORGANISM: Homo sapiens
<220> FEATURE:
<223> OTHER INFORMATION: hsa-miRNA-1978

<400> SEQUENCE: 33 gguuggucc uagccuuucu a                                                21

<210> SEQ ID NO 34
<211> LENGTH: 22
<212> TYPE: RNA
<213> ORGANISM: Artificial Sequence
<220> FEATURE:
<223> OTHER INFORMATION: negative control miRNA

<400> SEQUENCE: 34
gaaauguacu gcgcguggag ac                                              22
```

```
<210> SEQ ID NO 35
<211> LENGTH: 64
<212> TYPE: DNA
<213> ORGANISM: Artificial Sequence
<220> FEATURE:
<223> OTHER INFORMATION: shAtf6B#2_oligonucleotide_forward

<400> SEQUENCE: 35
tgctgttcac ttccagaacc tcctctgttt tggccactga ctgacagagg aggctggaag      60
tgaa                                                                  64

<210> SEQ ID NO 36
<211> LENGTH: 64
<212> TYPE: DNA
<213> ORGANISM: Artificial Sequence
<220> FEATURE:
<223> OTHER INFORMATION: shAtf6b#2_oligonucleotide_reverse

<400> SEQUENCE: 36
cctgttcact tccagcctcc tctgtcagtc agtggccaaa acagaggagg ttctggaagt      60
gaac                                                                  64

<210> SEQ ID NO 37
<211> LENGTH: 21
<212> TYPE: RNA
<213> ORGANISM: Artificial Sequence
<220> FEATURE:
<223> OTHER INFORMATION: shAtf6b#2

<400> SEQUENCE: 37
uucacuucca gaaccuccuc u                                               21

<210> SEQ ID NO 38
<211> LENGTH: 19
<212> TYPE: RNA
<213> ORGANISM: Artificial Sequence
<220> FEATURE:
<223> OTHER INFORMATION: siRNA NT-control#1

<400> SEQUENCE: 38
ugguuuacau gucgacuaa                                                  19

<210> SEQ ID NO 39
<211> LENGTH: 19
<212> TYPE: RNA
<213> ORGANISM: Artificial Sequence
<220> FEATURE:
<223> OTHER INFORMATION: siRNA NT-control#2

<400> SEQUENCE: 39
ugguuuacau guuguguga                                                  19

<210> SEQ ID NO 40
<211> LENGTH: 19
<212> TYPE: RNA
<213> ORGANISM: Artificial Sequence
<220> FEATURE:
<223> OTHER INFORMATION: siRNA NT-control#3

<400> SEQUENCE: 40
ugguuuacau guuuucuga                                                  19
```

```
<210> SEQ ID NO 41
<211> LENGTH: 19
<212> TYPE: RNA
<213> ORGANISM: Artificial Sequence
<220> FEATURE:
<223> OTHER INFORMATION: siRNA NT-control#4

<400> SEQUENCE: 41
ugguuuacau guuuuccua                                                     19

<210> SEQ ID NO 42
<211> LENGTH: 20
<212> TYPE: DNA
<213> ORGANISM: Artificial Sequence
<220> FEATURE:
<223> OTHER INFORMATION: qPCR primer (Atf6b) forward

<400> SEQUENCE: 42
gagcaggatg tcccgtttga                                                    20

<210> SEQ ID NO 43
<211> LENGTH: 20
<212> TYPE: DNA
<213> ORGANISM: Artificial Sequence
<220> FEATURE:
<223> OTHER INFORMATION: qPCR primer (Atf6b) reverse

<400> SEQUENCE: 43
agctcaggga ggaggaagag                                                    20

<210> SEQ ID NO 44
<211> LENGTH: 20
<212> TYPE: DNA
<213> ORGANISM: Artificial Sequence
<220> FEATURE:
<223> OTHER INFORMATION: qPCR primer (Tbc1D20) forward

<400> SEQUENCE: 44
ccctgaacag tgatcccacc                                                    20

<210> SEQ ID NO 45
<211> LENGTH: 20
<212> TYPE: DNA
<213> ORGANISM: Artificial Sequence
<220> FEATURE:
<223> OTHER INFORMATION: qPCR primer (Tbc1D20) reverse

<400> SEQUENCE: 45
atccttcctt gacacaggcg                                                    20

<210> SEQ ID NO 46
<211> LENGTH: 20
<212> TYPE: DNA
<213> ORGANISM: Artificial Sequence
<220> FEATURE:
<223> OTHER INFORMATION: qPCR primer (CerS2) forward

<400> SEQUENCE: 46
cccatacaga gcatcgtccc                                                    20

<210> SEQ ID NO 47
<211> LENGTH: 20
<212> TYPE: DNA
<213> ORGANISM: Artificial Sequence
<220> FEATURE:
<223> OTHER INFORMATION: qPCR primer (CerS2) reverse
```

<400> SEQUENCE: 47
ggcaaaccag gagaagctga                                               20

<210> SEQ ID NO 48
<211> LENGTH: 22
<212> TYPE: DNA
<213> ORGANISM: Artificial Sequence
<220> FEATURE:
<223> OTHER INFORMATION: qPCR primer (CHOP) forward

<400> SEQUENCE: 48
gaccctgttt ctttcccttc ag                                            22

<210> SEQ ID NO 49
<211> LENGTH: 21
<212> TYPE: DNA
<213> ORGANISM: Artificial Sequence
<220> FEATURE:
<223> OTHER INFORMATION: qPCR primer (CHOP) reverse

<400> SEQUENCE: 49
ggactgggtt ctgctttcag g                                             21

<210> SEQ ID NO 50
<211> LENGTH: 20
<212> TYPE: DNA
<213> ORGANISM: Artificial Sequence
<220> FEATURE:
<223> OTHER INFORMATION: qPCR primer (GRP78) forward

<400> SEQUENCE: 50
accacctatt cctgcgttgg                                               20

<210> SEQ ID NO 51
<211> LENGTH: 20
<212> TYPE: DNA
<213> ORGANISM: Artificial Sequence
<220> FEATURE:
<223> OTHER INFORMATION: qPCR primer (GRP78) reverse

<400> SEQUENCE: 51
agaccgtgtt ctcgggattg                                               20

<210> SEQ ID NO 52
<211> LENGTH: 20
<212> TYPE: DNA
<213> ORGANISM: Artificial Sequence
<220> FEATURE:
<223> OTHER INFORMATION: qPCR primer (Herpud1) forward

<400> SEQUENCE: 52
gaagagtccc aaccagcgtc                                               20

<210> SEQ ID NO 53
<211> LENGTH: 21
<212> TYPE: DNA
<213> ORGANISM: Artificial Sequence
<220> FEATURE:
<223> OTHER INFORMATION: qPCR primer (Herpud1) reverse

<400> SEQUENCE: 53
atgtcgcttt tcctgctttg g                                             21

MAMMALIAN CELLS FOR PRODUCING A SECRETED PROTEIN

TECHNICAL FIELD

The invention relates to the field of cell culture technology. It concerns the knockdown, such as by using RNA interference, or gene knockout, of activating transcription factor 6 beta (ATF6B), or the combination of ceramide synthase 2 (CERS2) and TBC1 domain family member 20 (TBC1D20), proteins which play central roles in the cellular secretion pathway. This downregulation leads to improved secretion of biopharmaceutically relevant products produced in mammalian cells. The invention specifically relates to mammalian cells having enhanced secretion of a recombinant therapeutic protein compared to a control cell, a method of producing said mammalian cell, a method for the production of a recombinant secreted therapeutic protein and the use of said mammalian cell for increasing the yield of a recombinant secreted therapeutic protein.

BACKGROUND

Improving titers of therapeutic proteins in production, making processes more efficient, is a clear goal in industry. This can lead to reduced costs and shortened timelines to supply protein material for clinical studies and markets. As overall yields in production processes are determined by cell specific productivity of the individual cell, as well as the number of viable cells present in the process, strategies to improve production efficiency usually aim to increase either of these two parameters, without negatively affecting the other.

There is a need for improving recombinant protein production in mammalian cells, by increasing the specific productivity and/or the total yield (i.e., titer or concentration) of the protein in the cell culture supernatant, which is generally applicable and not dependent on the individual cell line or protein to be produced.

Engineering strategies aiming to improve titers of therapeutic proteins can focus on different stages of protein secretion, such as protein folding, post-transcriptional regulation and/or secretion. However, one of the challenges associated with modifying the behaviour of cells to achieve favourable phenotypes for the production of recombinant proteins is the complex nature of intracellular regulation circuits. Targeting the expression of one gene or protein is not useful unless it is a rate-limiting factor in a critical pathway or it is a transcription factor with the potential to alter expression of a whole set of target genes. For this reason, microRNAs, as regulators of whole networks of genes, were used in protein-producing cell lines (WO 2013/182553). Targeting whole networks of genes is an undefined process unless all target genes are identified. Also regulation of some of those genes may not be favourable for protein secretion or counteract the regulation of other genes. It is an objective of the present invention to downregulate specific proteins that constitute a bottleneck in protein secretion in order to have a higher yield of secreted therapeutic proteins.

Expression of recombinant therapeutic proteins leads to an increase of the total protein amount that is translocated to the endoplasmic reticulum (ER) for further processing and subsequent secretion. Consequently, the protein folding capacity of the ER is one potential bottleneck for protein production.

To this end, several studies are concerned with alterations in the unfolded protein response (UPR), an adaptive stress-response pathway that uses ER chaperones. Improved secretion of therapeutic proteins in recombinant producer cells was obtained by overexpression of UPR related transcription factors such as activating transcription factor 4 (ATF4) (Ohya T, et al., 2008. *Biotechnology and Bioengineering.* 100(2):317-324) the X-box binding protein-1 (XBP-1) (Tigges M, et al., 2006. *Metabolic Engineering.* 8:264-272; Becker E, et al., 2008. *Journal of Biotechnology.* 135:217-223) or the CCAAT-enhancer-binding protein homologous protein (CHOP) (Nishimiya D, et al., 2013. *Appl Microbiol Biotechnol.* 97:2531-2539). In 2009, Bommiasamy et al. showed that not only overexpression of XBP-1, but also the expression of a constitutively active form of activating transcription factor 6 alpha (ATF6α), increased the protein folding capacity of the ER (Bommiasamy et al., 2009, *Journal of Cell Sciences.* 122: 1626-1636).

A further bottleneck in the secretion of recombinant proteins is the delivery from the ER to the Golgi apparatus. The small GTPase Rab1 has a crucial role in the vesicular transport of proteins that have been processed in the ER. Due to its involvement in regulating the exit of secretory cargo from the ER and in COPII vesicle tethering (Haas A, et al., 2007. *Journal of Cell Science.* 120:2997-3010), an increase in Rab1 activity could be advantageous for the overall protein secretion of the cell. While overexpression of Rab1 has been described to enlarge the Golgi apparatus and led to the up-regulation of vesicle traffic genes participating in the ER-to-Golgi transport, its inactivation or depletion resulted in a blockage of ER exit (Haas A, et al., 2007. *Journal of Cell Science.* 120:2997-3010; Romero N, et al., 2013. MBoC. 24:617-632). Rab1 is inactivated by a specific GTPase-activating protein (GAP), namely TBC1 Domain Family, Member 20 (TBC1D20) (Haas A, et al., 2007. *Journal of Cell Science.* 120:2997-3010).

In addition to limitations in the protein folding capacity of the ER and the ER-to-Golgi transport, it has previously been shown that the protein transport at the Golgi complex may be a further bottle neck in recombinant protein secretion (Florin L, et al., 2009. *Journal of Biotechnology.* 141:84-90). Ceramides are a source of diacylglycerol (DAG), which regulates the activity of protein kinase D (PKD) (Hausser A, et al., 2005. *Nat Cell Biol.* 7(9):880-886; Fuchs Y F, et al., 2009. *Traffic.* 10:858-867; Baron C L and Malhotra V. 2002, Science 295(5553): 325-8). PKD is crucial for the transport of proteins from the Golgi to the plasma membrane by ceramide transfer protein (CERT) (Hanada K, et al., 2003. *Nature.* 426:803-809; Florin L, et al., 2009. *Journal of Biotechnology.* 141:84-90; Fugmann T, et al., *Journal of Cell Biology.* 178: 15-22). Ceramides are synthesized by six different isoforms of Ceramide Synthases (CERS1-6).

However, no specific proteins involved in the UPR or the secretory pathway have been identified that would loosen the above described bottlenecks upon downregulation and hence result in increased production of secreted proteins. Downregulation of genes may have technical advantages. For example, knock-out cells are stable with regard to this phenotype and marker genes can be excised. Also, RNAi expression is more easily controlled since a saturating level is usually reached and the expression level is less critical as for protein overexpression.

SUMMARY OF THE INVENTION

In the present invention it is shown that knocking-down selected target genes increased production of secreted proteins, particularly reducing ATF6B activity, or reducing CERS2 and TBC1D20 activity, exerts a positive effect on secreted product concentration, protein productivity and viable cell density. These results suggest that the targeting of ATF6B, or the combination of CERS2 and TBC1D20, are effective strategies for improving titers of therapeutic proteins, including antibodies.

By virtue of downregulation of ATF6B, CERS2 and TBC1D20 protein activity, it is now possible to engineer mammalian cells to improve their cell productivity and/or cell viability, in particular, to increase the amount of protein secreted by the cell culture. The mammalian cells, methods and uses provided herein allow for a more efficient and cost-effective production of secreted proteins, especially for antibody production. This may speed up drug development, since the generation of sufficient amounts of material for pre-clinical studies is critical with regard to overall development timelines. The objects of the present invention can further be used for the generation of one or several specific secreted proteins for either diagnostic purposes, research purposes (target identification, lead identification, and lead optimization) or manufacturing therapeutic proteins either on the market or in clinical development.

In one aspect, the invention relates to a mammalian cell having enhanced secretion of a recombinant therapeutic protein comprising (a) reduced expression of the host cell proteins TBC1 domain family member 20 (TBC1D20) and ceramide synthase 2 (CERS2); or (b) reduced expression of the host cell protein activating transcription factor 6 beta (ATF6B); wherein the mammalian cell further comprises one or more expression cassette(s) encoding a recombinant secreted therapeutic protein.

Another aspect of the invention relates to a mammalian cell having enhanced secretion of a recombinant therapeutic protein comprising reduced expression of the host cell proteins TBC1D20 and CERS2. Optionally the mammalian cell may further comprise one or more expression cassette(s) encoding a recombinant secreted therapeutic protein.

In the mammalian cell of the invention (a) the gene encoding the host cell protein comprises a genetic modification that inhibits expression of said host cell protein, or (b) the mammalian cell comprises a RNA oligonucleotide that inhibits expression of the gene encoding said host cell protein by RNA-interference, wherein the protein expression of TBC1D20 and CERS2 or the protein expression of ATF6B in the mammalian cell is reduced compared to the same mammalian cell not containing said genetic modification(s) or RNA oligonucleotide(s).

In a further aspect, the invention relates to a method of producing a mammalian cell with enhanced secretion of a recombinant therapeutic protein comprising (a) reducing expression of the host cell proteins TBC1D20 and CERS2, or of the host cell protein ATF6B in the mammalian cell by introducing (i) a genetic modification into a gene encoding the host cell protein that inhibits expression of said host cell protein, or (ii) a RNA oligonucleotide into the mammalian cell that inhibits expression of the gene encoding said host cell protein by RNA-interference, and (b) introducing one or more gene(s) encoding a recombinant secreted therapeutic protein. The method of the invention may further comprise the following steps: (c) selecting cells with enhanced secretion of the recombinant therapeutic protein; and (d) optionally culturing the cells obtained in step (c) under conditions which allow expression of one or more gene(s) encoding a recombinant secreted therapeutic protein. According to the method of the invention the protein expression of TBC1D20 and CERS2 or the protein expression of ATF6B in the mammalian cell is reduced compared to the same mammalian cell not containing said genetic modification(s) or RNA oligonucleotide(s).

The RNA-interference in the cell of the invention or in the method of the invention may be mediated by small hairpin RNA (shRNA) or short interfering RNA (siRNA). Preferably the mammalian cell is transfected with one or more expression vector(s) comprising a nucleotide sequence encoding said siRNA(s) or shRNA(s), more preferably the mammalian cell is stably transfected with one or more expression vector(s) encoding said siRNA(s) or shRNA(s). The siRNA used in the cell or the method of the invention may be (a) siTbc1D20#1 (SEQ ID NO: 7) or siCerS2#1 (SEQ ID NO: 8), or a combination thereof if TBC1D20 and/or CERS2 are targeted; or (b) one or more of siAtf6b #1 (SEQ ID NO: 9), siAtf6b #2 (SEQ ID NO: 10), and siAtf6b #3 (SEQ ID NO: 11) if ATF6b is targeted. The shRNA may comprise (a) shTbc1D20#1 (SEQ ID NO: 12), or one or more of shCerS2#1 (SEQ ID NO: 13) and shCerS2#2 (SEQ ID NO: 14), or a combination thereof, if TBC1D20 and/or CERS2 are targeted; or (b) one or more of shAtf6b #1 (SEQ ID NO: 15) and shAtf6b #2 (SEQ ID NO: 37), if ATF6b is targeted. The exemplary siRNAs and shRNAs are particularly suitable for hamster cells, such as CHO cells.

The genetic modification in the gene(s) encoding the host cell protein(s) TBC1D20 and CERS2, or ATF6B may be independently (a) a gene deletion; or (b) a mutation in the gene that inhibits expression of the host cell protein, preferably in the coding region of the gene and/or the promoter or regulatory region of the gene. The host cell protein TBC1D20 preferably has a sequence identity of at least 80% to the amino acid sequence of SEQ ID NO: 4, the host cell protein CERS2 preferably has a sequence identity of at least 80% to the amino acid sequence of SEQ ID NO: 5; and the host cell protein ATF6B preferably has sequence identity of at least 80% to the amino acid sequence of SEQ ID NO: 6.

According to the invention the recombinant secreted therapeutic protein may be an antibody, preferably a monoclonal antibody, a bi-specific antibody or a fragment thereof. Alternatively the recombinant secreted therapeutic protein may also be a Fc-fusion protein. The cell according to the invention or used in the method of the invention is preferably a rodent or a human cell, preferably a rodent cell, such as a CHO cell.

In a further aspect the invention also relates to a method for the production of a recombinant secreted therapeutic protein in a mammalian cell comprising (a) providing the mammalian cell of the invention, wherein the cell is transfected with a recombinant secreted therapeutic protein or providing the mammalian cell produced by the method of the invention, (b) culturing the mammalian cell of step (a) in a cell culture medium at conditions allowing production of the recombinant secreted therapeutic protein, (c) harvesting the recombinant secreted therapeutic protein, and optionally (d) purifying the recombinant secreted therapeutic protein.

In yet another aspect, the invention relates to the use of the mammalian cell of the invention or to the mammalian cell produced by the method of the invention for increasing the yield of a recombinant secreted therapeutic protein.

DESCRIPTION OF THE FIGURES

FIG. 1 shows IDENTIFICATION OF DIFFERENTIALLY EXPRESSED TARGET GENES OF MICRORNAS BY NEXT GENERATION SEQUENCING Panel (A) is a table showing that CHO-DG44 cells stably secreting an IgG1 antibody (mAb1) (CHO-mAb1 cells)

were transfected with each of the two microRNAs miR-1287 and miR-1978 having strong effects on antibody production and specific productivity. 12 hours after transfection transcriptome profiling by next generation sequencing (NGS) was used to identify direct target genes of the two miRNAs. Genes that were significantly downregulated with a |log 2|fold change>1 (gene expression in untransfected control cells (mock) was more than 2-fold) were defined as hits. The miR-1287 target gene ATF6B and the miR-1978 target genes CerS2 and Tbc1D20 were chosen for further analysis. Shown is the normalized fold change in expression (mock vs miRNA transfected) of the respective genes and its |log 2|. Effects of selected target genes on antibody production and specific productivity were first assessed by siRNA-mediated gene knockdown, followed by shRNA-mediated knockdown to investigate long-term depletion of the target genes. Panel (B) is a table listing the names and sequences of the siRNAs and shRNAs used in this study.

FIG. 2 shows VALIDATION OF TARGET GENES VIA QPCR (A) and (B), CHO-DG44 cells stably secreting the IgG1 antibody mAb1 were transfected with microRNA miR-c #1, miR-1287 or miR-1978. One day after transfection, RNA was extracted to quantify levels of mRNA of ATF6B, CerS2 and Tbc1D20 by qPCR. (C) and (D), Expression levels of these target genes were quantified for CHO-DG44 cells stably secreting the antibody mAb1 and further stably overexpressing either miR-1287 or miR-1978. Relative expression was calculated by normalizing to the reference gene beta actin. Panel (A) is a bar graph showing that transient transfection with miR-1287 resulted in a reduced expression level of ATF6B compared to untransfected cells (mock) (n=3, error bars=SEM of triplicates). Panel (B) is a bar graph showing that transient transfection with the miRNA miR-1978 resulted in decreased levels of CERS2 mRNA and TBC1D20 mRNA compared to untransfected cells (mock) (n=3, error bars=SEM of triplicates). (C)-(D) CHO-mAb1 cells stably secreting an IgG antibody were stably transfected with expression vectors encoding either miR-1287 or miR-1978 (pcDNA6.2-GW/emGFP-miR1287-miR1287 or pcDNA6.2-GW/emGFP-miR1978-miR1978) or a negative control sequence expression plasmid (pcDNA6.2-GW/emGFP-negative-control) and enriched for GFP positive cells by FACS. Panel (C) is a bar graph showing that CHO-mAb1 cells stably overexpressing miR-1287 showed reduced levels of ATF6B mRNA compared to parental CHO-mAb1 cells (n=3, error bars=SEM of triplicates). Panel (D) is a bar graph showing that CHO-mAb1 cells stably overexpressing miR-1978 showed reduced levels of both CERS2 and TBC1D20 compared to parental CHO-mAb1 cells (n=2, error bars=SEM of duplicates).

Figure 3A:
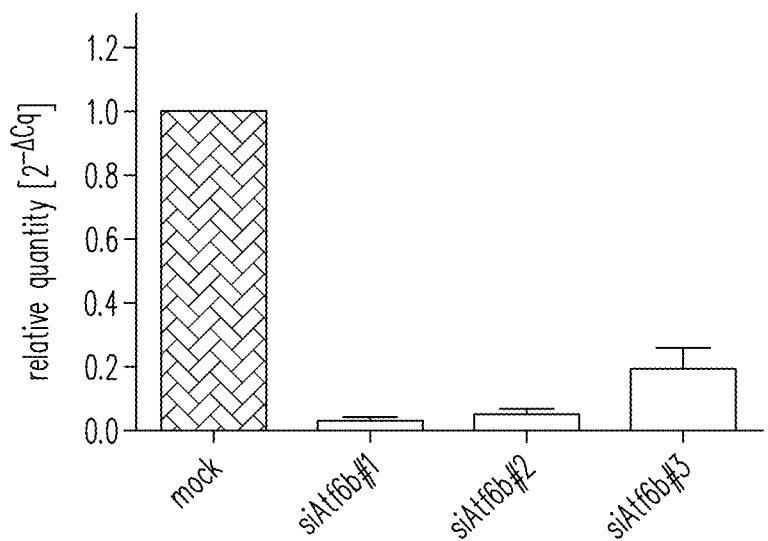
Figure 3B:
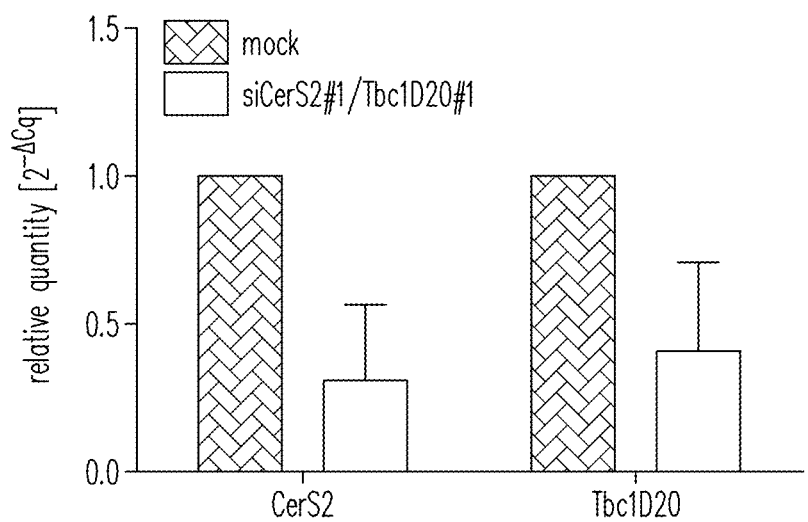

FIG. 3 shows KNOCKDOWN EFFICIENCY OF SIRNAS SPECIFIC FOR ATF6B, CERS2 AND TBC1D20

CHO-DG44 cells stably secreting the IgG1 antibody mAb1 were transfected with siRNAs specific for ATF6B or CERS2 and TBC1D20, respectively, and mRNA levels of ATF6B, CERS2 and TBC1D20 were quantified by qPCR. Panel (A) is a bar graph showing that an effective knockdown of ATF6B was observed by three independent siRNAs (siAft6b #1, siAft6b #2 and siAft6b #3) (n=3, error bars=SEM of triplicates). Panel (B) is a bar graph showing that combined knockdown of CERS2 and TBC1D20 was observed by nucleofection with both siRNAs simultaneously (siTbc1D20#1 and siCerS2#1) (n=2, error bars=SEM of duplicates).

Figure 4:
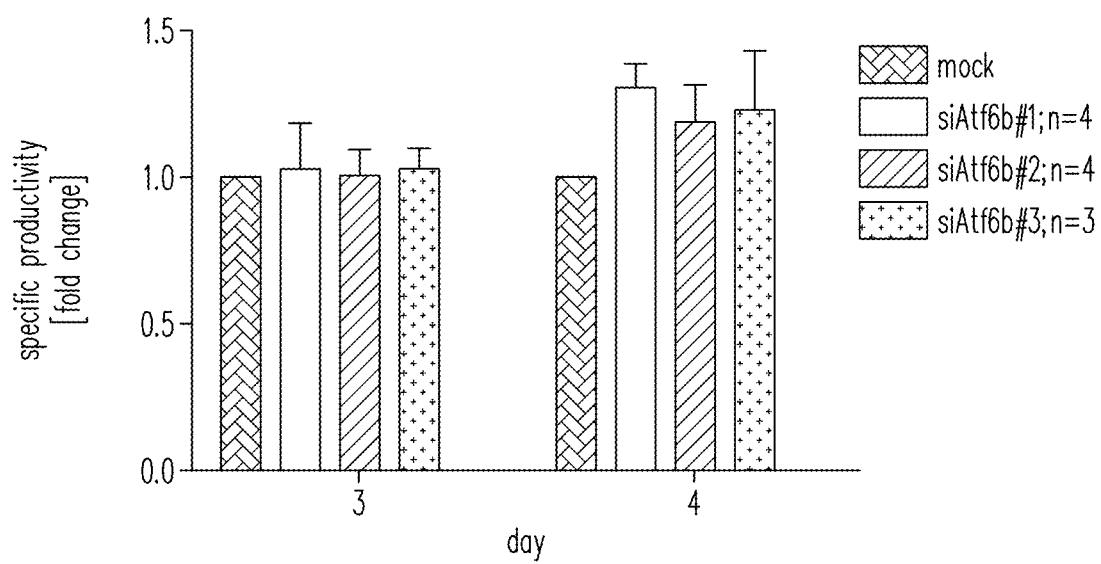

FIG. 4 shows the EFFECT OF ATF6B KNOCKDOWN ON PRODUCTIVITY OF CHO-mAb1 CELLS

CHO-mAb1 cells were transfected with each of three independent siRNAs specific for ATF6B (siAft6b #1, siAft6b #2 and siAft6b #3). Specific productivity on days 3 and 4 was calculated and normalized to non-transfected control cells (mock). Knockdown of ATF6B resulted in improved specific productivity at day 4 (n=3, error bars=SEM of triplicates).

Figure 5A:
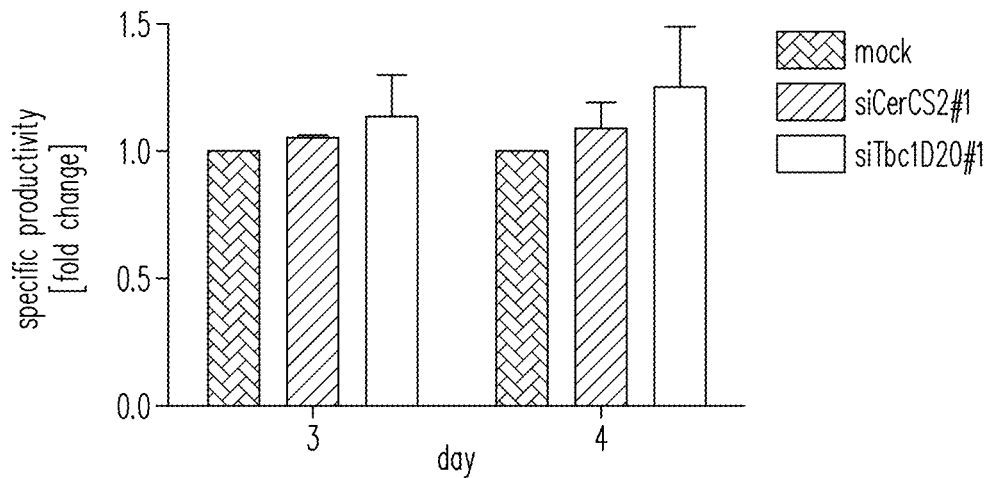
Figure 5B:
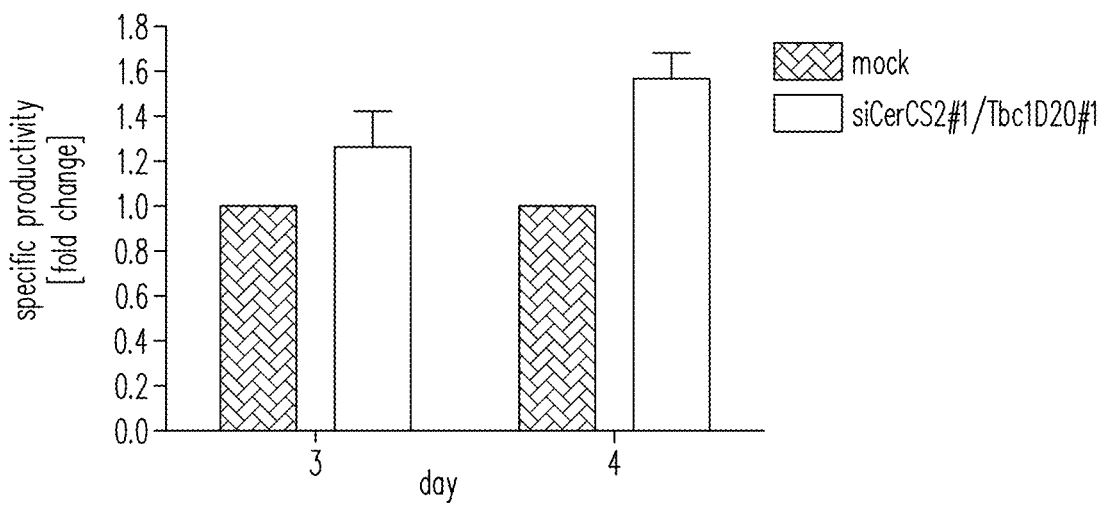

FIG. 5 shows the EFFECT OF COMBINED CERS2 AND TBC1D20 KNOCKDOWN ON PRODUCTIVITY OF CHO-mAB1 CELLS CHO-mAb1 cells were transfected with siRNAs against CERS2 and TBC1D20 (siTbc1D20#1 and siCerS2#1) (A) singly and (B) in combination. Specific productivity on days 3 and 4 was calculated and normalized to non-transfected control cells (mock). Panel (A) is a bar graph showing that a single knockdown of either CERS2 or TBC1D20 slightly increased the specific productivity at day 4 (n=2, error bars=SEM of duplicates). Panel (B) is a bar graph showing that a combined knockdown of CERS2 and TBC1D20 resulted in further improvement of the specific productivity at day 3 and day 4 (n=3, error bars=SEM of triplicates).

Figure 6:
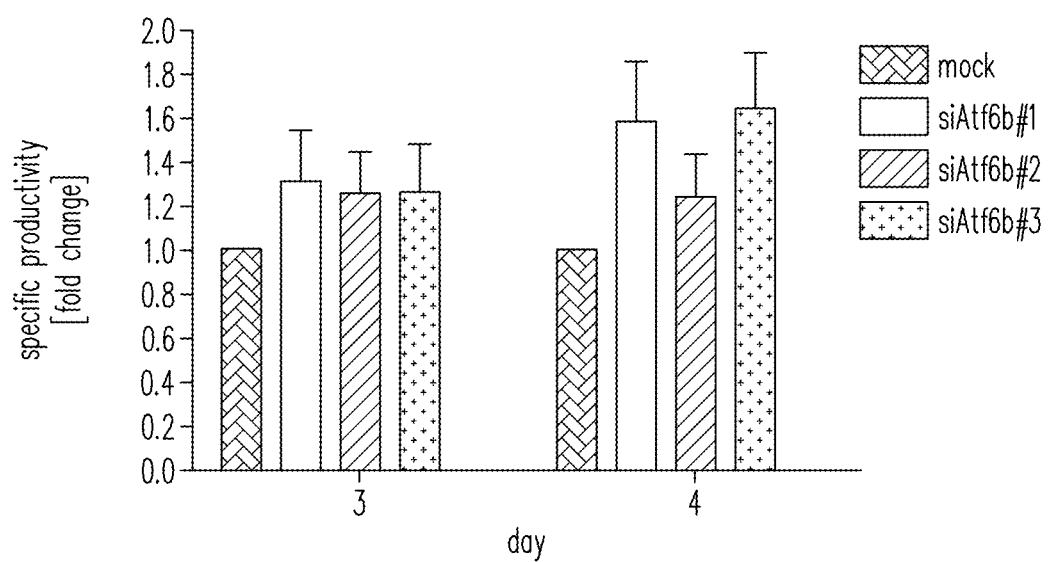

FIG. 6 shows the EFFECT OF ATF6B KNOCKDOWN ON PRODUCTIVITY OF CHO-mAB2 CELLS

A further CHO-DG44 cell clone stably secreting the IgG antibody mAb2 was transfected with each of three independent siRNAs specific for ATF6B (siAft6b #1, siAft6b #2 and siAft6b #3). Specific productivity on days 3 and 4 was calculated and normalized to non-transfected control cells (mock). Knockdown of ATF6B resulted in improved specific productivity at days 3 and 4 (n=3, error bars=SEM of replicates).

Figure 7:
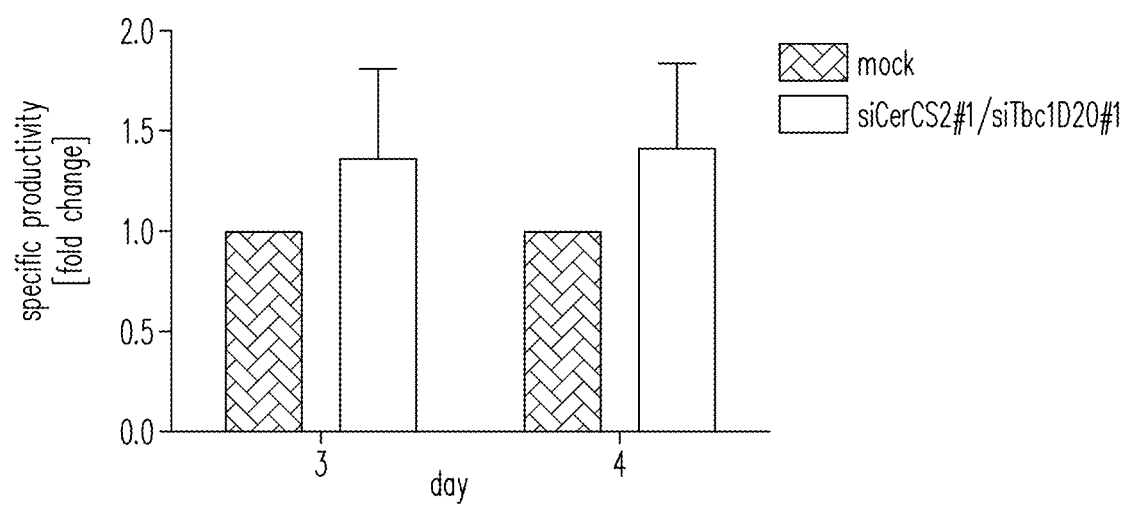
Figure 8A:
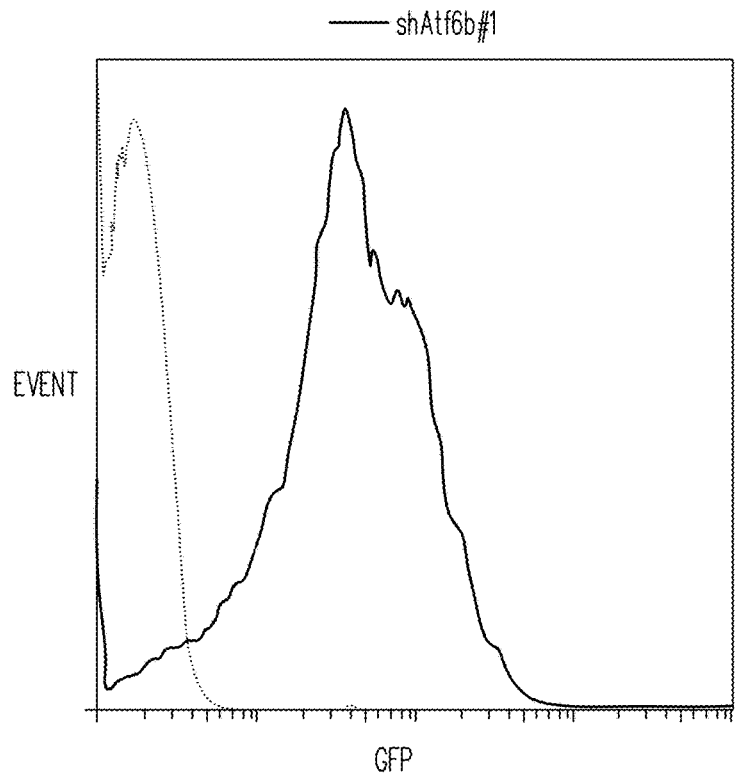
Figure 8B:
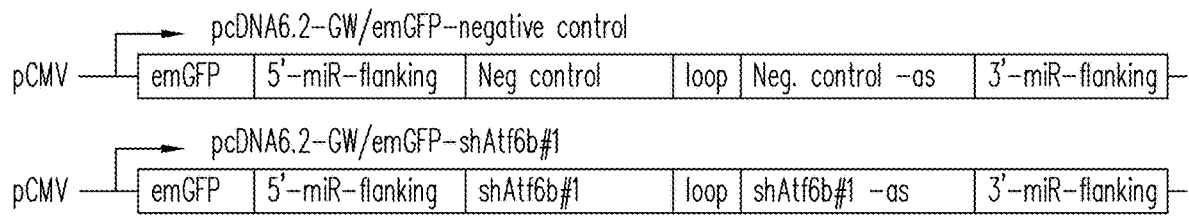
Figure 8C:
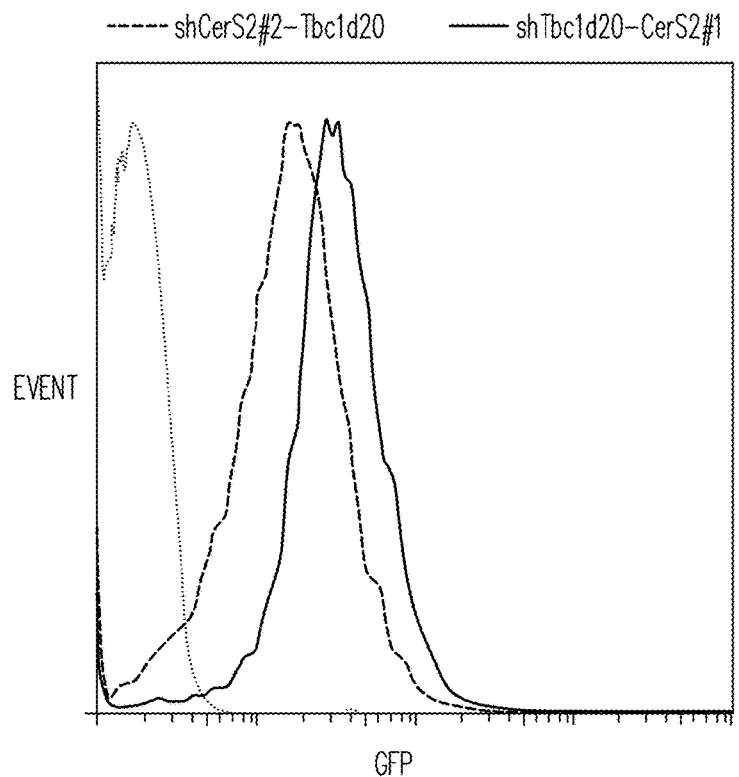
Figure 8D:
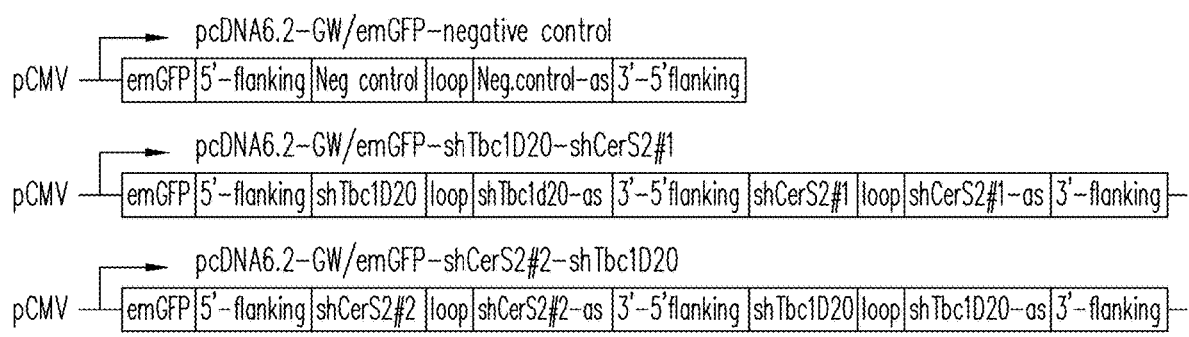

FIG. 7 shows the EFFECT OF COMBINED CERS2 AND TBC1D20 KNOCKDOWN ON PRODUCTIVITY OF CHO-mAB2 CELLS CHO-DG44 cells stably secreting the IgG antibody mAb2 were transfected with siRNAs against CERS2 and TBC1D20 in combination (siTbc1D20#1 and siCerS2#1). Specific productivity on days 3 and 4 was calculated and normalized to non-transfected control cells (mock). Combined knockdown of CERS2 and TBC1D20 resulted in improved specific productivity at day 3 and day 4 (n=3, error bars=SEM of triplicates).

FIG. 8 shows QUANTIFICATION OF STABLE GFP EXPRESSION IN ANTIBODY PRODUCING CHO CELLS BY FLOW CYTOMETRY CHO-DG44 cells stably secreting the IgG antibody mAb2 were stably transfected with a GFP-containing expression vector further encoding (as shown in panel A) a shRNA specific for ATF6B (pcDNA6.2-GW/emGFP-shATF6B #1 whose sequence structure is schematically represented in panel B), and (as show in panel C) a shRNA specific for CERS2 and for TBC1D20 (pcDNA6.2-GW/emGFP-shTBC1D20#1-shCERS2#1 or pcDNA6.2-GW/emGFP-shCERS2#2-shTBC1D20#1, whose sequence structures are schematically represented panel D). GFP-positive cells were enriched by FACS and living cells were analyzed by flow cytometry analysis after cultivation for 42 days after sorting (see panels A and C). As a negative control, untransfected cells without GFP expression were used (greyed out).

Figure 9A:
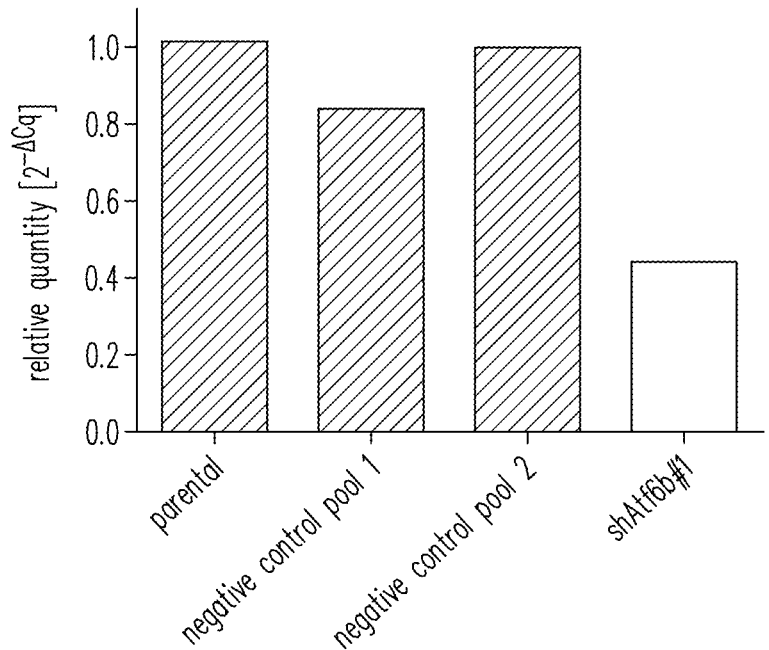
Figure 9B:
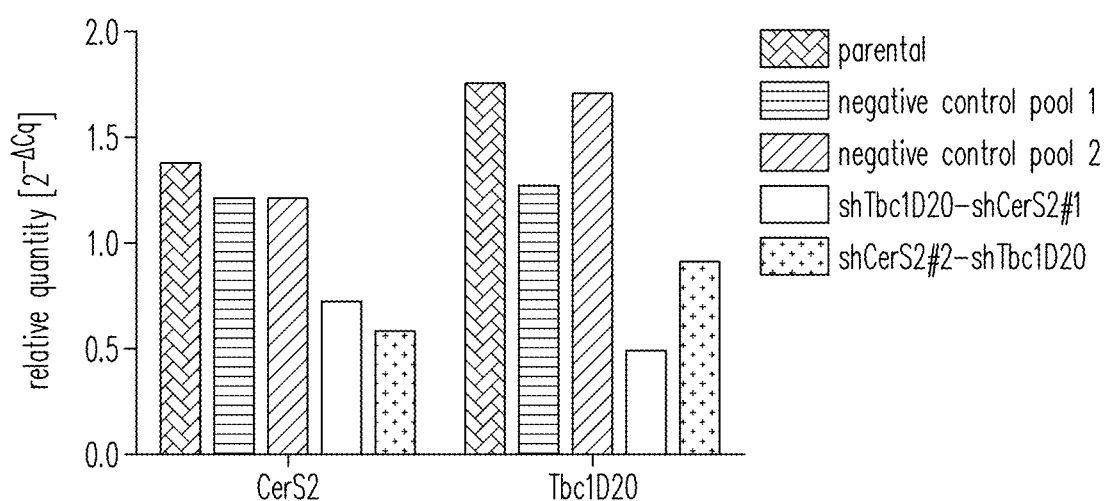

FIG. 9 shows QUANTIFICATION OF STABLE KNOCKDOWN IN ANTIBODY PRODUCING CHO CELLS BY QPCR CHO-DG44 cells stably secreting the IgG antibody mAb2 were stably transfected with a GFP-containing expression vector further encoding (as shown in panel A) a shRNA specific for ATF6B (shAtf6b #1) or (as shown in panel B) two combined shRNAs specific for CERS2 and TBC1D20 (shCerS2#1-shTbc1D20#1, shCerS2#2-shTbc1D20#1). GFP-positive cells were enriched by FACS sorting and RNA was extracted to measure levels of mRNA of ATF6B or CERS2 and TBC1D20, respectively, by qPCR analysis. Relative expression was calculated by normalizing to the reference gene beta actin.

Figure 10A:
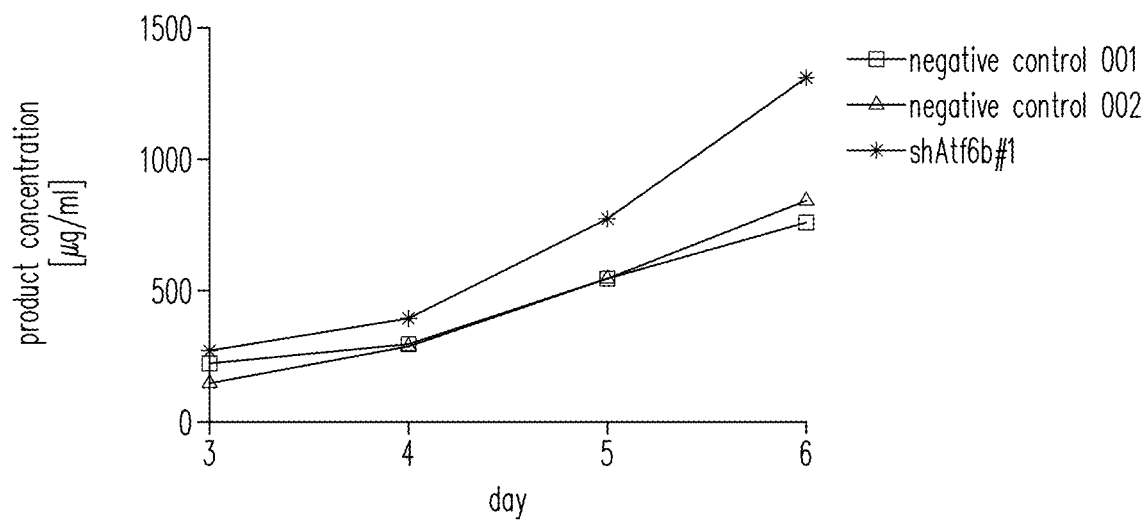
Figure 10B:
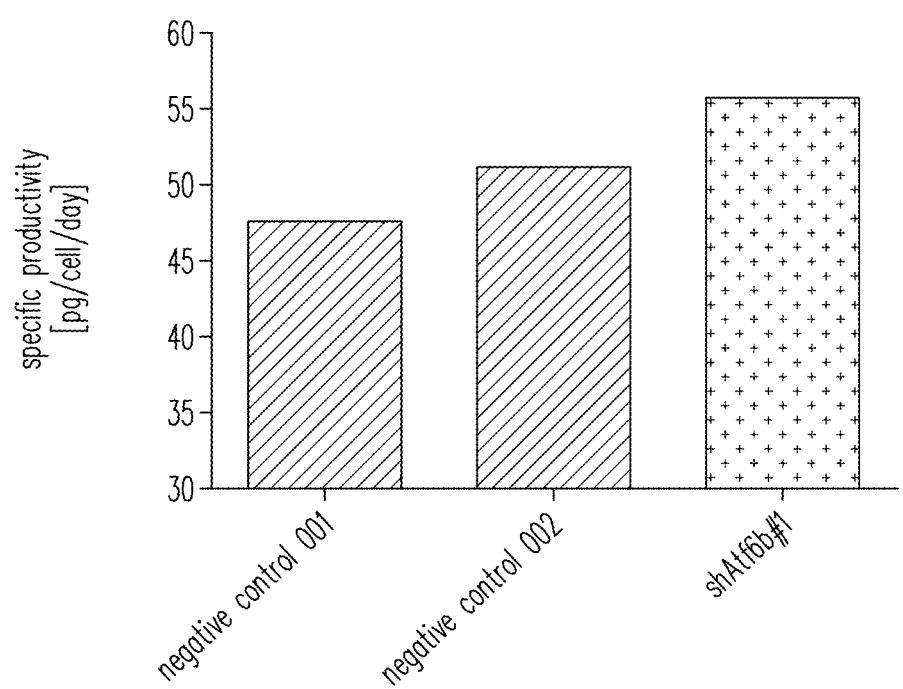
Figure 10C:
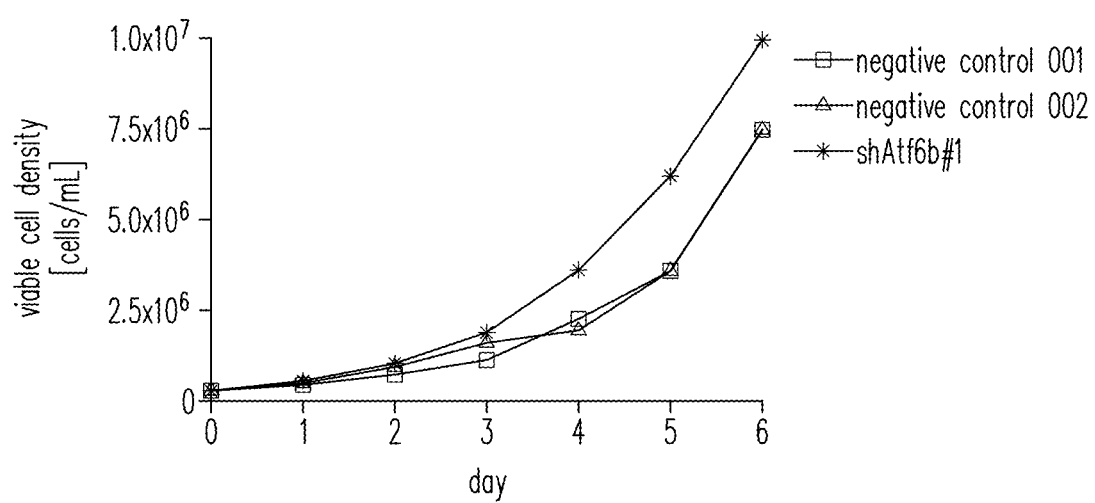

FIG. 10 shows the EFFECTS OF STABLE KNOCK-DOWN OF ATF6B IN FED-BATCH CELL CULTURE CHO-DG44 cells stably secreting the IgG antibody mAb2 were stably transfected with shRNAs against ATF6B (pcDNA6.2-GW/emGFP-shAtf6b #1) or a negative control sequence expression plasmid (pcDNA6.2-GW/emGFP-negative-control) and enriched for GFP positive cells by FACS sorting. Stable pools (one pool for shAtf6b #1 and two independent pools for the negative control plasmid) were grown in fed-batch cultures. Cell density and antibody concentration in the supernatant were determined on days 3-6 by cell counting with trypan blue exclusion and ELISA analysis, respectively, and specific productivity was calculated. The data for one representative experiment are shown for the product concentration (in panel A), the specific productivity at day 6 (in panel B), and the viable cell density (in panel C).

Figure 11A:
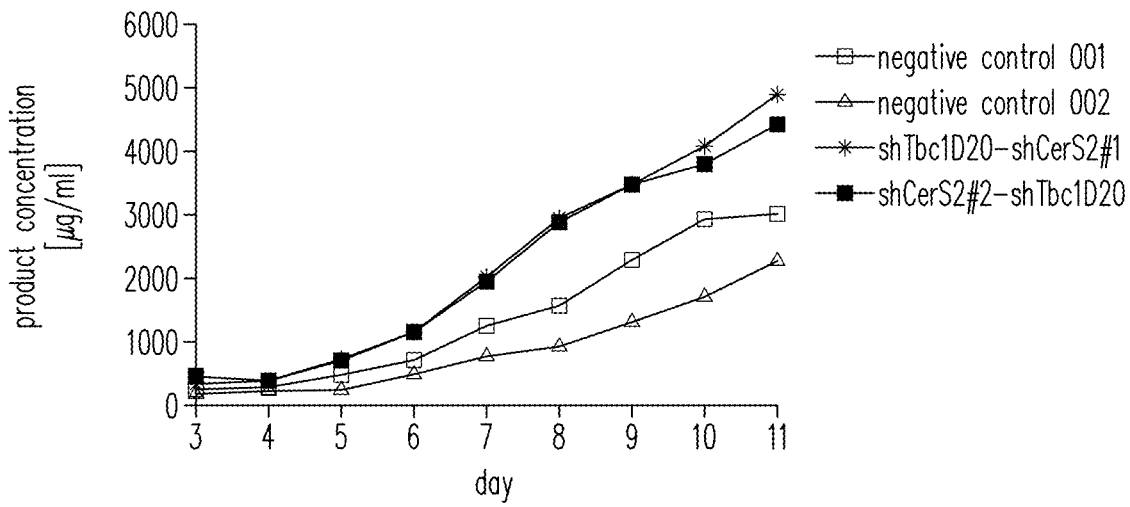
Figure 11B:
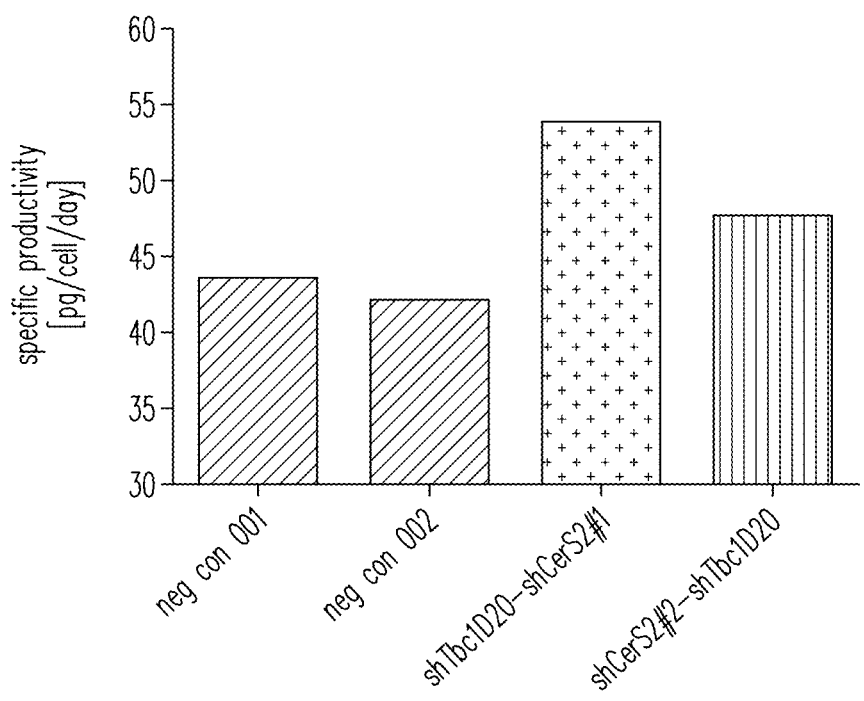
Figure 11C:
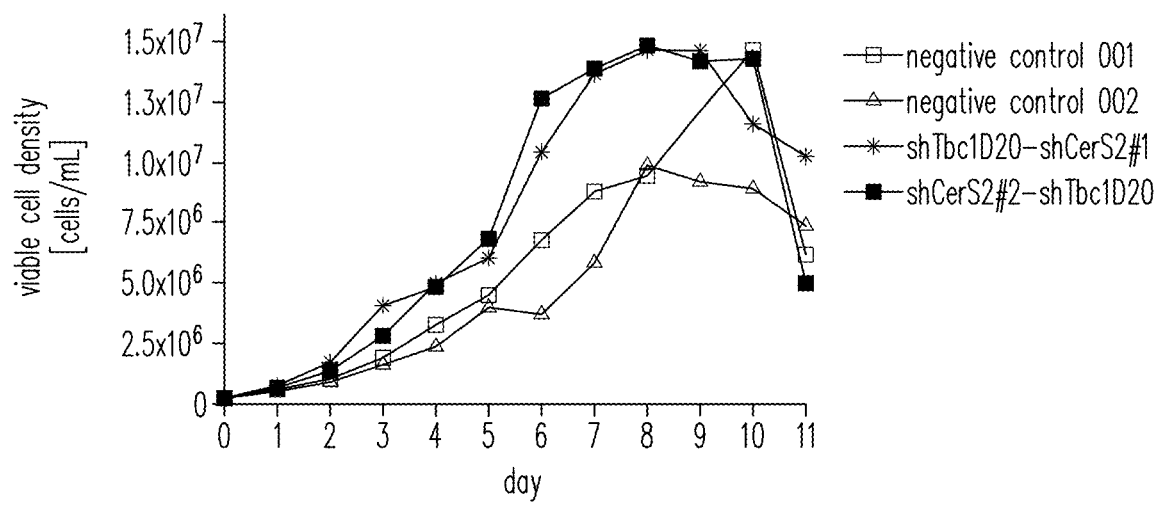

FIG. 11 shows the EFFECTS OF STABLE KNOCK-DOWN OF CERS2 AND TBC1D20 IN FED-BATCH CELL CULTURE CHO-DG44 cells stably secreting the IgG antibody mAb2 were stably transfected with expression vectors encoding for shRNAs specific for CERS2 and TBC1D20 (pcDNA6.2-GW/emGFP-shTbc1D20#1-shCerS2#1 and pcDNA6.2-GW/emGFP-shCerS2#2-shTbc1D20#1) or a negative control sequence (pcDNA6.2-GW/emGFP-negative-control) and enriched for GFP positive cells by FACS sorting. Stable pools (one pool for each of two independent shRNA combinations and 2 independent pools for the negative control plasmid) were grown in fed-batch cultures. Cell density and antibody concentration in the supernatant were determined on days 3-11 by cell counting with trypan blue exclusion and ELISA analysis, respectively, and specific productivity was calculated. The data for one representative experiment are shown for the product concentration (in panel A), the specific productivity at day 11 (in panel B) and the viable cell density (in panel C).

FIG. 12 shows the ANALYSIS OF ANTIBODY GLYCOSYLATION AND AGGREGATE FORMATION UNDER FED-BATCH CONDITIONS CHO-DG44 cells stably secreting the IgG antibody mAb2 were stably transfected with expression vectors expressing (in panels A, C) a shRNA specific for ATF6B (pcDNA6.2-GW/emGFP-shAtf6b #1) or (in panels B, D) shRNAs specific for CERS2 and TBC1D20 (pcDNA6.2-GW/emGFP-shTbc1D20#1-shCerS2#1 and pcDNA6.2-GW/emGFP-shCerS2#2-shTbc1D20#1). As a control the same antibody producing cells were transfected with a negative control sequence expression plasmid (pcDNA6.2-GW/emGFP-negative-control). (A, B) The composition of the Fc-glycosylation of the IgG antibody was analyzed after PNGaseF release and fluorescent labelling using microchip-based capillary electrophoresis (CE). The percentage of the glycolforms was calculated from the chromatographic peak areas and is shown for (in panel A) shATF6b expressing and (in panel B) shCERS2 and shTBC1D20 expressing cells. The glycans in the legend on the right hand side are listed inversely to the order in each bar, i.e., Man 5 at the bottom, UNK second from the bottom etc. Abbreviations: A2, biantennary; G, galactose; F, fucose; Man, mannose; UNK, unknown; asterisks indicate isoforms. (C) CHO-DG44 cells stably secreting the IgG antibody mAb2 and stably expressing shAtf6b #1, shAtf6b #2 or a negative control sequence were cultivated under fed-batch conditions for 7 days. The secreted antibody was purified from the supernatants and analyzed by HPLC and the absorption over time of the three samples analysed is shown in panel C. (D) CHO-mAb2 cells stably expressing shTbc1D20-shCerS2#1, shCerS #2-shTbc1D20 or a negative control sequence were cultivated under Fed-batch conditions for 11 days. The secreted antibody was purified from the supernatant and analyzed by HPLC and the absorption over time of the three samples analysed is shown in panel D.

Figure 13A:
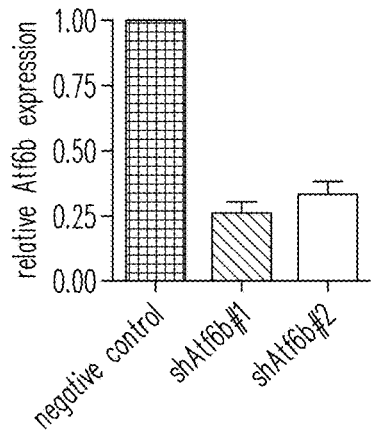
Figure 13B:
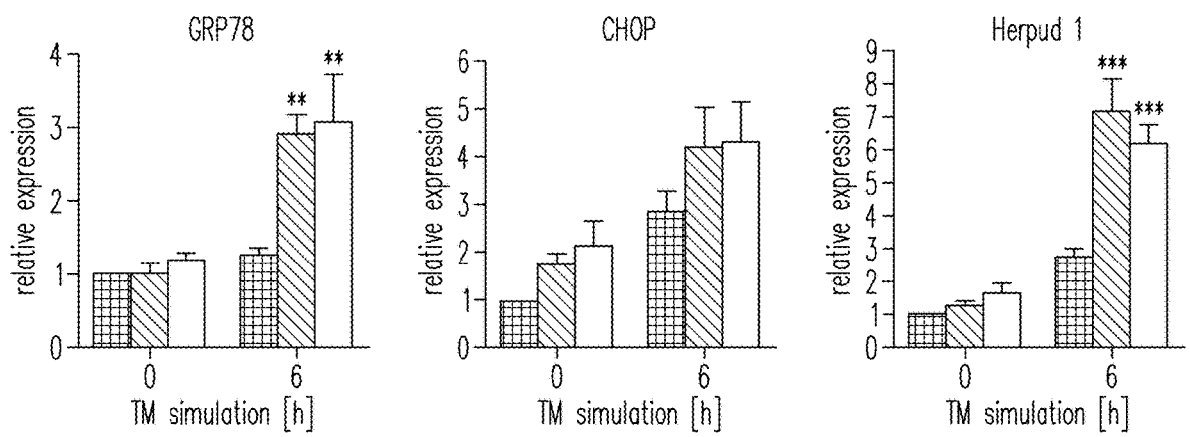
Figure 13C:
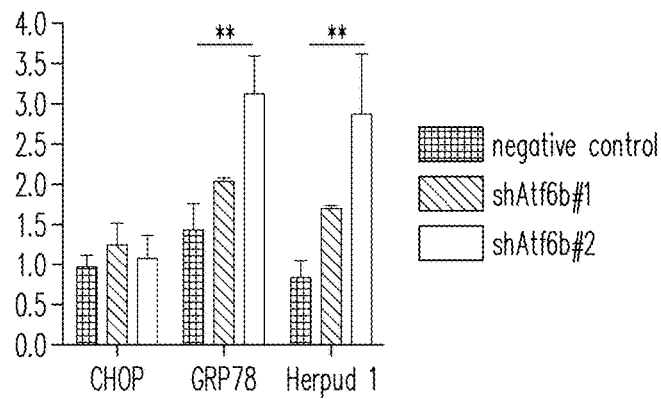

FIG. 13 shows the EFFECT OF ATF6B KNOCKDOWN ON THE EXPRESSION OF GRP78, CHOP AND HERPUD1 AFTER TUNICAMYCIN TREATMENT CHO-DG44 cells stably secreting the IgG antibody mAb2 were stably transfected with a plasmid encoding a GFP cassette plus a shRNA sequence comprising a nucleotide sequence specifically targeting ATF6B (pcDNA6.2-GW/emGFP-shAtf6b #1 or pcDNA6.2-GW/emGFP-shAtf6b #2), or a negative control construct. Panel A is a bar graph showing the mRNA level of Atf6b as quantified by qPCR. Values are given relative to control. Panel B provides bar graphs showing the mRNA levels of GRP78, Herpud1 and CHOP in untreated cells and tunicamycin (TM) treated cells (2.5 µg/mL TM for 6 hours) as quantified by qPCR and shown relative to negative control cells at time point 0. All data are shown as mean+/−SEM (n=3, p<0.01, *p<0.001, One Way Anova and Tukeys Multiple Comparison Test), representing negative control (black bar, left); shAtf6b #1 (grey bar, middle); and shAtf6b #2 (white bar, right) as also shown in the legend of FIG. 13C. (C) CHO-DG44 cells stably secreting the IgG antibody mAb2 and stably expressing shAtf6b #1, shAtf6b #2 or a negative control sequence were cultivated under fed-batch conditions for 5 days. At day 5 the mRNA levels of GRP78/BiP, Herpud1 and CHOP were quantified by qPCR (as shown in panel C). All data are shown as mean+/−SEM (N=3, **p<0.01, Two Way Anova and Bonferroni posttest).

FIG. 14 shows the EFFECT OF CERS2 AND TBC1D20 KNOCKDOWN ON RAB1 ACTIVITY AND CERAMIDE COMPOSITION (A) CHO-DG44 cells stably secreting the IgG antibody mAb2 were transfected with a non-targeting siRNA (NT) as a control, siTbc1D20 or siCerS2/siTbc1D20. Three days post transfection active Rab1 was detected in cell homogenates using a pull-down assay with a p115-GST fusion protein (as shown in panel A). Bound Rab1 was detected by immunoblotting with an anti-Rab1 antibody. An anti-GST antibody was used to detect the p115-GST protein as loading control. Detection of actin in the lysates verifies equal loading of protein (input). Panel B is a bar graph showing that the band intensity of active Rab1 was quantified using Image J software. (n=3, mean±SEM). Panel C shows that knockdown efficiency was confirmed by qPCR at day 2 post transfection (n=3, mean±SEM). (D) Three days after transfection with NT siRNA control, siCerS2 or siTbc1D20/siCerS2, cells were homogenized and ceramide synthase activity was measured by adding either C16-CoA or C24-CoA as substrates together with NBD-labeled sphinganine. The products C16-dihydroceramide and C24-dihydroceramide were separated by thin layer chromatography and detected using a fluorescence scanner (as shown in panel D). Panel E is a bar graph showing band intensities of C16- and C24-dihydroceramides as quantified using Image J software.

The intensities of both products in cells transfected with the siRNA control were set to 100% (n=3, mean±SEM). Panel F is a bar graph showing that the efficiency of siRNA-mediated knockdown was confirmed by qPCR (n=2, mean±SEM).

Figure 15A:
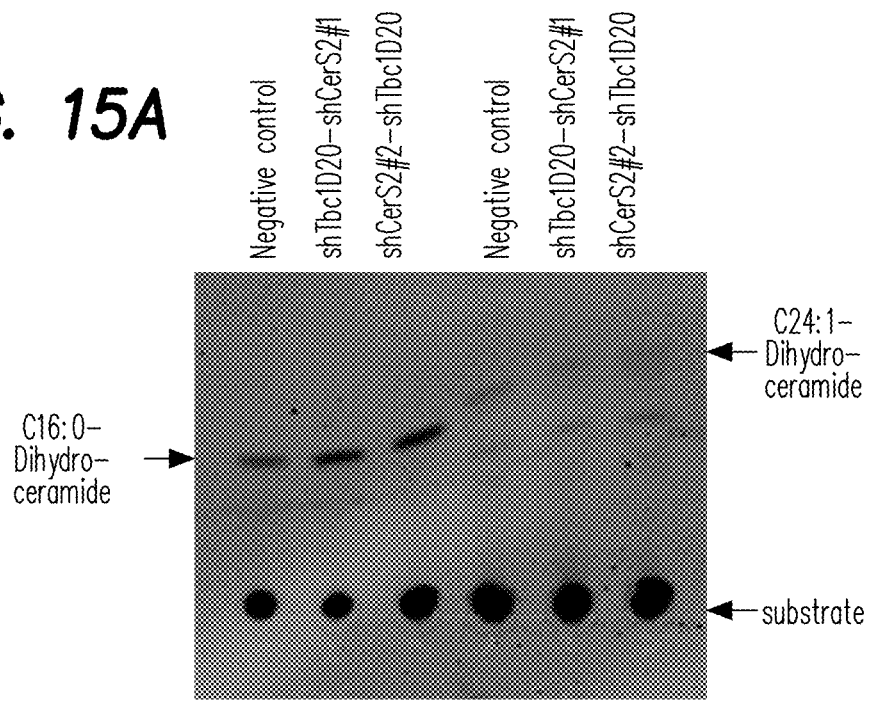
Figure 15B:
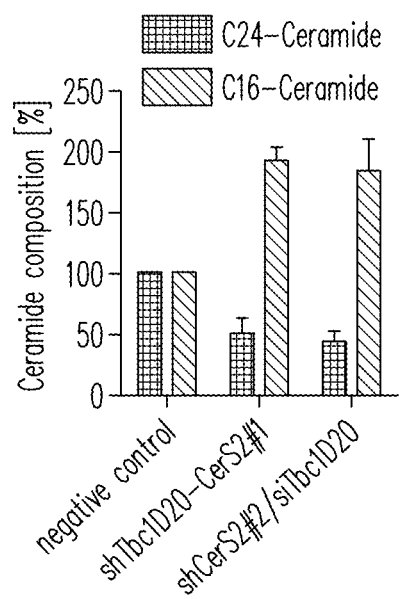

FIG. 15 shows the EFFECTS OF STABLE KNOCKDOWN ON DOWNSTREAM TARGETS (A) CHO-DG44 cells stably secreting the IgG antibody mAb2 were stably transfected with expression vectors encoding for shRNAs specific for CERS2 and TBC1D20 (pcDNA6.2-GW/emGFP-shTbc1D20#1-shCerS2#1 and pcDNA6.2-GW/emGFP-shCerS2#2-shTbc1D20#1) or a negative control sequence (pcDNA6.2-GW/emGFP-negative-control) and were analysed in a fluorescent CerS assay to detect ceramide synthase activity in CHO-mAb2 cell pools. In distinct reactions, either C16-CoA or C24-CoA served as substrates together with NBD-labeled sphinganine. The products C16-ceramide and C24-ceramide were separated by thin layer chromatography and detected using a fluorescence scanner (as shown in panel A). Panel B shows the band intensities of C16- and C24-ceramides as quantified using the Image J software. The intensities of both products in the negative control pool were set to 100%.

DETAILED DESCRIPTION OF THE INVENTION

Definitions

The general embodiments "comprising" or "comprised" encompass the more specific embodiment "consisting of". Furthermore, singular and plural forms are not used in a limiting way. As used herein, the singular forms "a", "an" and "the" designate both the singular and the plural, unless expressly stated to designate the singular only.

The term "ribonucleic acid", "RNA" or "RNA oligonucleotide" as used herein describes a molecule consisting of a sequence of nucleotides, which are built of a nucleobase, a ribose sugar, and a phosphate group. RNAs are usually single stranded molecules and can exert various functions. The term ribonucleic acid specifically comprises messenger RNA (mRNA), transfer RNA (tRNA), ribosomal RNA (rRNA), short interfering RNA (siRNA), small hairpin RNA (shRNA) and micro RNA (miRNA), each of which plays a specific role in biological cells. It includes small non-coding RNAs, such as microRNAs (miRNA), short interfering RNAs (siRNA), small hairpin RNA (shRNA), and Piwi-interacting RNAs (piRNA). The term "non-coding" means that the RNA molecule is not translated into an amino acid sequence.

The term "RNA interference" (RNAi) refers to sequence-specific or gene-specific suppression of gene expression (protein synthesis), without generalized suppression of protein synthesis. RNAi may involve degradation of messenger RNA (mRNA) by an RNA-induced silencing complex (RISC), preventing translation of the transcribed mRNA. The suppression of gene expression caused by RNAi may be transient or it may be more stable, even permanent. RNAi may be mediated by siRNA or shRNA. Preferably the RNAi according to the invention is gene-specific (only one gene is targeted). RNAi is considered to be gene-specific or specific for its target gene, if the RNA oligonucleotide comprises a sequence which has complete sequence complementarity with the target gene (i.e., perfect base pairing between the antisense strand of the RNA duplex of the small interfering RNA and the target mRNA). Gene-specific RNAi may be mediated by siRNA or shRNA. In a preferred embodiment, the RNAi is mediated by siRNA or shRNA. In another preferred embodiment, the RNAi is not mediated by miRNA.

The terms "microRNA" or "miRNA" are used interchangeably herein. microRNAs are small, about 22 nucleotide-long (typically between 19 and 25 nucleotides in length) non-coding single stranded RNAs. miRNAs typically target more than one gene. microRNAs are encoded in the genome of eukaryotic cells and are typically transcribed by RNA Polymerase III as long primary transcripts that are then processed in several steps first into ~70nt-long hairpin-loop structures and subsequently into the ~22nt RNA duplex. The active mature strand is then loaded into the RNA-induced silencing complex (RISC) in order to block translation of target proteins or degradation of their respective mRNAs. Targeting with miRNAs allows for mismatches and mRNA translational repression is mediated by incomplete complementarity (i.e., imperfect base paring between the antisense strand of the RNA duplex of the small interfering RNA and the target mRNA), while siRNA and shRNA are specific for their targets due to complete sequence complementarity (i.e., perfect base pairing between the antisense strand of the RNA duplex of the small interfering RNA and the target mRNA). Typically, miRNAs bind in the 3'untranslated region (3'UTR) and are not gene-specific, but target multiple mRNAs. The term "microRNA" as used herein relates to endogenous genomic mammalian miRNAs, such as human miRNAs. The prefix "hsa" indicates, e.g., the human origin of a microRNA. They may be introduced into a mammalian host cell using an expression vector comprising genomic microRNA sequence(s) for transient or stable expression of miRNA in the mammalian host cell. Means for cloning genomic microRNA into an expression vector are known in the art. They include, cloning genomic miRNA sequences with approximately 300 bp flanking regions into a mammalian expression vector, such as pBIP-1, operably linked to a promoter. Alternatively one or more microRNAs may be cloned as polynucleotides encoding engineered pre-miRNA sequences (i.e., short hairpins) into a mammalian expression vector. For example, a mature miRNA sequence may be cloned into a given sequence encoding an optimized hairpin loop sequence and 3' and 5' flanking regions, such as derived from the murine miRNA mir-155 (Lagos-Quintana et al., 2002. Curr Biol. 30; 12(9):735-9). A DNA oligonucleotide is designed, which encodes the miRNA sequence, the mentioned loop and the antisense sequence of the respective mature miRNA with a two nucleotide depletion to generate an internal loop in the hairpin stem. Furthermore, overhangs are added for cloning at both ends to fuse the DNA oligonucleotide to the 3' and 5' flanking regions. miRNAs as used herein further comprise non-canonical miRNAs. These RNAs can be derived from 'housekeeping' non-coding RNAs (ncRNA) including ribosomal RNA (rRNA) or transfer RNA (tRNA) and function in a miRNA-like manner. These RNAs can also originate from mammalian mitochondrial ncRNAs and are termed mitochondrial genome-encoded small RNAs (mitosRNAs).

As used herein, the terms "small interfering" or "short interfering RNA" or "siRNA" refer to an RNA duplex of nucleotides that is targeted to a desired gene and is capable of inhibiting the expression of a gene with which it shares homology. It is formed from long double stranded RNA (dsRNA) or shRNA. The RNA duplex typically comprises two complementary single-stranded RNAs of 19, 20, 21, 22, 23, 24, 25, 26, 27, 28 or 29 nucleotides that form 17, 18, 19, 20, 21, 22, 23, 24, 25, 26 or 27 base pairs and possess 3' overhangs of two nucleotides, preferably the RNA duplex comprises two complementary single stranded RNAs of 19-27 nucleotides that form 17-25 base pairs and possess 3' overhangs of two nucleotides. siRNA is "targeted" to a gene, wherein the nucleotide sequence of the duplex portion of the siRNA is complementary to a nucleotide sequence of the mRNA of the targeted gene. The siRNA or a precursor thereof is always exogenously introduced into the cell, e.g., directly or by transfection of a vector having a sequence encoding said siRNA, and the endogenous miRNA pathway is harnessed for correct processing of siRNA and cleavage or degradation of the target mRNA. The duplex RNA can be expressed in a cell from a single construct.

As used herein, the term "shRNA" (small hairpin RNA) refers to an RNA duplex wherein a portion of the siRNA is part of a hairpin structure (shRNA). The shRNA can be processed intracellularly into a functional siRNA. In addition to the duplex portion, the hairpin structure may contain a loop portion positioned between the two sequences that form the duplex. The loop can vary in length. In some embodiments the loop is 4, 5, 6, 7, 8, 9, 10, 11, 12, 13 or 14 nucleotides in length. The hairpin structure can also contain 3' or 5' overhang portions. In some aspects, the overhang is a 3' or a 5' overhang of 0, 1, 2, 3, 4 or 5 nucleotides in length. In one aspect of this invention, a nucleotide sequence comprised in the vector serves as a template for the expression of a small hairpin RNA, comprising a sense region, a loop region and an antisense region. Following expression the sense and antisense regions form a duplex. shRNA is always exogenously introduced, e.g., by transfection of a vector having a sequence encoding said shRNA, and the endogenous miRNA pathway is harnessed for correct processing of the siRNA and cleavage or degradation of the target mRNA. Use of a vector having a sequence encoding a shRNA has the advantage over use of chemically synthesized siRNA in that the suppression of the target gene is typically long-term and stable.

Typically siRNA and shRNA mediate mRNA repression by complete sequence complementarity (i.e., perfect base paring between the antisense strand of the RNA duplex of the small interfering RNA and the target mRNA) and are therefore specific for their target. The antisense strand of the RNA duplex may also be referred to as active strand of the RNA duplex. Complete sequence complementarity of perfect base paring as used herein means that the antisense strand of the RNA duplex of the small interfering RNA has at least 89% sequence identity with the target mRNA for at least 15 continuous nucleotides, at least 16 continuous nucleotides, at least 17 continuous nucleotides, at least 18 continuous nucleotides and preferably at least 19 continuous nucleotides, or preferably at least 93% sequence identity with the target mRNA for at least 15 continuous nucleotides, at least 16 continuous nucleotides, at least 17 continuous nucleotides, at least 18 continuous nucleotides and preferably at least 19 continuous nucleotides. More preferably the antisense strand of the RNA duplex of the small interfering RNA has 100% sequence identity with the target mRNA for at least 15 continuous nucleotides, at least 16 continuous nucleotides, at least 17 continuous nucleotides, at least 18 continuous nucleotides and preferably at least 19 continuous nucleotides.

The term "ATF6B" as used herein refers to the protein Activating Transcription Factor 6 Beta. It is also known as CREBL1, CAMP Response Element-Binding Protein-Related Protein, CAMP Responsive Element Binding Protein-Like 1, CAMP-Dependent Transcription Factor ATF-6 Beta, CAMP-Responsive Element-Binding Protein-Like 1, Protein G13 CREB-RP, G13, Cyclic AMP-Dependent Transcription Factor ATF-6 Beta, Creb-Related Protein, ATF6-Beta. External Ids for Atf6b are: HGNC: 2349; Entrez Gene: 1388; Ensembl: ENSG00000213676; OMIM: 600984; UniProtKB: Q99941 (http://www.genecards.org/cgi in/carddisp.pl?gene=ATF6B&keywords=ATF6B). It comprises proteins having the amino acid sequence of SEQ ID NO: 6 or an amino acid sequence having at least 80% sequence identity with SEQ ID NO:6.

The term "CERS2" as used herein refers to the protein Ceraminde Synthase 2. It is also known as LASS2, Longevity Assurance (LAG1, S. cerevisiae) Homolog 2, Tumor Metastasis-Suppressor Gene 1 Protein, LAG1 Homolog, Ceramide Synthase 2, SP260, TMSG1, LAG1 Longevity Assurance Homolog 2 (S. cerevisiae), LAG1 Longevity Assurance Homolog 2, LAG1 Longevity Assurance 2, L3. External Ids for CerS2 are: HGNC: 14076; Entrez Gene: 29956; Ensembl: ENSG00000143418; OMIM: 606920; UniProtKB: Q96G23 (http://www.genecards.org/cgi-bin/carddisp.pl?gene=CERS2). It comprises proteins having the amino acid sequence of SEQ ID NO: 5 or an amino acid sequence having at least 80% sequence identity with SEQ ID NO:5.

The term "TBC1D20" as used herein refers to TBC1 Domain Family Member 20. It is also known as C20orf140, WARBM4 and Chromosome 20 Open Reading Frame 140. External Ids for Tbc1d20 are: HGNC: 16133; Entrez Gene: 128637; Ensembl: ENSG00000125875; OMIM: 611663; UniProtKB: Q96BZ9 (http://www.genecards.org/cgi-bin/carddisp.pl?gene=TBC1D20). It comprises proteins having the amino acid sequence of SEQ ID NO: 4 or an amino acid sequence having at least 80% sequence identity with SEQ ID NO: 4.

As used herein, an RNA oligonucleotide that inhibits the expression of TBC1D20, CERS2 or ATF6B by RNAi specifically targets the RNA encoding TBC1D20, CERS2 or ATF6B, respectively. In a preferred embodiment, the RNA oligonucleotide excludes miRNA.

The term "knockdown" or "knockdown technology" refers to a technique of gene silencing in which the expression of a target gene or gene of interest is reduced as compared to the gene expression prior to the introduction of an RNA oligonucleotide that inhibits expression of a target gene by RNA-interference, such as by using siRNA or shRNA, which can lead to the inhibition of production of the target gene product. "Double knockdown" is the knockdown of two genes.

A gene may also be modified by deleting the gene using "knockout" technology. The term "knockout" refers to cells, which have been genetically modified so that the expression of host cell proteins AFT6B or the combination of host cell proteins TBC1D20 and CERS2 is/are inhibited and the respective host cell protein is not produced (reduced by 100%). This may be achieved using various technologies, which are known in the art, including CRISPR-Cas9 or Zinc finger nuclease technology.

Alternatively, the gene may be altered to inhibit the expression of its protein by introduction of a mutation in the gene. The gene mutation may be a deletion, addition or substitution in the coding region or in the promoter or regulatory region of the gene. This gene mutation may be either in one or both alleles of a gene.

The term "reduction", "reduced" or "reduce", as used herein, generally means a decrease by at least 10% as compared to a reference level, for example a decrease by at least about 20%, or at least about 30%, or at least about 40%, or at least about 50%, or at least about 60%, or at least about 70%, or at least about 75%, or at least about 80%, or at least about 90% or up to and including a 100% decrease, or any integer decrease between 10-100% as compared to a control mammalian cell. The expression of the host cell proteins TBC1D20 and CERS2, or of the host cell protein ATF6B, is preferably reduced by at least 30%, at least 40%, at least 50%, at least 75%, or 100%, compared to a control mammalian cell.

The term "enhancement", "enhanced", "enhanced", "increase" or "increased", as used herein, generally means an increase by at least 10% as compared to a control cell, for example an increase by at least about 20%, or at least about 30%, or at least about 40%, or at least about 50%, or at least about 75%, or at least about 80%, or at least about 90%, or at least about 100%, or at least about 200%, or at least about 300%, or any integer decrease between 10-300% as compared to a control cell.

As used herein, a "control cell" or "control mammalian cell" is a cell which is the same as the cell to which it is compared to, except that it does not have reduced expression of the host cell proteins TBC1D20 and CERS2 or ATF6B. The control mammalian cell may be produced by a method of the present invention, but omitting the step of reducing the expression of host cell proteins TBC1D20 and CERS2, or of the host cell protein ATF6B. In particular, the control mammalian cell lacks any a genetic modification that inhibits expression of TBC1D20 and CERS2, or ATF6B and lacks any transfected RNA oligonucleotide that inhibits the genes Tbc1d20 and Cers2, or Atf6b, by RNA-interference.

The term "derivative" or "homologue" as used in the present invention means a polypeptide molecule or a nucleic acid molecule, which is at least 70% identical in sequence with the original sequence or its complementary sequence. Preferably, the polypeptide molecule or nucleic acid molecule is at least 80% identical in sequence with the original sequence or its complementary sequence. More preferably, the polypeptide molecule or nucleic acid molecule is at least 90% identical in sequence with the original sequence or its complementary sequence. Still more preferably, the polypeptide molecule or a nucleic acid molecule is at least 95% identical in sequence with the original sequence or its complementary sequence. Most preferably the polypeptide molecule or a nucleic acid molecule is at least 98% identical in sequence with the original sequence or its complementary sequence. A homologous protein further displays the same or a similar protein activity as the original sequence.

Sequence differences may be based on differences in homologous sequences from different organisms or may be naturally occurring allelic variations. They might also be based on targeted modification of sequences by substitution, insertion or deletion of one or more nucleotides or amino acids, preferably 1, 2, 3, 4, 5, 7, 8, 9 or 10. Deletion, insertion or substitution mutants may be generated using site-specific mutagenesis and/or PCR-based mutagenesis techniques.

The term "host cells" as used herein are mammalian cells lines suitable for the production of a secreted recombinant therapeutic protein and may hence also be referred to as "mammalian cells". Preferred mammalian cells according to the invention are rodent cells such as hamster cells. The mammalian cells are isolated cells or cell lines. The mammalian cells are preferably transformed and/or immortalized cell lines. They are adapted to serial passages in cell culture and do not include primary non-transformed cells or cells that are part of an organ structure. Preferred mammalian cells are BHK21, BHK TK⁻, CHO, CHO-K1 (such as CHO-DUKX, CHO-DUKX B1) and CHO-DG44 cells or the derivatives/progenies of any of such cell line. Particularly preferred are CHO-DG44, CHO-K1 and BHK21, and even more preferred are CHO-DG44 and CHO-K1 cells. Most preferred are CHO-DG44 cells. Glutamine synthetase (GS)-deficient derivatives of the mammalian cell, particularly of the CHO-DG44 and CHO-K1 cell are also encompassed. The mammalian cell may further comprise one or more expression cassette(s) encoding a recombinant secreted therapeutic protein. The host cells may also be murine cells such as murine myeloma cells, such as NS0 and Sp2/0 cells or the derivatives/progenies of any of such cell line. Non-limiting examples of mammalian cells which can be used in the meaning of this invention are also summarized in Table 1. However, derivatives/progenies of those cells, other mammalian cells, including but not limited to human, mice, rat, monkey, and rodent cell lines, can also be used in the present invention, particularly for the production of biopharmaceutical proteins.

TABLE 1

Mammalian production cell lines

| Cell line | Order Number |
|---|---|
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX (= CHO duk⁻, CHO/dhfr⁻) | ATCC CRL-9096 |
| CHO-DUKX B11 | ATCC CRL-9010 |
| CHO-DG44 | Urlaub G, et al., 1983. Cell. 33:405-412. |
| CHO Pro-5 | ATCC CRL-1781 |
| V79 | ATCC CCC-93 |
| B14AF28-G3 | ATCC CCL-14 |
| HEK 293 | ATCC CRL-1573 |
| COS-7 | ATCC CRL-1651 |
| U266 | ATCC TIB-196 |
| HuNS1 | ATCC CRL-8644 |
| CHL | ECACC No. 87111906 |
| CAP[1] | Wölfel J, et al., 2011. BMC Proc. 5(Suppl 8):P133. |
| PER.C6 ® | Pau et al., 2001. Vaccines. 19:2716-2721. |
| H4-II-E | ATCC CRL-1548 ECACC No.87031301 Reuber, 1961. J. Natl. Cancer Inst. 26:891-899. Pitot HC, et al., 1964. Natl. Cancer Inst. Monogr. 13:229-245. |
| H4-II-E-C3 | ATCC CRL-1600 |
| H4TG | ATCC CRL-1578 |
| H4-II-E | DSM ACC3129 |
| H4-II-Es | DSM ACC3130 |

[1]CAP (CEVEC's Amniocyte Production) cells are an immortalized cell line based on primary human amniocytes. They were generated by transfection of these primary cells with a vector containing the functions E1 and pIX of adenovirus 5. CAP cells allow for competitive stable production of recombinant proteins with excellent biologic activity and therapeutic efficacy as a result of authentic human posttranslational modification.

Host cells are most preferred, when being established, adapted, and completely cultivated under serum free conditions, and optionally in media, which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-

Invitrogen), serum-free CHO Medium (Sigma), and protein-free CHO Medium (Sigma) are exemplary appropriate nutrient solutions. Any of the media may be supplemented as necessary with a variety of compounds, non-limiting examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics and trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing the selectable gene a suitable selection agent is added to the culture medium.

The term "protein" is used interchangeably with "amino acid residue sequences" or "polypeptide" and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with the same properties.

The term "polypeptide" means a sequence with more than 10 amino acids and the term "peptide" means sequences with up to 10 amino acids in length. However, the terms may be used interchangeably.

The present invention is suitable to generate host cells for the production of biopharmaceutical or diagnostic polypeptides/proteins. The invention is particularly suitable for the high-yield expression of a large number of different genes of interest by cells showing enhanced cell productivity.

"Recombinant secreted therapeutic protein" refers to a secreted protein of interest suitable for diagnostic or therapeutic use, preferably for therapeutic use encoded by a polynucleotide sequence of any length that has been introduced into a host cell. The selected sequence encoding the protein can be full length or a truncated gene, a fusion or tagged gene, and can be a cDNA, a genomic DNA, or a DNA fragment, preferably a cDNA. It can be the native sequence, i.e. naturally occurring form(s), or can be mutated or otherwise modified as desired. These modifications include codon optimizations to optimize codon usage in the selected host cell, humanization, fusion or tagging. A "recombinant" protein is a protein expressed from a heterologous sequence.

The term "host cell protein" generally relates to all proteins endogenous to the host cell, but is used herein as specifically relating to the host cell protein ATF6B or to the two host cell proteins TBC1D20 and CERS2.

The term "producing" or "highly producing", "production", "production and/or secretion", "producing" or "production cell" as used herein relates to the production of the recombinant secreted therapeutic protein. An "increased production and/or secretion" relates to the expression of the recombinant secreted therapeutic protein and means an increase in specific productivity, increased titer or both. Preferably, the titer or the specific productivity and the titer are increased. Increased titer as used herein relates to an increased concentration in the same volume, i.e., an increase in total yield. The produced recombinant secreted therapeutic protein may be, for example, an antibody, preferably a monoclonal antibody, a bispecific antibody or a fragment thereof, or a fusion protein, preferably a Fc-fusion protein.

As used herein, the term "expression cassette" refers to the part of a vector comprising one or more genes encoding for a protein (recombinant secreted therapeutic protein) and the sequences controlling their expression. Thus it comprises a promoter sequence, an open reading frame and a 3' untranslated region, typically containing a polyadenylation site. Preferably the vector is an expression vector comprising one or more gene encoding for the recombinant secreted therapeutic protein. It may be part of a vector, typically an expression vector, including a plasmid or a viral vector. It may also be integrated in a chromosome by random or targeted integration, such as by homologous recombination. An expression cassette is prepared using cloning techniques and does therefore not refer to a natural occurring gene structure.

A "vector" is a nucleic acid that can be used to introduce another nucleic acid (or "construct") linked to it into a cell. One type of vector is a "plasmid", which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) integrate into the genome of a host cell upon introduction into the host cell and culturing under selective pressure, and thereby are replicated along with the host genome. A vector can be used to direct the expression of a chosen polynucleotide in a cell.

The term "expression vector" means a nucleic acid that has the ability confer expression of a nucleic acid fragment to which it is operably linked in a cell. As used herein, an expression vector may be for example a plasmid, a cosmid, virus sub-genomic or genomic fragment, or other nucleic acid capable of maintaining and/or replicating heterologous DNA in an expressible format in a mammalian cell.

The term "antibody" refers to a protein consisting of one or more polypeptides substantially encoded by immunoglobulin genes. The recognized immunoglobulin genes include the kappa, lambda, alpha, gamma, delta, epsilon and mu constant regions genes as well as the myriad immunoglobulin variable region genes. As used herein, the term "antibody" includes a polyclonal, monoclonal, bi-specific, multi-specific, human, humanized, or chimeric antibody. The terms "antibody" and "immunoglobulin" are used interchangeably and are used to denote, without being limited thereto, glycoproteins having the structural characteristics noted above for immunoglobulins.

The term "antibody" is used herein in its broadest sense and encompasses monoclonal antibodies (including full length monoclonal antibodies), polyclonal antibodies, chimeric antibodies, humanized antibodies, human antibodies, multispecific antibodies (e.g. bispecific antibodies), single domain antibodies, and antibody fragments (such as Fv, Fab, Fab', F(ab)2 or other antigen-binding subsequences of antibodies). The term "antibody" also encompasses antibody conjugates and fusion antibodies. Bispecific antibodies include BITE® (Bispecific T-cell Engager) and DART®

(Dual-Affinity Re-Targeting) antibodies. Single domain antibodies include camelids antibodies. Full length "antibodies" or "immunoglobulins" are generally heterotetrameric glycoproteins of about 150 kDa, composed of two identical light and two identical heavy chains. Each light chain is linked to a heavy chain by one covalent disulphide bond, while the number of disulphide linkages varies between the heavy chains of different immunoglobulin isotypes. Each heavy and light chain also has regularly spaced intrachain disulphide bridges. Each heavy chain has an amino terminal variable domain (VH) followed by three carboxy terminal constant domains (CH). Each light chain has a variable N-terminal domain (VL) and a single C-terminal constant domain (CL). The term "antibody" further refers to a type of antibody comprising a plurality of individual antibodies having the same specificity (variable domain) and having the same constant domains.

The term "monoclonal antibody" (mAb) as used herein refers to an antibody obtained from a population of substantially homogeneous antibodies based on the amino acid sequence. Monoclonal antibodies are highly specific, being directed against a single antigenic site. Furthermore, in contrast to conventional (polyclonal) antibody preparations, which typically include different antibodies directed against different determinants (epitopes), each mAb is directed against a single determinant on the antigen. In addition to their specificity, the mAbs are advantageous in that they can be synthesized by cell culture (hybridomas, recombinant cells or the like) uncontaminated by other immunoglobulins. The mAbs herein include chimeric, humanized and human antibodies.

"Chimeric antibodies" are antibodies, wherein light and/or heavy chain genes have been constructed, typically by genetic engineering, from immunoglobulin variable and constant regions of different species, such as mouse and human. Or alternatively, whose heavy chain genes are belonging to a particular antibody class or subclass while the remainder of the chain is from another antibody class or subclass of the same or another species. Also covered are fragments of such antibodies, preferably fragments that contain or are modified to contain at least one CH2 domain. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant or effector domain from a human antibody (e.g. ATCC Accession No. CRL 9688 secretes an anti-Tac chimeric antibody), although other mammalian species may be used.

The term "humanized antibodies" as used herein refers to specific chimeric antibodies, immunoglobulin chains or fragments thereof (such as Fv, Fab, Fab', F(ab)2 or other antigen-binding subsequences of antibodies), which contain minimal sequence derived from non-human immunoglobulin. Humanized antibodies comprise a human framework region and one or more CDRs from a non-human (usually a mouse or rat) antibody. Preferably they contain or are modified to contain at least the portion of the CH2 domain of the heavy chain immunoglobulin constant region comprising the N-linked glycosylation site. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity and capacity. Adjustments in framework amino acids might be required to keep antigen binding specificity, affinity and or structure of domain. In some instances, Fv framework residues of the human immunoglobulin are replaced by the corresponding non-human residues. Furthermore, humanized antibodies can comprise residues which are found neither in the recipient antibody nor in the imported CDR or framework sequences. These modifications are made to further refine and maximize antibody performance. In general, the humanized antibody will comprise at least one, and typically two, variable domains, in which all or substantially all off the CDR regions correspond to those of a non-human immunoglobulin and all or substantially all of the framework regions are those of a human immunoglobulin consensus sequence. Preferably, the humanized antibody also comprises at least a portion of an immunoglobulin constant region, typically that of a human immunoglobulin.

The term "CH2 domain" according to the present invention is meant to describe the CH2 domain of the heavy chain immunoglobulin constant region comprising the N-linked glycosylation site. In defining an immunoglobulin CH2 domain reference is made to immunoglobulins in general and in particular to the domain structure of immunoglobulins as applied to human IgG1 by Kabat, E. A. (Kabat E A, 1988. *J. Immunol.* 141:S25-S36; Kabat E A, et al., 1991. *Sequences of Proteins of Immunological Interest.* U.S. Department of Health and Human Services, Natl. Inst. of Health, Bethesda). Accordingly, immunoglobulins are generally heterotetrameric glycoproteins of about 150 kDa, composed of two identical light and two identical heavy chains. Each light chain is linked to a heavy chain by one covalent disulfide bond, while the number of disulfide linkages varies between the heavy chains of different immunoglobulins isotypes. Each heavy and light chain also has regularly spaced intrachain disulfide bridges. Each heavy chain has an amino terminal variable domain (VH) followed by carboxy terminal constant domains (CH). Each light chain has a variable N-terminal domain (VL) and a C-terminal constant domain (CL).

Depending on the amino acid sequence of the constant domain of the heavy chains, antibodies can be assigned to different classes. There are five major classes: IgA, IgD, IgE, IgG and IgM. The heavy chain constant domains that correspond to the different classes of antibodies are called alpha, delta, epsilon, gamma and mu domains, respectively. The mu chain of IgM contains five domains (VH, CHmu1, CHmu2, CHmu3 and CHmu4). The heavy chain of IgE also contains five domains while the heavy chain of IgA has four domains. The immunoglobulin class can be further divided into subclasses (isotypes), e.g. IgG1, IgG2, IgG3, IgG4, IgA1 and IgA2.

The subunit structures and three-dimensional configuration of different classes of immunoglobulins are well known. Of these IgA and IgM are polymeric and each subunit contains two light and two heavy chains. The heavy chain of IgG contains a polypeptide chain lying between the CHgamma1 and CHgamma2 domains known as the hinge region. The alpha chain of IgA has a hinge region containing an O-linked glycosylation site. The mu and epsilon chains do not have a sequence analogous to the hinge region of the gamma and alpha chains, however, they contain a fourth constant domain lacking in the other in the other immunoglobulin classes.

The Fc region of a full antibody usually comprises two CH2 domains and two CH3 domains. According to the present invention, the CH2 domain is preferably the CH2 domain of one of the five immunoglobulin classes indicated above. Preferred are mammalian immunoglobulin CH2 domains such as primate or murine immunoglobulin with the primate and especially human immunoglobulin CH2 domains being preferred. The amino acid sequences of immunoglobulin CH2 domains are known or are generally available to the skilled artisan (Kabat E A, et al., 1991. *Sequences of Proteins of Immunological Interest*. U.S. Department of Health and Human Services, Natl. Inst. of Health, Bethesda). A preferred immunoglobulin CH2 domain within the context of the present invention is a human IgG and preferably from IgG1, IgG2, IgG3, IgG4, more preferably a human IgG1 and IgG3 and even more preferred a human IgG1. Using the numbering system of Edelman (Edelman G M, et al., 1969. *Proc. Natl. Acad. Sci.* 63:78-85), the immunoglobulin CH2 domain preferably begins at amino acid position equivalent to glutamine 233 of human IgG1 and extends through amino acid equivalent to lysine 340 (Ellison J and Hood L, 1982. *Proc. Natl. Acad. Sci.* 79:1984-1988).

With respect to human antibody molecules reference is made to the IgG class in which an N-linked oligosaccharide is attached to the amide side chain of Asn 297 of the beta-4 bend to the inner face of the CH2 domain of the Fc region. Preferably, the antibody or Fc-fusion protein contains or is modified to contain at least a CH2 domain. The CH2 domain is a CH2 domain of an immunoglobulin having a single N-linked oligosaccharide of a human IgG CH2 domain. The CH2 domain is preferably the CH2 domain of human IgG1.

"Fc-fusion proteins" are defined as proteins which contain or are modified to contain at least the portion of the CH2 domain of the heavy chain immunoglobulin constant region comprising the single N-linked glycosylation site. According to the Kabat E U nomenclature (Kabat E A, et al., 1991. *Sequences of Proteins of Immunological Interest*. U.S. Department of Health and Human Services, Natl. Inst. of Health, Bethesda) this N-linked glycosylation site is at position Asn297 in an IgG1, IgG2, IgG3 or IgG4 antibody. The other part of the fusion protein can be the complete sequence or any part of the sequence of a natural or modified heterologous protein or a composition of complete sequences or any part of the sequence of a natural or modified heterologous protein. Fc-fusion proteins can be constructed by genetic engineering approaches by introducing the CH2 domain of the heavy chain immunoglobulin constant region comprising the N-linked glycosylation site into another expression construct comprising for example other immunoglobulin domains, enzymatically active protein portions, or effector domains. Thus, an Fc-fusion protein according to the present invention comprises also a single chain Fv fragment linked to the CH2 domain of the heavy chain immunoglobulin constant region comprising e.g. the N-linked glycosylation site.

Furthermore, antibody fragments include e.g. "Fab fragments" (Fragment antigen-binding=Fab). Fab fragments consist of the variable regions of both chains, which are held together by the adjacent constant region. These may be formed by protease digestion, e.g. with papain, from conventional antibodies, but similar Fab fragments may also be produced by genetic engineering. Further antibody fragments include F(ab')2 fragments, which may be prepared by proteolytic cleavage with pepsin.

By definition any sequences or genes introduced into a host cell are called "heterologous sequences", "heterologous genes", "heterologous RNAs" or "transgenes" or "recombinant gene" with respect to the host cell, even if the introduced sequence, RNA or gene is identical to an endogenous sequence, RNA or gene in the host cell. A "heterologous" or "recombinant" protein or RNA is thus a protein or RNA expressed from a heterologous sequence or gene. In a preferred embodiment, the introduced sequence, RNA or gene is not identical to an endogenous sequence, RNA or gene of the host cell in question, although embodiments where it is identical are also contemplated in connection with the present invention.

"Heterologous gene" or "heterologous sequences" can be introduced into a target cell directly (e.g., siRNAs) or by using an "expression vector", preferably a mammalian expression vector. Methods used to construct vectors are well known to the person skilled in the art and described in various publications. In particular techniques for constructing suitable vectors, including a description of the functional components such as promoters, enhancers, termination and polyadenylation signals, selection markers, origins of replication, and splicing signals, are reviewed in considerable details in (Sambrook J, et al., 1989. *Molecular Cloning: A Laboratory Manual*. Cold Spring Harbor: Cold Spring Harbor Laboratory Press) and references cited therein. Vectors may include but are not limited to plasmid vectors, phagemids, cosmids, artificial/mini-chromosomes (e.g. ACE), or viral vectors such as baculovirus, retrovirus, adenovirus, adeno-associated virus, herpes simplex virus, retroviruses and bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operably linked, are well known in the art and some are commercially available from companies such as Stratagene, La Jolla, Calif.; Invitrogen, Carlsbad, Calif.; Promega, Madison, Wis. or BD Biosciences Clonetech, Palo Alto, Calif. Usually expression vectors also comprise an expression cassette encoding a selectable marker, allowing selection of host cells carrying said expression marker.

In the present invention the expression vectors are also used for introducing "heterologous sequences" or "polynucleotide sequences" encoding siRNAs or shRNAs, into a host cell. Such expression vectors may comprise siRNA or shRNA sequence(s) for transient or stable expression of siRNA or shRNAs in cells, specifically in mammalian cells, even more specifically in CHO cells. Preferably, said expression vector is a mammalian expression vector. Means for cloning nucleotide sequences encoding siRNAs or shRNAs into an expression vector are known to the person skilled in the art. They include, but are not limited to cloning siRNAs or shRNA sequences comprising flanking regions into a mammalian expression vector, such as pcDNA6.2, or any other vector known in the art, operably linked to a promoter, preferably a strong promoter, such as a CMV promoter or any other strong promoter known to work in the host cell.

The term "expression" as used herein refers to transcription and/or translation of a heterologous nucleic acid sequence within a host cell. The level of expression of a host cell protein such as TBC1D20, CERS2 or ATF6B in a host cell may be determined on the basis of either the amount of corresponding mRNA that is present in the cell, or the amount of the polypeptide encoded by the selected sequence as in the present examples. For example, mRNA transcribed from a selected sequence can be quantified by Northern blot hybridization, ribonuclease RNA protection, in situ hybridization to cellular RNA or by PCR, such as qPCR. Proteins encoded by a selected sequence can be quantitated by various methods, e.g. by ELISA, by Western blotting, by radioimmunoassays, by immunoprecipitation, by assaying for the biological activity of the protein, by immunostaining of the protein followed by FACS analysis or by homogeneous time-resolved fluorescence (HTRF) assays. The level of expression of a non-coding RNA, such as a miRNA can also be quantified by PCR, such as qPCR.

The term "transformation" or "to transform", "transfection" or "to transfect" as used herein means any introduction of genetic material, into a mammalian host cell, wherein the mammalian host cell may be transiently transfected or stably transfected. The genetic material may be an expression vector comprising a gene of interest (e.g., a recombinant secreted therapeutic protein) or a polynucleotide sequence encoding siRNA or shRNA. It also means the introduction of a viral nucleic acid sequence in a way which is for the respective virus the naturally one. The viral nucleic acid sequence needs not to be present as a naked nucleic acid sequence but may be packaged in a viral protein envelope.

Transfection of eukaryotic host cells with a polynucleotide or expression vector, resulting in genetically modified cells or transgenic cells, can be performed by any method known in the art (see e.g. Sambrook J, et al., 1989. *Molecular Cloning: A Laboratory Manual*. Cold Spring Harbor: Cold Spring Harbor Laboratory Press). Transfection methods include, but are not limited to liposome-mediated transfection, calcium phosphate co-precipitation, electroporation, nucleofection, nucleoporation, microporation, polycation (such as DEAE-dextran)-mediated transfection, protoplast fusion, viral infections and microinjection. The transformation may result in a transient or stable transformation of the host cells. Preferably, the transfection is a stable transfection. The transfection method that provides optimal transfection frequency and expression of the heterologous genes in the particular host cell line and type is favoured. Suitable methods can be determined by routine procedures. For stable transfectants the constructs are either integrated into the host cell's genome or an artificial chromosome/minichromosome or located episomally so as to be stably maintained within the host cell. Thus, the stably transfected sequences actually remain in the genome of the cell and its daughter cells. Typically, this involves the use of a selectable marker gene and the gene of interest or the polynucleotide sequence encoding the RNA is integrated together with the selectable marker gene. In some cases the entire expression vector integrates into the cell's genome, in other cases only parts of the expression vector integrate into the cell's genome. Cells "stably expressing" a recombinant secreted therapeutic protein or an RNA is stably transfected with a gene encoding said recombinant secreted therapeutic protein or with a polynucleotide sequence encoding said RNA. Thus, the sequences encoding the recombinant secreted therapeutic protein or RNA remain in the genome of the cell and its daughter cells.

The expression vectors of the present invention may further comprise a selectable marker gene, such as an antibiotic resistance gene or an amplifiable marker gene. The amplifiable selection marker gene may be operably linked to the polynucleotide sequence encoding the RNA. To be operably linked, the polynucleotide sequence encoding the RNA and the amplifiable selection marker gene may be located on the same vector. Typically, the recombinant secreted therapeutic protein and the polynucleotide sequence encoding the RNA in the expression vector of the invention are operably linked to a promoter and/or a terminator. The recombinant secreted therapeutic protein or the polynucleotide sequence encoding the RNA operably linked to a promoter and/or a terminator may also be referred to as an expression cassette.

A "selectable marker gene" or "selection marker gene" is a gene which encodes a selectable marker and allows the specific selection of cells which contain this gene, typically by the addition of a corresponding "selecting agent" to the cultivation medium. As an illustration, an antibiotic resistance gene may be used as a positive selectable marker. Only cells which have been transformed with this gene are able to grow in the presence of the corresponding antibiotic and are thus selected. Untransformed cells, on the other hand, are unable to grow or survive under these selection conditions. There are positive, negative and bifunctional selectable markers. Positive selectable markers permit the selection and hence enrichment of transformed cells by conferring resistance to the selecting agent or by compensating for a metabolic or catabolic defect in the host cell. By contrast, cells which have received the gene for the selectable marker can be selectively eliminated by negative selectable markers. An example of this is the thymidine kinase gene of the Herpes Simplex virus, the expression of which in cells with the simultaneous addition of acyclovir or gancyclovir leads to the elimination thereof. The selectable marker genes useful in this invention also include the amplifiable selectable markers. The literature describes a large number of selectable marker genes including bifunctional (positive/negative) markers (see for example WO 92/08796 and WO 94/28143). Examples of selectable markers which are useful in the present invention include, but are not limited to the genes of aminoglycoside phosphotransferase (APH), hygromycine phosphotransferase (HYG), dihydrofolate reductase (DHFR), thymidine kinase (TK), glutamine synthetase, asparagine synthetase and genes which confer resistance to neomycin (G418/Geneticin), puromycin, histidinol D, bleomycin, phleomycin, blasticidin and zeocin. Also included are genetically modified mutants and variants, fragments, functional equivalents, derivatives, homologues and fusions with other proteins or peptides, provided that the selectable marker retains its selective qualities. Such derivatives display considerable homology in the amino acid sequence in the regions or domains, which are deemed to be selective.

Selection may also be made by fluorescence activated cell sorting (FACS) using for example a cell surface marker, bacterial β-galactosidase or fluorescent proteins (e.g. green fluorescent proteins (GFP) and their variants from *Aequorea victoria* and *Renilla reniformis* or other species; red fluorescent proteins, fluorescent proteins and their variants from non-bioluminescent species (e.g. *Discosoma* sp., *Anemonia* sp., *Clavularia* sp., *Zoanthus* sp.) to select for recombinant cells.

The term "selection agent" or "selective agent" refers to a substance that interferes with the growth or survival of a cell, unless a certain selectable marker gene product is present in the cell which alleviates the effect of the selection agent. For example, to select for the presence of an antibiotic resistance gene like APH (aminoglycoside phosphotransferase) in a transfected cell the antibiotic Geneticin (G418) is used.

The term "modified neomycin-phosphotransferase (NPT)" covers all the mutants described in WO2004/050884, particularly the mutant D227G (Asp227Gly), which is characterized by the substitution of aspartic acid (Asp, D) for glycine (Gly, G) at amino acid position 227 and particularly preferably the mutant F240I (Phe240Ile), which is characterized by the substitution of phenylalanine (Phe, F) for isoleucine (Ile, I) at amino acid position 240.

The "amplifiable selectable marker gene" usually codes for an enzyme, which is needed for the growth of eukaryotic cells under certain cultivation conditions. For example, the amplifiable selectable marker gene may code for dihydrofolate reductase (DHFR) or glutamine synthetase (GS). In this case the gene is amplified, if a host cell transfected therewith is cultivated in the presence of the selecting agent methotrexate (MTX) or methionine sulphoximine (MSX), respectively. Sequences linked to the amplifiable selectable marker gene (i.e., sequences physically proximal thereto) are co-amplified together with the amplifiable selectable marker gene. Said co-amplified sequences may be introduced on the same expression vector or on separate vectors.

The following Table 2 gives non-limiting examples of amplifiable selectable marker genes and the associated selecting agents, which may be used according to the invention. Suitable amplifiable selectable marker genes are also described in an overview by Kaufman (Kaufman R J, 1990. *Methods Enzymol.* 185:537-566).

TABLE 2

Amplifiable selectable marker genes

| Amplifiable selectable marker gene | Accession number | Selecting agent |
| --- | --- | --- |
| dihydrofolate reductase (DHFR) | M19869 (hamster) E00236 (mouse) | methotrexate (MTX) |
| metallothionein | D10551 (hamster) M13003 (human) M11794 (rat) | cadmium |
| CAD (carbamoylphosphate synthetase : aspartate transcarbamylase: dihydroorotase) | M23652 (hamster) D78586 (human) | N-phosphoacetyl-L-aspartate |
| adenosine-deaminase | K02567 (human) M10319 (mouse) | Xyl-A- or adenosine, 2'deoxycoformycin |
| AMP (adenylate)-deaminase | D12775 (human) J02811 (rat) | adenine, azaserin, coformycin |
| UMP-synthase | J03626 (human) | 6-azauridine, |
| IMP 5'-dehydrogenase | J04209 (hamster) J04208 (human) M33934 (mouse) | pyrazofuran mycophenolic acid |
| xanthine-guanine-phosphoribosyltransferase | X00221 (E. coli) | mycophenolic acid with limiting xanthine |
| mutant HGPRTase or mutant thymidine-kinase | J00060 (hamster) M13542, K02581 (human) J00423, M68489 (mouse) M63983 (rat) M36160 (Herpes virus) | hypoxanthine, aminopterine and thymidine (HAT) |
| thymidylate-synthetase | D00596 (human) M13019 (mouse) L12138 (rat) | 5-fluorodeoxyuridine |
| P-glycoprotein 170 (MDR1) | AF016535 (human) J03398 (mouse) | several drugs, e.g. adriamycin, vincristin, colchicine |
| ribonucleotide reductase | M124223, K02927 (mouse) | aphidicoline |
| glutamine-synthetase (GS) | AF150961 (hamster) U09114, M60803 (mouse) M29579 (rat) | methionine sulphoximine (MSX) |
| asparagine-synthetase | M27838 (hamster) M27396 (human) U38940 (mouse) U07202 (rat) | β-aspartylhydroxamate, albizziin, 5'azacytidine |
| argininosuccinate-synthetase | X01630 (human) M31690 (mouse) M26198 (bovine) | canavanin |
| ornithine-decarboxylase | M34158 (human) J03733 (mouse) M16982 (rat) | α-difluoromethylornithine |
| HMG-CoA-reductase | L00183, M12705 (hamster) M11058 (human) | compactin |
| N-acetylglucosaminyl-transferase | M55621 (human) | tunicamycin |

TABLE 2-continued

Amplifiable selectable marker genes

| Amplifiable selectable marker gene | Accession number | Selecting agent |
| --- | --- | --- |
| threonyl-tRNA-synthetase | M63180 (human) | borrelidin |
| Na$^+$K$^+$-ATPase | J05096 (human) M14511 (rat) | ouabain |

According to the invention a preferred amplifiable selectable marker gene is a gene which codes for a polypeptide with the function of GS or DHFR.

The present invention relates to mammalian cells wherein at least one gene encoding a host cell protein comprises a genetic modification that inhibits expression of said host cell protein or the mammalian cell comprises a RNA oligonucleotide that inhibits expression of the gene encoding a host cell protein by RNA-interference, wherein the at least one host cell protein is ATF6B or TBC1D20 and CERS2. The invention also relates to methods of preparing said mammalian cells and to the use of said cells in a method for producing a secreted recombinant therapeutic protein. According to the invention, reduced expression of the host cell protein means that the protein expression of TBC1D20 and CERS2 or the protein expression of ATF6B in the mammalian cell is reduced compared to the same mammalian cell not containing said genetic modification(s) or RNA oligonucleotide(s).

In one aspect, the invention relates to a mammalian cell having enhanced secretion of a recombinant therapeutic protein comprising reduced expression of the host cell proteins TBC1 domain family member 20 (TBC1D20) and ceramide synthase 2 (CERS2); wherein the mammalian cell optionally further comprises one or more expression cassette(s) encoding a recombinant secreted therapeutic protein.

In another aspect the invention relates to a mammalian cell having enhanced secretion of a recombinant therapeutic protein comprising reduced expression of the host cell protein activating transcription factor 6 beta (ATF6B), wherein the mammalian cell further comprises one or more expression cassette(s) encoding a recombinant secreted therapeutic protein.

In one embodiment of the invention, the mammalian cell having enhanced secretion of a recombinant therapeutic protein comprises reduced expression of the host cell proteins TBC1 domain family member 20 (TBC1D20) and ceramide synthase 2 (CERS2); or reduced expression of the host cell protein activating transcription factor 6 beta (ATF6B), wherein the mammalian cell further comprises one or more expression cassette(s) encoding a recombinant secreted therapeutic protein.

In order to reduce expression of the host cell protein in the mammalian cell of the invention, the gene encoding the host cell protein may comprise a genetic modification that inhibits expression of said host cell protein, or the mammalian cell may comprise a RNA oligonucleotide that inhibits expression of the gene encoding said host cell protein by RNA-interference. Reduced expression of the host cell protein means that the protein expression of TBC1D20 and CERS2 or the protein expression of ATF6B in the mammalian cell is reduced compared to the same mammalian cell not containing said genetic modification(s) or RNA oligonucleotide(s). In one embodiment, the RNA oligonucleotide that inhibits expression of the gene of the host cell protein by RNA-interference is not a miRNA.

The invention also relates to a method of producing a mammalian cell with enhanced secretion of a recombinant therapeutic protein comprising (a) reducing expression of the host cell proteins TBC1D20 and CERS2, or of the host cell protein ATF6B in the mammalian cell by introducing (i) a genetic modification into a gene encoding the host cell protein that inhibits expression of said host cell protein, or (ii) a RNA oligonucleotide into the mammalian cell that inhibits expression of the gene encoding said host cell protein by RNA-interference, and (b) introducing one or more gene(s) encoding a recombinant secreted therapeutic protein. The method may further comprise a step of (c) selecting cells with enhanced secretion of the recombinant therapeutic protein. The method may furthermore comprise a step of (d) culturing the cells obtained in step (c) under conditions which allow expression of one or more gene(s) encoding a recombinant secreted therapeutic protein. The introduction of one or more gene(s) encoding the secreted therapeutic protein in step (b) preferably comprises introducing one or more expression cassette(s) encoding the recombinant secreted therapeutic. Step (a) of the method of the invention may be performed before or after step (b). Thus, the one or more gene(s) encoding the recombinant secreted protein may be introduced before the genetic modification or RNA oligonucleotides (or the expression vector comprising a nucleotide sequence encoding said RNA oligonucleotide) resulting in reduced expression of the host cell protein ATF6B or the host cell proteins TBC1D20 and CERS2 is introduced. Alternatively, the one or more gene(s) encoding the recombinant secreted protein may be introduced after the genetic modification or RNA oligonucleotides (or the expression vector comprising a nucleotide sequence encoding said RNA oligonucleotide) resulting in reduced the expression of the host cell protein ATF6B or the host cell proteins TBC1D20 and CERS2 is introduced. The invention further relates to a mammalian cell line produced by the method of the invention.

The mammalian cells and the mammalian cells produced by the method of the invention may further be used in a method for the production of a recombinant secreted therapeutic protein in a mammalian cell. The method comprising (a) providing the mammalian cell of the invention, wherein the cell is transfected with a recombinant secreted therapeutic protein or providing the mammalian cell produced by the method of the invention; (b) culturing the mammalian cell of step (a) in a cell culture medium at conditions allowing production of the recombinant secreted therapeutic protein, and (c) harvesting the recombinant secreted therapeutic protein. The method may further comprise (d) purifying the recombinant secreted therapeutic protein.

In order to reduce expression of the host cell protein in the method of the invention, the gene encoding the host cell protein may comprise a genetic modification that inhibits expression of said host cell protein, or the mammalian cell may comprise a RNA oligonucleotide that inhibits expression of the gene encoding said host cell protein by RNA-interference. Reduced expression of the host cell protein means that the protein expression of TBC1D20 and CERS2 or the protein expression of ATF6B in the mammalian cell is reduced compared to the same mammalian cell not containing said genetic modification(s) or RNA oligonucleotide(s).

The mammalian cells and the mammalian cells produced by the method of the invention may further be used for the production of a recombinant secreted therapeutic protein or increasing the yield of the recombinant secreted therapeutic protein. The invention therefore also relates to a use of the mammalian cell of the invention or the mammalian cell produced by the method of the invention for increasing the yield of a recombinant secreted therapeutic protein. It further relates to a use of the mammalian cell of the invention or the mammalian cell produced by the method of the invention for production of a recombinant secreted therapeutic protein.

The recombinant secreted therapeutic protein produced by the mammalian cell or the method of the invention is preferably an antibody, preferably a monoclonal antibody, a bi-specific antibody or a fragment thereof, or a Fc-fusion protein.

Reduced Expression of the Host Cell Proteins TBC1D20, CERS2 or ATF6B

The expression of the host cell proteins TBC1D20, CERS2 or ATF6B is reduced in a mammalian cell according to the invention or used or produced in the methods of the invention. This means that the protein expression of TBC1D20, CERS2 or ATF6B in the mammalian cell is reduced compared to the same mammalian cell not containing said genetic modification or RNA oligonucleotide by gene knockdown or gene knockout.

In one embodiment, the expression of the host cell proteins TBC1D20 and CERS2 is reduced. The host cell protein TBC1D20 refers to hamster TBC1D20 expressed in CHO cells such as encoded by the cDNA sequence of SEQ ID NO: 1, or having the amino acid sequence of SEQ ID NO: 4, or any homologues thereof. As used herein, a homologue thereof means a protein having a sequence identity of at least 80%, at least 85%, at least 90%, at least 95% or at least 98% to the amino acid sequence of SEQ ID NO: 4. The host cell protein CERS2 refers to the hamster CERS2 expressed in CHO cells, such as encoded by the cDNA sequence of SEQ ID NO: 2 or having the amino acid sequence of SEQ ID NO: 5 or any homologues thereof. As used herein, a homologue thereof means a protein having a sequence identity of at least 80%, at least 85%, at least 90%, at least 95% or at least 98% to the amino acid sequence of SEQ ID NO: 5.

In another embodiment, the expression of ATF6B is reduced compared to control cells. The host cell protein ATF6B refers to the hamster ATF6B expressed in CHO cells, such as encoded by the cDNA sequence of SEQ ID NO: 3 or having the amino acid sequence of SEQ ID NO: 6 or any homologue thereof. As used herein, a homologue thereof means a protein having a sequence identity of at least 80%, at least 85%, at least 90%, at least 95% or at least 98% to the amino acid sequence of SEQ ID NO: 6. The person skilled in the art would understand that also the expression of host cell proteins ATF6B, TBC1D20 and CERS2 may be reduced.

The term "knockdown" or "knockdown technology" refers to a technique of gene silencing in which the expression of a target gene or gene of interest is reduced as compared to the gene expression prior to the introduction of an RNA oligonucleotide that inhibits expression of a target gene by RNA-interference, such as by using siRNA or shRNA, which can lead to the inhibition of production of the target gene product. "Double knockdown" is the knockdown of two genes, such as the genes encoding for TBC1D20 and CERS2.

In one embodiment, the mammalian cell comprises a RNA oligonucleotide that inhibits expression of the gene encoding said host cell protein by RNA-interference, wherein host cell protein refers to ATF6B or TBC1D20 and CERS2. The skilled person will recognize that the RNA oligonucleotide may be transfected directly into the cell or may be encoded by a polynucleotide sequence within the cell, e.g., by using an expression vector. Hence, the expression vector comprises a polynucleotide sequence encoding said RNA oligonucleotide. An expression vector may also comprise a polynucleotide sequence encoding a second RNA oligonucleotide. The two RNA oligonucleotides may be encoded by two separate expression cassettes or by the same expression cassette separated, e.g., by an IRES sequence. Overexpression of siRNA(s) or shRNA(s) targeting ATF6B or to the combination of TBC1D20 and CERS2, leads to an enhanced production and/or secretion of the secreted recombinant therapeutic protein in a mammalian expression system.

Preferably the RNA oligonucleotide mediates mRNA repression by complete sequence complementarity (i.e., perfect base paring between the antisense strand of the RNA duplex of the small interfering RNA and the target mRNA) and is therefore specific for its target. Complete sequence complementarity of perfect base paring as used herein means that the antisense strand of the RNA duplex of the small interfering RNA has at least 89% sequence identity with the target mRNA for at least 15 continuous nucleotides, at least 16 continuous nucleotides, at least 17 continuous nucleotides, at least 18 continuous nucleotides and preferably at least 19 continuous nucleotides, or preferably at least 93% sequence identity with the target mRNA for at least 15 continuous nucleotides, at least 16 continuous nucleotides, at least 17 continuous nucleotides, at least 18 continuous nucleotides and preferably at least 19 continuous nucleotides. Preferably the antisense strand of the RNA duplex of the small interfering RNA has 100% sequence identity with the target mRNA for at least 15 continuous nucleotides, at least 16 continuous nucleotides, at least 17 continuous nucleotides, at least 18 continuous nucleotides and preferably at least 19 continuous nucleotides. The skilled person will understand that miRNAs do not mediate mRNA repression by complete sequence complementarity and are therefore not gene-specific. Thus, in one embodiment, the RNA oligonucleotide is not a miRNA.

Preferably the RNA-interference is mediated by small hairpin RNA (shRNA) or short interfering RNA (siRNA). The mammalian cell may be transfected with one or more expression vector(s) encoding said siRNA(s) or shRNA(s). Preferably the mammalian cell is stably transfected with one or more expression vector(s) encoding said siRNA(s) or shRNA(s). The RNA oligonucleotide may be constitutively expressed or conditionally expressed. For example, expression of the RNA oligonucleotide may be silent during growth phase and switched on during protein production phase.

An exemplary siRNA for knocking-down TBC1D20 is siTbc1D20#1 (SEQ ID NO: 7). An exemplary siRNA for knocking-down CERS2 is siCerS2#1 (SEQ ID NO: 8). Preferably the siRNAs having the sequence of SEQ ID NOs: 7 or 8 are used in CHO cells. These siRNAs can be used independently of each other. Thus, each of siTbc1D20#1 or siCERS2#1 may be used or both siRNAs may be used. While the expression of both, TBC1D20 and CERS2, is reduced according to the method or the mammalian cell of the invention, the means to achieve the reduction of the host cell proteins are independent of each other. Thus, expression of host cell protein TBC1D20 may be reduced by gene knockdown using siRNA and expression of host cell protein CERS2 may be reduced by gene knockdown using shRNA, or vice versa. Alternatively, the expression of host cell protein TBC1D20 may be reduced by gene knockdown, e.g., using siRNA and expression of host cell protein CERS2 may be reduced by gene knockout, or vice versa.

An exemplary shRNA for knocking-down TBC1D20 comprises shTbc1D20#1 (SEQ ID NO: 12); an exemplary shRNA for knocking-down CERS2 comprises shCerS2#1 (SEQ ID NO: 13) or shCerS2#2 (SEQ ID NO: 14), or a combination of said shRNAs. Preferably, the shRNAs comprising the sequence of SEQ ID NOs: 12, 13 or 14, are used in CHO cells. Exemplary DNA oligonucleotides encoding shRNAs suitable in the present invention for knocking-down TBC1D20 (SEQ ID NOs: 16 and 17) or CERS2 (SEQ ID NOs 18-21) are shown below. Preferably the DNA oligonucleotide encoding the shRNA targeting TBCD1D20 comprises the sequence of nucleotides 6 to 26 of SEQ ID NO: 16 (shTBC1D20#1 oligonucleotide forward) and more preferably the sequence of nucleotides 6 to 26 and 46 to 64 of SEQ ID NO: 16 (shTBC1D20#1 oligonucleotide forward). Preferably the DNA oligonucleotide encoding the shRNA targeting CERS2 comprises the sequence of nucleotides 6 to 26 of SEQ ID NOs: 18 or 20 (shCERS2#1 or #2 oligonucleotide forward) and more preferably the sequence of nucleotides 6 to 26 and 46 to 64 of SEQ ID NOs: 18 or 20 (shCERS2#1 or #2 oligonucleotide forward).

These shRNAs can be used independently of each other. Thus, shTbc1D20#1, shCERS2#1 or shCERS2#2 may be used, or shTbc1D20#1 and shCERS2#1 or shCERS2#2 may be used. While the expression of both, TBC1D20 and CERS2 is reduced according to the method or the mammalian cell of the invention, the means to achieve the reduction of the host cell proteins are independent of each other. Thus, expression of host cell protein TBC1D20 may be reduced by gene knockdown using siRNA and expression of host cell protein CERS2 may be reduced by gene knockdown using shRNA, or vice versa. Alternatively, the expression of host cell protein TBC1D20 may be reduced by gene knockdown, e.g., using shRNA, and the expression of host cell protein CERS2 may be reduced by gene knockout, or vice versa.

Exemplary siRNAs for knocking-down ATF6B are siAtf6b #1 (SEQ ID NO: 9), siAtf6b #2 (SEQ ID NO: 10), or siAtf6b #3 (SEQ ID NO: 11). Preferably one or more of siAtf6b #1 (SEQ ID NO: 9), siAtf6b #2 (SEQ ID NO: 10), and siAtf6b #3 (SEQ ID NO: 11) are used according to the invention, more preferably one or more of siAtf6b #1 (SEQ ID NO: 9) and siAtf6b #2 (SEQ ID NO: 10) are used. An exemplary shRNA for knocking-down ATF6B comprises shAtf6b #1 (SEQ ID NO: 15) or shAtf6b #2 (SEQ ID NO: 37), preferably shAtf6b #1 (SEQ ID NO: 15). Preferably the siRNAs having the sequence of SEQ ID NOs: 9, 10 or 11 or the shRNA comprising the sequence of SEQ ID NOs: 15 or 37 are used in CHO cells. Exemplary DNA oligonucleotides encoding shRNAs suitable in the present invention for knocking-down ATF6B are shown below (SEQ ID NOs: 22, 23, 35 and 36). Preferably the DNA oligonucleotide encoding the respective shRNA targeting ATF6B comprises the sequence of nucleotides 6 to 26 of SEQ ID NOs: 22 or 35 (shATF6B #1 or #2 oligonucleotide forward) and more preferably the sequence of nucleotides 6 to 26 and 46 to 64 of SEQ ID NOs: 22 or 35 (shATF6B #1 or #2 oligonucleotide forward).

In another embodiment, at least one gene encoding a host cell protein comprises a genetic modification that inhibits expression of said host cell protein. The genetic modification in the gene(s) encoding the host cell protein(s) TBC1D20, CERS2 or ATF6B may be independent of each other a gene deletion or a mutation in the gene that inhibits expression of the host cell protein. The mutation may be a deletion, addition or substitution. The skilled person would know that the mutation may be in the coding region of the gene and/or the mutation may be in the promoter or a regulatory region of the gene as long as the gene expression is reduced. Preferably, the mutation is in the promoter or regulatory region of the gene. The mutation may be introduced using methods known in the art. The skilled person would understand that the same effect may be achieved using overexpression of a dominant mutant host cell protein that has reduced protein activity. Alternatively, the host cell protein gene may be deleted in the mammalian cell and an expression cassette encoding said host cell protein under the control of a weak promoter may be introduced into the mammalian cell, resulting in an overall reduced expression of the host cell protein compared to a control cell (i.e., the same mammalian cell not containing said gene deletion). This gene mutation may be either in one or both alleles of a gene.

Reduced host cell protein expression can be determined by comparing the protein expression of TBC1D20, CERS2 or ATF6B in the mammalian cell compared to a control mammalian cell, i.e., the same mammalian cell not containing said genetic modification or RNA oligonucleotide. Preferably, the expression of the host cell protein ATF6B or of host cell proteins TBC1D20, CERS2 are reduced by at least 30%, at least 40%, at least 50%, at least 75%, or 100%, compared to a control mammalian cell. This may be measured on protein level, e.g., by ELISA, by Western blotting, by radioimmunoassays, immunoprecipitation, assaying for the biological activity of the protein, by immunostaining of the protein followed by FACS analysis or by homogeneous time-resolved fluorescence (HTRF) assays, or any other suitable method known in the art for quantifying protein. The reduced expression of host cell protein ATF6B or of host cell proteins TBC1D20, CERS2 may also be determined on mRNA level, e.g., by quantitative PCR or any other suitable method known in the art for quantifying mRNA. mRNA transcribed from a selected sequence can further be quantified by Northern blot hybridization, ribonuclease RNA protection, in situ hybridization to cellular RNA or by PCR.

It is particularly important that the host cell protein expression is reduced during production phase. It is therefore possible that knockdown of host cell protein expression induced after growth phase or early in production phase as long as host cell protein expression is reduced during most of the production phase. Host cell protein expression should be reduced at least 3 days before end of culture, at least 5 days before end of culture, at least 7 days before end of culture or at least 9 days before end of culture. Preferably the host cell protein expression is reduced throughout cell culture.

A gene may also be modified by deleting the gene using "knockout" technology. The term "knockout" refers to cells which have been genetically modified so that the expression of host cell proteins AFT6B or the combination of host cell proteins TBC1D20 and CERS2 is/are inhibited and the respective host cell protein is not produced (reduction by 100%). This may be achieved using various technologies which are known in the art to the skilled person, including CRISPR-Cas9 or Zinc finger nuclease technology. Alternatively, the gene may be altered to inhibit the expression of its protein by introduction of a mutation in the gene. The gene mutation may be a nucleotide deletion, addition or substitution in the coding region or in the promoter or regulatory region of the gene. This gene mutation may be either in one or both alleles of a gene.

Enhanced Secretion of the Recombinant Therapeutic Protein

The reduced expression of ATF6B or TBC1D20 and CERS2 in a mammalian cell according to the invention results in an enhanced secretion of the recombinant therapeutic protein. Protein secretion can be increased by improved cell density or cell viability. It may also be increased by improved specific cell productivity. However, the skilled person will understand that having improved cell density or cell viability only enhances the total yield of the secreted recombinant therapeutic protein in case the specific cell productivity is not substantially affected or even improved. Likewise having increased specific cell productivity only enhances the total yield of the secreted recombinant therapeutic protein in case the cell density or cell viability is not substantially affected or even improved. Enhanced secretion of the recombinant therapeutic protein therefore refers to the total yield of the recombinant therapeutic protein in the cell culture, typically measured as a concentration (titer), such as mg/ml. The secretion of the recombinant therapeutic protein according to the invention is enhanced by at least 10%, at least 20%, at least 30%, at least 40%, at least 50%, at least 75%, at least 100% or at least 200%, compared to a control mammalian cell, i.e., not containing said genetic modification or RNA oligonucleotide. In a preferred embodiment yield of the secretion of the recombinant therapeutic protein is enhanced at harvest.

The protein ATF6b is involved in unfolded protein responses (UPR). It has been described before that only "ATF6α, but neither ATF6β nor ATF4, has the ability to trigger expansion of the ER" (Bommiasamy et al., 2009, *Journal of Cell Sciences*. 122: 1626-1636) and that only ATF6a is responsible for transcriptional induction of ER chaperones (Yamamoto et al., 2007, *Cell*. 13: 365-376). It was further reported that ATF6b is a very weak transcriptional activator of ER stress response (ERSR) genes compared to ATF6a (Thuerauf et al., 2007, *The Journal of Biological Chemistry*. 282(31): 22865-22878). Without being bound by theory, we therefore believe that depletion of ATF6b in producer cell lines might augment the transcriptional activity of ATF6a and thus increase the protein folding capacity of the ER by triggering the expression of ER chaperones.

Ceramides of varying chain lengths are synthesized by six different isoforms of Ceramide Synthases (CERS1-6) in the ER. CERS2 catalyzes the synthesis of very long chain ceramides (C20-C26) and its depletion in mice has been shown to decrease very long chain ceramides (>C22) whilst inducing a compensatory increase in C16-C18 ceramides (Grösch S, et al., 2012. Progress in Lipid Research. 51:50-62). CERT efficiently transfers ceramides having C14, C16, C18, and C20 chains, but it does not transfer longer acyl chains (Kumagai D, et al., 2005. *The Journal of Biological Chemistry*. 280(8):6488-6495). Thus, without being bound by theory, the efficiency of the CERT mediated ceramide transport might be increased by depleting CERS2, resulting in a higher amount of proteins that are transferred to the plasma membrane.

The small GTPase Rab1 has a crucial role in the vesicular transport of proteins that have been processed in the ER. GTP-bound Rab1 is required to maintain the Golgi Apparatus (Haas A, et al., 2007. Journal of Cell Science. 120: 2997-3010). TBC1D20 is a GTPase-activating protein (GAP). It catalyzes the conversion of active, GTP-bound Rab1 into an inactive, GDP-bound state. Thus, without being bound by theory, depletion of TBC1D20 might result in a constitutive active form of Rab1, positively affecting vesicular protein transport process.

TBC1D20 and CERS2 are both involved in protein transport at the Golgi apparatus. Reduction of TBC1D20 and CERS2 expression therefore seem to act synergistically, resulting in an increased recombinant protein secretion compared to reduction of each of said proteins alone.

Secreted Recombinant Therapeutic Protein

The secreted recombinant therapeutic protein produced in the mammalian cells of the invention includes, but is not limited to an antibodies or a fusion protein, such as a Fc-fusion proteins. Other secreted recombinant therapeutic proteins can be for example enzymes, cytokines, lymphokines, adhesion molecules, receptors and derivatives or fragments thereof, and any other polypeptides and scaffolds that can serve as agonists or antagonists and/or have therapeutic or diagnostic use.

Other recombinant proteins of interest are for example, but not limited to insulin, insulin-like growth factor, hGH, tPA, cytokines, such as interleukins (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1, and VEGF. Also included is the production of erythropoietin or any other hormone growth factors and any other polypeptides that can serve as agonists or antagonists and/or have therapeutic or diagnostic use.

A preferred recombinant secreted therapeutic protein is an antibody or a fragment or derivative thereof. Thus, the invention can be advantageously used for production of antibodies such as monoclonal antibodies, multispecific antibodies, or fragments thereof, preferably of monoclonal antibodies, bi-specific antibodies or fragments thereof. Furthermore, the method for producing a recombinant secreted therapeutic protein according to the invention can be advantageously used for production of antibodies such as monoclonal antibodies, multispecific antibodies, or fragments thereof, preferably of monoclonal antibodies, bi-specific antibodies or fragments thereof. Exemplary antibodies within the scope of the present invention include but are not limited to anti-CD2, anti-CD3, anti-CD20, anti-CD22, anti-CD30, anti-CD33, anti-CD37, anti-CD40, anti-CD44, anti-CD44v6, anti-CD49d, anti-CD52, anti-EGFR1 (HER1), anti-EGFR2 (HER2), anti-GD3, anti-IGF, anti-VEGF, anti-TNFalpha, anti-IL2, anti-IL-5R or anti-IgE antibodies, and are preferably selected from the group consisting of anti-CD20, anti-CD33, anti-CD37, anti-CD40, anti-CD44, anti-CD52, anti-HER2/neu (erbB2), anti-EGFR, anti-IGF, anti-VEGF, anti-TNFalpha, anti-IL2 and anti-IgE antibodies.

Antibody fragments include e.g. "Fab fragments" (Fragment antigen-binding=Fab). Fab fragments consist of the variable regions of both chains, which are held together by the adjacent constant region. These may be formed by protease digestion, e.g. with papain, from conventional antibodies, but similar Fab fragments may also be produced by genetic engineering. Further antibody fragments include F(ab')2 fragments, which may be prepared by proteolytic cleavage with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilized. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins are known to the person skilled in the art.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interactions between the VH/VL regions of the scFv are used for the multimerisation (e.g. dia-, tri- and pentabodies). By diabody the skilled person means a bivalent homodimeric scFv derivative. The shortening of the Linker in a scFv molecule to 5-10 amino acids leads to the formation of homodimers in which an inter-chain VH/VL-superimposition takes place. Diabodies may additionally be stabilized by the incorporation of disulphide bridges. Examples of diabody-antibody proteins are known to the person skilled in the art.

Preferred secreted recombinant therapeutic antibodies according to the invention are bispecific antibodies. Bispecific antibodies typically combine antigen-binding specificities for target cells (e.g., malignant B cells) and effector cells (e.g., T cells, NK cells or macrophages) in one molecule. Examplary bispecific antibodies, without being limited thereto are diabodies, BiTE (Bi-specific T-cell Engager) formats and DART (Dual-Affinity Re-Targeting) formats. The diabody format separates cognate variable domains of heavy and light chains of the two antigen binding specificities on two separate polypeptide chains, with the two polypeptide chains being associated noncovalently. The DART format is based on the diabody format, but it provides additional stabilization through a C-terminal disulfide bridge.

By triabody the skilled person means a trivalent homotrimeric scFv derivative. In said scFv derivatives the VH-VL domains are fused directly without a linker sequence, which leads to the formation of trimers. The skilled person will also be familiar with so-called miniantibodies which have a bi-, tri- or tetravalent structure and are derived from scFv. The multimerisation is carried out by di-, tri- or tetrameric coiled coil structures.

Also anticipated in the context of the present invention are minibodies. By minibody, the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. Examples of minibody-antibody proteins are known to the person skilled in the art.

Another preferred recombinant secreted therapeutic protein is a fusion protein, such as Fc-fusion protein. Thus, the invention can be advantageously used for production of fusion proteins, such as Fc-fusion proteins. Furthermore, the method for producing a secreted recombinant therapeutic protein according to the invention can be advantageously used for production of fusion proteins, such as Fc-fusion proteins.

The effector part of the fusion protein can be the complete sequence or any part of the sequence of a natural or modified heterologous protein or a composition of complete sequences or any part of the sequence of a natural or modified heterologous protein. The immunoglobulin constant domain sequences may be obtained from any immunoglobulin subtypes, such as IgG1, IgG2, IgG3, IgG4, IgA1 or IgA2 subtypes or classes such as IgA, IgE, IgD or IgM. Preferentially they are derived from human immunoglobulin, more preferred from human IgG and even more preferred from human IgG1 and IgG3. Non-limiting examples of Fc-fusion proteins are MCP1-Fc, ICAM-Fc, EPO-Fc and scFv fragments or the like coupled to the CH2 domain of the heavy chain immunoglobulin constant region comprising the N-linked glycosylation site. Fc-fusion proteins can be constructed by genetic engineering approaches by introducing the CH2 domain of the heavy chain immunoglobulin constant region comprising the N-linked glycosylation site into another expression construct comprising for example other immunoglobulin domains, enzymatically active protein portions, or effector domains. Thus, an Fc-fusion protein according to the present invention comprises also a single chain Fv fragment linked to the CH2 domain of the heavy chain immunoglobulin constant region comprising e.g. the N-linked glycosylation site. The recombinant secreted therapeutic protein, especially the antibody, antibody fragment or Fc-fusion protein is preferably recovered/isolated from the culture medium as a secreted polypeptide. It is necessary to purify the recombinant secreted therapeutic protein from other recombinant proteins and host cell proteins to obtain substantially homogenous preparations of the recombinant secreted therapeutic protein. As a first step, cells and/or particulate cell debris are removed from the culture medium or lysate. Further, the recombinant secreted therapeutic protein is purified from contaminant soluble proteins, polypeptides and nucleic acids, for example, by fractionation on immunoaffinity or ion-exchange columns, ethanol precipitation, reverse phase HPLC, Sephadex chromatography, and chromatography on silica or on a cation exchange resin such as DEAE. Methods for purifying a heterologous protein expressed by host cells are known in the art.

In one embodiment the recombinant secreted therapeutic protein is encoded by one or more expression cassette(s) encoding the secreted.

In some embodiments, the secreted therapeutic protein may be placed under the control of an amplifiable genetic selection marker, such as dihydrofolate reductase (DHFR), glutamine synthetase (GS). The amplifiable selection marker gene can be on the same expression vector as the secreted therapeutic protein expression cassette. Alternatively, the amplifiable selection marker gene and the secreted therapeutic protein expression cassette can be on different expression vectors, but integrate in close proximity into the host cell's genome. Two or more vectors that are co-transfected simultaneously, for example, often integrate in close proximity into the host cell's genome. Amplification of the genetic region containing the secreted therapeutic protein expression cassette is then mediated by adding the amplification agent (e.g., MTX for DHFR or MSX for GS) into the cultivation medium.

Sufficiently high stable levels of the secreted therapeutic protein in the host cell or the producer cell may also be achieved, e.g., by cloning multiple copies of the secreted therapeutic protein encoding-polynucleotide into an expression vector. Cloning multiple copies of the secreted therapeutic protein-encoding polynucleotide into an expression vector and amplifying the secreted therapeutic protein expression cassette as described above may further be combined.

Antibody Production

For producing a recombinant antibody, the DNA molecules encoding full-length light and heavy chains or fragments thereof are inserted into an expression vector such that the sequences are operatively linked to transcriptional and translational control sequences. Alternatively, DNA molecules encoding light chain variable regions and heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibody. For manufacturing the antibodies of the invention, the skilled artisan may choose from a great variety of expression systems well known in the art, e.g. those reviewed by Kipriyanow and Le Gall, 2004. *Molecular Biotechnology*. 26:39-60. Expression vectors include plasmids, retroviruses, cosmids, EBV-derived episomes, and the like. The term "expression vector" comprises any vector suitable for the expression of a foreign DNA. Examples of such expression vectors are viral vectors, such as adenovirus, vaccinia virus, baculovirus and adeno-associated virus vectors. In this connection, the expression "virus vector" is understood to mean both a DNA and a viral particle. Examples of phage or cosmid vectors include pWE15, M13, λEMBL3, λEMBL4, λFIXII, λDASHII, λZAPII, λgT10, λgt11, Charon4A and Charon21A. Examples of plasmid vectors include pBR, pUC, pBluescriptII, pGEM, pTZ and pET groups. Various shuttle vectors may be used, e.g., vectors which may autonomously replicate in a plurality of host microorganisms such as *E. coli* and Pseudomonas spin addition, artificial chromosome vectors are considered as expression vectors. The expression vector and expression control sequences are selected to be compatible with the host cell. Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, D H26S, D HBB, pNMT1, pNMT41, pNMT81, which are available from Invitrogen, pCI which is available from Promega, pMbac, pPbac, pBK-RSV and pBK-CMV which are available from Stratagene, pTRES which is available from Clontech, and their derivatives.

The antibody light chain gene and the antibody heavy chain gene can be inserted into separate vectors. In certain embodiments, both DNA sequences are inserted into the same expression vector. Convenient vectors are those that encode a functionally complete human CH or CL immunoglobulin sequence, with appropriate restriction sites engineered so that any VH or VL sequence can be easily inserted and expressed, as described above, wherein the CH1 and/or upper hinge region comprises at least one amino acid modification of the invention. The constant chain is usually kappa or lambda for the antibody light chain. The recombinant expression vector may also encode a signal peptide that facilitates secretion of the antibody chain from a host cell. The DNA encoding the antibody chain may be cloned into the vector such that the signal peptide is linked in-frame to the amino terminus of the mature antibody chain DNA.

The signal peptide may be an immunoglobulin signal peptide or a heterologous peptide from a non-immunoglobulin protein. Alternatively, the DNA sequence encoding the antibody chain may already contain a signal peptide sequence. In addition to the DNA sequences encoding the antibody chains, the recombinant expression vectors carry regulatory sequences including promoters, enhancers, termination and polyadenylation signals and other expression control elements that control the expression of the antibody chains in a host cell. Examples for promoter sequences (exemplified for expression in mammalian cells) are promoters and/or enhancers derived from (CMV) (such as the CMV Simian Virus 40 (SV40) (such as the SV40 promoter/enhancer), adenovirus, (e.g., the adenovirus major late promoter (Ad-MLP)), polyoma and strong mammalian promoters such as native immunoglobulin and actin promoters. Examples for polyadenylation signals are BGH polyA, SV40 late or early polyA; alternatively, 3'UTRs of immunoglobulin genes etc. can be used.

The recombinant expression vectors may also carry sequences that regulate replication of the vector in host cells (e.g. origins of replication) and selectable marker genes. Nucleic acid molecules encoding the heavy chain or an antigen-binding portion thereof and/or the light chain or an antigen-binding portion thereof of an antibody of the present invention, and vectors comprising these DNA molecules can be introduced into host cells, e.g. bacterial cells or higher eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

It is within ordinary skill in the art to express the heavy chain and the light chain from a single expression vector or from two separate expression vectors. Preferably, the DNA molecules encoding the heavy chain and the light chain are present on two vectors which are co-transfected into the host cell, preferably a mammalian cell.

Mammalian cell lines available as hosts for expression are well known in the art and include, inter alia, Chinese hamster ovary (CHO, CHO-DG44, CHO-K1) cells, NSO, SP2/0 cells, HeLa cells, HEK293 cells, baby hamster kidney (BHK) cells, monkey kidney cells (COS), human carcinoma cells (e.g., HepG2), A549 cells, 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used. The antibody molecules of the invention are produced by culturing the host cells for a period of time sufficient to allow for expression of the antibody molecule in the host cells. Following expression, the intact antibody (or the antigen-binding fragment of the antibody) can be harvested and purified using techniques well known in the art, e.g., Protein A, Protein G, affinity tags such as glutathione-S-transferase (GST) and histidine tags.

Protein Purification

The recombinant secreted therapeutic proteins are preferably recovered from the culture medium as a secreted polypeptide. It is necessary to purify the recombinant secreted therapeutic proteins using standard protein purification methods used for recombinant proteins in a way that substantially homogenous preparations of the protein are obtained. By way of example, state-of-the art purification methods useful for obtaining the recombinant secreted therapeutic protein of the invention include, as a first step, removal of cells and/or particulate cell debris from the culture medium or lysate. The recombinant secreted therapeutic protein is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. Antibodies or Fc-fusion proteins, e.g., may be purified by standard protein A chromatography, e.g., using protein A spin columns (GE Healthcare). Protein purity may be verified by reducing SDS PAGE. recombinant secreted therapeutic protein concentrations may be determined by measuring absorbance at 280 nm and utilizing the protein specific extinction coefficient. As a final step in the process for obtaining an recombinant secreted therapeutic protein preparation, the purified recombinant secreted therapeutic protein may be dried, e.g. lyophilized, as described below for therapeutic applications.

Pharmaceutical Compositions

To be used in therapy, the recombinant secreted therapeutic protein may be formulated into a pharmaceutical composition appropriate to facilitate administration to animals or humans. Pharmaceutical compositions containing the recombinant secreted therapeutic protein can be presented in a dosage unit form and can be prepared by any suitable method. Typical formulations of a recombinant secreted therapeutic protein can be prepared by mixing the protein with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g. Zn-protein complexes); and/or ionic or non-ionic surfactants such as TWEEN™ (polysorbates), PLURONICS™ or fatty acid esters, fatty acid ethers or sugar esters. Also organic solvents can be contained in the recombinant secreted therapeutic protein formulation such as ethanol or isopropanol. The excipients may also have a release-modifying or absorption-modifying function.

The recombinant secreted therapeutic protein may also be dried (freeze-dried, spray-dried, spray-freeze dried, dried by near or supercritical gases, vacuum dried, air-dried), precipitated or crystallized or entrapped in microcapsules that are prepared, for example, by coacervation techniques or by interfacial polymerization using, for example, hydroxymethylcellulose or gelatin and poly-(methylmethacylate), respectively, in colloidal drug delivery systems (for example, liposomes, albumin microspheres, microemulsions, nano-particles and nanocapsules), in macroemulsions or precipitated or immobilized onto carriers or surfaces, for example by pcmc technology (protein coated microcrystals). Such techniques are disclosed in Remington: The Science and Practice of Pharmacy, 21st edition, Hendrickson R. Ed.

Naturally, the formulations to be used for in vivo administration must be sterile; sterilization may be accomplished be conventional techniques, e.g. by filtration through sterile filtration membranes. It may be useful to increase the concentration of the antibody to come to a so-called high concentration liquid formulation (HCLF); various ways to generate such HCLFs have been described.

The recombinant secreted therapeutic protein may also be contained in a sustained-release preparation. Further, the recombinant secreted therapeutic protein can be incorporated in other application forms, such as dispersions, suspensions or liposomes, tablets, capsules, powders, sprays, transdermal or intradermal patches or creams with or without permeation enhancing devices, wafers, nasal, buccal or pulmonary formulations, or may be produced by implanted cells or—after gene therapy—by the individual's own cells.

A recombinant secreted therapeutic protein may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding.

The preferred mode of application is parenteral, by infusion or injection (intravenous, intramuscular, subcutaneous, intraperitoneal, intradermal), but other modes of application such as by inhalation, transdermal, intranasal, buccal, oral, may also be applicable.

For the prevention or treatment of disease, the appropriate dosage of the recombinant secreted therapeutic protein will depend on the type of disease to be treated, the severity and course of the disease, whether the recombinant secreted therapeutic protein is administered for preventive or therapeutic purposes, previous therapy, the patient's clinical history and response to the recombinant secreted therapeutic protein, and the discretion of the attending physician. The recombinant secreted therapeutic protein is suitably administered to the patient at one time or over a series of treatments.

Materials and Methods

TABLE 3

Cell lines use in the Examples

| Designation | Description | Species |
|---|---|---|
| CHO-mAb1 | CHO-DG44-based producer cell clone secreting the IgG1 antibody mAb1 (with a heavy chain with a sequence according to SEQ ID NO: 24 and a light chain sequence according to SEQ ID NO: 25) | Hamster |
| CHO-mAb2 | CHO-DG44-based producer cell clone secreting the IgG1 antibody mAb2 (with a heavy chain sequence according to SEQ ID NO: 26 and a light chain sequence according to SEQ ID NO: 27) | Hamster |

Cell Culture of Suspension Cells

Suspension cultures of mAb producing CHO-DG44 cells (Urlaub G, et al., 1986. *Somatic Cell and Molecular Genetics*. 12(6):555-566) and stable transfectants thereof were incubated in a chemically defined, serum-free medium. Seed stock cultures were sub-cultivated every 2-3 days with seeding densities of $3\times10^5$-$2\times10^5$ cells/mL, respectively. Cells were grown in T-flask (Greiner). T-flasks were incubated in humidified incubators (Varolab) at 37° C. and 5% $CO_2$. The cell concentration and viability was determined by trypan blue exclusion using a counting chamber.

Fed-Batch Cultivation

Cells were seeded at $3\times10^5$ cells/ml into 125 ml shake flasks (Corning) in 30 ml of chemically defined, serum-free medium without antibiotics or MTX. The cultures were agitated at 120 rpm in 37° C. and 5% $CO_2$ in a minitron incubator (Infors) which was reduced to 2% following day 3. Feed solution was added daily from day 3 on and glucose was measured using the offline glucose analysis device "LaboTRACE" (Trace Analytics). At concentrations below 3 g/L, glucose (# G8769, Sigma-Aldrich) was adjusted to 5 g/L. Cell densities and viability were determined by trypan-blue exclusion using the "Countess 2 FL automated cell counter" (Life Technologies). Cumulative specific productivity was calculated as product concentration analyzed by ELISA at the given day divided by the "integral of viable cells" (IVC) until that time point.

Generation of Antibody-Producing Cells

CHO-DG44 cells (Urlaub G, et al., 1983. *Cell*. 33:405-412) were stably transfected with expression plasmids encoding the IgG1 antibody mAb1 (with a heavy chain with a sequence according to SEQ ID NO: 24 and a light chain sequence according to SEQ ID NO: 25) and are referred to as CHO-mAb1 herein. Selection was carried out by cultivation of transfected cells in the absence of Hypoxanthine and Thymidine and in the presence of the respective selective agents, for which a resistance cassette is encoded by the expression plasmids. After about 3 weeks of selection, stable cell populations are obtained and further cultivated according to a standard stock culture regime with subcultivation every 2 to 3 days. Increasing concentrations of methotrexate were added step-wise to increase mAb1 gene expression. In a next step, FACS-based single cell cloning of the stably transfected cell populations was carried out to generate monoclonal cell lines.

CHO-DG44 cells (Urlaub G, et al., 1983. *Cell*. 33:405-412) were alternatively stably transfected with expression plasm ids encoding the IgG1 antibody mAb2 (with a heavy chain with a sequence according to SEQ ID NO: 26 and a light chain sequence according to SEQ ID NO: 27) and are referred to as CHO-mAb2 herein. Selection was carried out by cultivation of transfected cells in the absence of hypoxanthine and thymidine and in the in the presence of the respective selective agents, for which a resistance cassette is encoded by the expression plasm ids. After about 3 weeks of selection, stable cell populations were obtained and further cultivated according to a standard stock culture regime with subcultivation every 2 to 3 days. Increasing concentrations of methotrexate were added step-wise to increase mAb2 gene expression. In a next step, ClonePixFL-based single cell cloning of the stably transfected cell populations was carried out to generate monoclonal cell lines.

Stably transfected CHO-mAb1 or CHO-mAb2 cells were cultivated in chemically defined, serum-free medium (Boehringer-Ingelheim) supplemented with G418 (Gibco, Life technologies). CHO-mAb1 cell medium was supplemented with 400 nM MTX and CHO-mAb2 cell medium was supplemented with 100 nM MTX (Sigma-Aldrich, Germany). Cells were subcultivated every 2 or 3 days with a seeding density of $3 \times 10^5$ cells/mL or $2 \times 10^5$ cells/mL.

Transient Expression of Human microRNAs in CHO Producer Cells

CHO-DG44 cells stably secreting an IgG1 antibody (mAb1) were cultivated in chemically defined, serum-free medium (Boehringer-Ingelheim) supplemented with G418 (Gibco, Life technologies) and 400 nM MTX (Sigma-Aldrich, Germany) and were subcultivated every 2 or 3 days with a seeding density of $3 \times 10^5$ cells/mL or $2 \times 10^5$ cells/mL.

Cells were transfected via nucleofection one day after subcultivation ($4 \times 10^5$ cells/sample) in 96-well Nucleofector kit SG (Lonza) containing 1 µM miRNA using the Amaxa 96-well Shuttle Device (Lonza) and program 96-DT-133 according to the manufacturer's instructions. For transient transfection a negative control miRNA miR-c #1 (miRIDIAN microRNA mimic negative control #1, Dharmacon) was used. Cells were then seeded with a density of $3 \times 10^5$ cells/mL into a 24-well flat bottom plate (Greiner). One day after transfection the volume of the medium was doubled by addition of fresh medium. Two days after transfection total RNA was extracted using the RNeasy Plus Mini Kit (Qiagen) and mRNA levels of target genes were determined by qPCR as described below.

Next Generation Sequencing

CHO-DG44 cells stably secreting an IgG1 antibody (mAb1) were transfected via nucleofection one day after subcultivation ($4 \times 10^5$ cells/sample) in 96-well Nucleofector kit SG (Lonza) containing 1 µM miRNA (miR-c #1, hsa-miR-1287 or hsa-miR-1978) using the Amaxa 96-well Shuttle Device (Lonza) and program 96-DT-133 as described above. 12 hours after transfection total RNA was extracted using RNeasy Plus Mini Kit (Qiagen) according to manufacturer's instructions and quality and quantity were analyzed with the 2100 Bioanalyzer (Agilent) using RNA 6000 Nano Kit. Subsequently, cDNA libraries were generated with 200 ng RNA using TruSeq RNA Sample Prep Kit v2 (Illumina) according to the manufacturer's instructions. Briefly, polyA+RNA was enriched, followed by random fragmentation of poly-A+ RNA (100-500 bp), synthesis of ds cDNA without strand specificity, ligation of barcode-labeled adapters per sample and amplification of asymmetrically ligated fragments. Quality and quantity was analyzed with a 2100 Bioanalyzer (Agilent) using DNA 1000 Kit. The cDNA library was loaded with 9 pmol per lane on a full flow cell on a HiSeq 2000 sequencing instrument (Illumina) with single-read mode and 60 cycles of fragment sequencing plus 7 cycles of barcode sequencing. Sequence reads per sample were mapped with TopHat software against the reference genome from Cricetulus griseus (assembly "CriGri_1.0" https://www.ncbi.nlm.nih.gov/assembly/309608). Quantification was carried out according to Mortazavi et al. (Nature Methods—5, 621-628 (2008)). Thus, transcript abundance is calculated as RPKM (=reads per kilobase of exon model per million mapped reads).

Transient Expression of Human siRNAs in CHO Producer Cells

CHO-mAb1 cells and CHO-mAb2 cells were cultivated in chemically defined, serum-free medium (Boehringer-Ingelheim) supplemented with 400 nM MTX (Sigma-Aldrich, Germany) and 100 nM MTX, respectively, and G418 (Gibco, Life technologies). Cells were subcultivated every 2 or 3 days with a seeding density of $3 \times 10^5$ cells/mL or $2 \times 10^5$ cells/mL.

Cells were transfected via nucleofection one day after subcultivation ($4 \times 10^5$ cells/sample) in 96-well Nucleofector kit SG (Lonza) containing 2 µM siRNA using the Amaxa 96-well Shuttle Device (Lonza) and program 96-DT-133 according to the manufacturer's instructions. Cells were then seeded with a density of $3 \times 10^5$ cells/mL into a 24-well flat bottom plate (Greiner). One day after transfection the volume of the medium was doubled by addition of fresh medium. Two days after transfection total RNA was extracted using the RNeasy Plus Mini Kit (Qiagen) and mRNA levels of target genes ATF6B, CERS2 and TBC1D20 were determined by qPCR as described below. Supernatants were collected at day 1-4 post transfection and stored at −20° C. until antibody measurement by ELISA. Negative control cells were transfected with water instead of siRNA (mock control) or with a non-targeting negative control pool (NT siRNA) having the following sequences: UGGUUUACAUGUCGACUAA, UGGUUUACAUGUUUUCUGA, UGGUUUACAUGUUUUCUGA and, UGGUUUACAUGUUUUCCUA (SEQ ID NOs: 38-41, respectively) (Dharmacon, # D-001810-10).

ATF6B, CERS2, TBC1D20, GRP78, CHOP and Herpud1 RNA Expression Measurement by qPCR Analysis Total RNA of $2 \times 10^5$ to $2 \times 10^6$ cells was extracted using the RNeasy Plus Mini Kit (Qiagen). cDNA was generated with 100 ng RNA using the Quantitect Reverse Transcription Kit (Qiagen) according to the manufacturer's instructions. qPCR was performed with the DyNAmo ColorFlash SYBR Green qPCR Kit (Thermo Scientific) in a white 96-well PCR plate (Biorad) using a Cfx96 device (Biorad). Beta actin was used as reference gene. Calculation was done with the single threshold method and ΔΔCq values were calculated (Bio-rad CFX manager software 2.1).

TABLE 4

Primers used in qPCR analysis

| Target | Forward primer 5'-3' | Reverse primer 5'-3' |
|---|---|---|
| Atf6b | GAGCAGGATGTCCCGTTTG A (SEQ ID NO: 42) | AGCTCAGGGAGGAGGAAGAG (SEQ ID NO: 43) |
| Tbc1D20 | CCCTGAACAGTGATCCCAC C (SEQ ID NO: 44) | ATCCTTCCTTGACACAGGCG (SEQ ID NO: 45) |
| CerS2 | CCCATACAGAGCATCGTCC C (SEQ ID NO: 46) | GGCAAACCAGGAGAAGCTGA (SEQ ID NO: 47) |
| CHOP | GACCCTGTTTCTTTCCCTT CAG (SEQ ID NO: 48) | GGACTGGGTTCTGCTTTCAG G (SEQ ID NO: 49) |
| GRP78 | ACCACCTATTCCTGCGTTG G (SEQ ID NO: 50) | AGACCGTGTTCTCGGGATTG (SEQ ID NO: 51) |
| Herpud1 | GAAGAGTCCCAACCAGCGT C (SEQ ID NO: 52) | ATGTCGCTTTTCCTGCTTTG G (SEQ ID NO: 53) |

Determination of Recombinant Antibody Concentration

To assess recombinant antibody production in transfected cells, supernatants were collected from cell cultures at the given time points. The product concentration was then analyzed by enzyme linked immunosorbent assay (ELISA). First, high binding 96-well microplates (Greiner) were coated with an antibody against the human IgG Fc fragment (Jackson Immuno Research Laboratories) in a 1:480 dilution at 4° C. overnight. After washing three times with 0.15% Tween 20 in PBS (pH 7.4) the plates were incubated with blocking buffer (1% BSA in PBS, pH 7.4) for one hour at room temperature, followed by three washing steps. Supernatants were diluted to an appropriate concentration in the range of the standard curve (1-50 ng/μL or 1-100 ng/μl) in dilution buffer (0.5% BSA, 0.01% Tween 80 in PBS, pH 7.4). As a standard, mAb1 antibody was used in a serial dilution from 0-100 ng/μL. Diluted samples and standards were incubated for 1.5 hours at room temperature. After repeated washing, the samples were incubated with a HRP-conjugated antibody against the human kappa light chain (Sigma) in a 1:5000 dilution for one hour at room temperature, followed by three washing steps. The substrate p-nitrophenylphosphate (Sigma Aldrich) was freshly prepared in a concentration of 1 mg/mL with 0.1 M glycine, 1 mM $ZnCl_2$ and 1 mM $MgCl_2$ (pH 10.4) and incubated for 20 minutes in the dark. The reaction was stopped by addition of 3 M NaOH and absorption at 405 nm and at a reference wavelength of 492 nm was measured using the Infinite M200 Pro multimode reader (Tecan).

Stable Overexpression of microRNAs miR-1287 and miR-1978

The BLOCK-iT™ Pol II miR RNAi expression vector kit (pcDNA6.2-GW/emGFP-miRNA expression system kit) was used for stably expressing miRNAs. DNA oligonucleotides encoding two copies of a specific microRNA were cloned as short hairpins into the mammalian expression vector pcDNA6.2. For that purpose, DNA oligonucleotides encoding the respective miRNAs were designed as described in the manual. In brief, the mature miRNA sequence was embedded in a given sequence including an optimized hairpin loop sequence and 3' and 5' flanking regions derived from the murine miRNA mir-155 (Lagos-Quintana et al., 2002). The flanking regions were present on the vector and a DNA oligonucleotide was designed, which encodes the miRNA sequence, the mentioned loop and the antisense sequence of the respective mature miRNA with a 2 nucleotide depletion to generate an internal loop in the hairpin stem. Furthermore, overhangs were added for cloning at both ends. Hairpin structure may be analyzed using the online tool mfold (M. Zuker. Mfold web server for nucleic acid folding and hybridization prediction. *Nucleic Acids Res.* 31 (13), 3406-3415, 2003). DNA strands were annealed and ligated into the 3'-UTR of emerald GFP reporter protein gene as described by the manufacturer. The oligonucleotide sequences used for cloning of miRNAs into the vector backbone were as follows:

hsa-miR-1287 oligonucleotide forward:
(SEQ ID NO: 28)
TGCTGTGCTGGATCAGTGGTTCGAGTCGTTTTGGCCACTGACTGACGACT

CGAACCACATCCAGCA hsa-miR-1287 oligonucleotide reverse:
(SEQ ID NO: 29)
CCTGTGCTGGATGTGGTTCGAGTCGTCAGTCAGTGGCCAAAACGACTCGA

ACCACTGATCCAGCAC

-continued
hsa-miR-1978 oligonucleotide forward:
(SEQ ID NO: 30)
TGCTGGGTTTGGTCCTAGCCTTTCTAGTTTTGGCCACTGACTGACTAGAA

AGGCTAACCAAACC hsa-miR-1978 oligonucleotide reverse:
(SEQ ID NO: 31)
CCTGGGTTTGGTTAGCCTTTCTAGTCAGTCAGTGGCCAAAACTAGAAAGG

CTAGGACCAAACCC

A vector containing more than one miRNA was generated applying the chaining technique. For one miRNA with two copies, two copies of specific microRNAs (e. g. hsa-miR1287 or miR-1978 indicated by pcDNA6.2-GW/emGFP-miR1287-miR1287 or pcDNA6.2-GW/emGFP-miR1978-miR1978) were cloned as DNA oligonucleotides encoding said miRNAs as short hairpins into the mammalian expression vector pcDNA6.2-GW/emGFP-miRNA (BLOCK-iT™ Pol II miR RNAi expression vector kit, K4936-00 from life technologies) as described by the manufacturer. In brief, the miRNA cassette was excised with the enzymes BamHI and XhoI. The vector containing already one miRNA was opened with the enzymes BglII and XhoI. DNA was mixed with orange loading buffer and was separated in a 1% agarose gel prepared with TAE buffer, bands were visualized with ethidium bromide and bands of appropriate size were excised from the gel. Size was verified with DNA ladder. DNA was eluted with the gel extraction kit. DNA insert was ligated into the vector using T4 DNA ligase according to manufacturer's instructions. Subsequently, competent *E. coli* were transformed with the DNA and plated on agar plates containing spectinomycin. Colonies were picked and DNA was extracted with a DNA purification kit, checked by control digest with BamHI and BglII first, followed by sequencing.

For generation of stable cell pools CHO-mAb1 were transfected with Lipofectamine 2000 and Plus reagent (Invitrogen) using an optimized protocol with pcDNA6.2-GW/emGFP-miR-1287-1287 or pcDNA6.2-GW/emGFP-mi-1978-1978 as described by the manufacturer and cells were selected with 10 μg/mL blasticidin S (Life Technologies) and enriched for GFP positive cells by FACS (FACS Diva). As a control vector a negative control miRNA expressing vector (pcDNA6.2-GW/emGFP-neg. control miRNA, provided by the kit) expressing GFP was stably transfected as described. The negative control miRNA has the following sequence: GAAAUGUACUGCGCGUGGAGAC (SEQ ID NO: 34)

Stable shRNA-Mediated Knockdown of ATF6B, CERS2 and TBC1D20

The BLOCK-iT™ Pol II miR RNAi expression vector kit (pcDNA6.2-GW/emGFP-miRNA expression system kit) was used for stably expressing shRNAs. DNA oligonucleotides encoding specific shRNAs were cloned as short hairpins into the mammalian expression vector pcDNA6.2. For that purpose, DNA oligonucleotides encoding the respective shRNAs were designed and cloned into the integrating vector, as described above for the cloning of miRNAs. The oligonucleotide sequences used for cloning of shRNAs into the vector backbone were as follows, wherein the underline indicates the antisense target site and its complementary sequence with a deletion of two nucleotides, respectively, connected with a loop sequences:

```
shTBC1D20#1 oligonucleotide forward:
                                          (SEQ ID NO: 16)
TGCTGAATCCTTGCTCAACTGTCGAAGTTTTGGCCACTGACTGACTTCGA

CAGGAGCAAGGATT shTBC1D20#1 oligonucleotide reverse:
                                          (SEQ ID NO: 17)
CCTGAATCCTTGCTCCTGTCGAAGTCAGTCAGTGGCCAAAACTTCGACAG

TTGAGCAAGGATTC shCERS2#1 oligonucleotide forward:
                                          (SEQ ID NO: 18)
TGCTGTTAAGTTCACAGGCAGCCATAGTTTTGGCCACTGACTGACTATGG

CTGTGTGAACTTAA shCERS2#1 oligonucleotide reverse:
                                          (SEQ ID NO: 19)
CCTGTTAAGTTCACACAGCCATAGTCAGTCAGTGGCCAAAACTATGGCTG

CCTGTGAACTTAAC shCERS2#2 oligonucleotide forward:
                                          (SEQ ID NO: 20)
TGCTGTGATGTAGAGGTCTGAGGCTTGTTTTGGCCACTGACTGACAAGCC

TCACCTCTACATCA shCERS2#2 oligonucleotide reverse:
                                          (SEQ ID NO: 21)
CCTGTGATGTAGAGGTGAGGCTTGTCAGTCAGTGGCCAAAACAAGCCTCA

GACCTCTACATCAC shATF6B#1 oligonucleotide forward:
                                          (SEQ ID NO: 22)
TGCTGTCCATCTTCACACTGAGGACCGTTTTGGCCACTGACTGACGGTCC

TCAGTGAAGATGGA shATF6B#1 oligonucleotide reverse:
                                          (SEQ ID NO: 23)
CCTGTCCATCTTCACTGAGGACCGTCAGTCAGTGGCCAAAACGGTCCTCA

GTGTGAAGATGGAC shATF6B#2 oligonucleotide forward:
                                          (SEQ ID NO: 35)
TGCTGTTCACTTCCAGAACCTCCTCTGTTTTGGCCACTGACTGACAGAGG

AGGCTGGAAGTGAA shATF6B#2 oligonucleotide reverse:
                                          (SEQ ID NO: 36)
CCTGTTCACTTCCAGCCTCCTCTGTCAGTCAGTGGCCAAAACAGAGGAGG

TTCTGGAAGTGAAC
```

As a control vector a negative control miRNA (SEQ ID NO: 34) expressing vector (pcDNA6.2-GW/emGFP-neg. control miRNA, provided by the kit) expressing GFP was stably transfected as described.

A vector containing more than one shRNA (pcDNA6.2-GW/emGFP-shTbc1D20-shCerS2#1 and pcDNA6.2-GW/emGFP-shCerS2#2-shTbc1D20) was generated applying the chaining technique as described above.

For generation of stable cell pools CHO-mAb2 cells were transfected one day after subcultivation via nucleofection with the Cell Line Nucleofector Kit V (Lonza) according to the manufacturer's instructions. In brief, 5×10$^6$ cells/sample were resuspended in 100 µL Solution V (Lonza) containing 5 µg plasmid DNA and nucleofected in a cuvette using the Cell Line Nucleofector Device (Lonza) and program H14. Cells were then seeded with 5 mL prewarmed chemically defined, serum-free medium without antibiotics into a T25-flask. 72 hours after transfection the medium was changed to chemically defined, serum-free medium containing 1 µg/mL blasticidin S (Life Technologies) for selection. 14 days after transfection cells were enriched for GFP positive cells by FACS (BD FACS Aria III). Efficient knockdown of ATF6B, CERS2 and TBC1D20 was monitored by qPCR as described before and cells were analyzed by flow cytometry (Miltenyi MacsQuant) for GFP expression after 42 days in culture.

Knockout of ATF6B, CERS2 and TBC1D20

To generate knockout cells depleted of ATF6B, CERS2 or TBC1D20, the CRISPR/Cas9 technology was applied. For gRNA design, target sites in the genomic loci of interest selected upstream of protospacer adjacent motifs (PAM) in the first exons present in all transcript variants of the respective genes. For each target gene three gRNA sequences were designed and cloned into the GeneArt® CRISPR Nuclease Vector with OFP Reporter (Life Technologies) containing a Cas9 nuclease and OFP expression cassette driven by a CMV promoter and a guide RNA (gRNA) cloning cassette. The guide RNA (consisting of a crRNA specific for the target site and a trans activating RNA) expression is driven by a U6 polII type promoter. Subsequently, competent *E. coli* were transformed with the DNA and plated on agar plates containing Ampicillin. Colonies were picked and DNA was extracted with a DNA purification kit and integrity of the plasmid was analyzed by sequencing. For generation of stable cells, CHO-mAb2 cells were transfected one day after subcultivation via nucleofection with the Cell Line Nucleofector Kit V (Lonza) as described before. Cleavage efficiency was detected using the GeneART® Genomic Cleavage Detection Kit (Life Technologies) according to the manufacturer's instructions. To generate stable cell clones CHO-mAb2 cells were transfected with the described gRNA and Cas9 containing vector and a CMV promoter driven puromycin or alternatively fluorescence marker gene embedded in flanking regions complementary to genomic regions flanking the target site of interest. Efficient target site cleavage followed by homology directed repair (HDR) based integration of the selection marker gene allows for antibiotic selection and FACS sorting, respectively. Cells with knockout in the ATF6B, CERS2 or TBC1D20 gene were thereby selected and cultured in chemically defined, serum-free medium (Boehringer Ingelheim).

Antibody Purification

The antibody was purified from cell-free cell culture supernatant using RoboColumns (Atoll) filled with MabSelect resin (GE Healthcare) run on a pipetting robot. The low pH used for elution was neutralized to pH 5.5 with 1 M TRIS to prevent for antibody denaturation. As amino groups interfere with the glycosylation analysis, the buffer was exchanged by ultrafiltration using 10 kDa MWCO PES Vivaspin 500 filter units (Sartorius) to pure water. The final protein concentration was determined using a NanoDrop 2000 c photospectrometer (Thermo Scientific).

Analysis of the Glycosylation Pattern

To elucidate the structure and composition of the Fc-glycosylation of IgGs produced in the shRNA expressing CHO-mAb2 cell pools described in Examples 10 and 11, the glycans were released from the purified antibody after reduction by enzymatic digestion with PNGase F. The composition of the Fc-glycosylation of the IgG antibody was analyzed after PNGaseF release and fluorescent labelling using microchip-based capillary electrophoresis (CE) with the ProfilerPro Glycan Profiling system on a LabChip GXII instrument (PerkinElmer) according to the manufacturer's protocol. Electropherograms were analyzed by the LabChip GX software to identify and quantify the individual sugar structures. The percentage of the glycol-forms was calculated from the chromatographic peak areas. All values were normalized to 100% total sugar structures per sample.

EXAMPLES

Example 1: Transcriptome Profiling by Next Generation Sequencing (NGS)

CHO cells are commonly used for the production of therapeutic proteins. Genetic engineering approaches have attempted to optimize the productivity of these cells by expressing specific cDNAs. Naturally existing non-coding RNAs regulate cell fate by modulating the expression of a whole set of target proteins, which may possibly result in a super-secretory phenotype when over-expressed in CHO producer cells. To exploit the power of non-coding RNAs and to identify those that positively affect secretion of a heterologous therapeutic protein, CHO-mAb1 cells were transfected with a library of human microRNAs. Based on this genome-wide functional microRNA (miRNA) screen to identify miRNAs that enhance the antibody productivity of CHO-mAb1 cells, the two miRNA screen hits miR-1287 (SEQ ID NO: 32) and miR-1978 (SEQ ID NO: 33) with strong effects on antibody production and specific productivity were chosen for further analysis (FIG. 1). To identify direct miRNA target genes responsible for the positive effects on CHO cell productivity, CHO-mAb1 cells were transiently transfected with each of the two miRNAs. Cells were transfected via nucleofection one day after subcultivation ($4 \times 10^5$ cells/sample) in 96-well Nucleofector Kit SG (Lonza) as described above. Cells were then seeded with a density of $3 \times 10^5$ cells/mL into a 24-well plates (Greiner). 12 hours after transfection cells were analyzed by transcriptome profiling using next generation sequencing (NGS) as described above.

Genes that were significantly downregulated with a |log 2| of their expression fold change>1 (expression more than 2 fold in untransfected cells) were defined as hits. Candidate miRNA target genes were then selected for further analysis with reference to existing knowledge about relevant pathways. ATF6B was chosen as target gene of miR-1287 with the assumption that its downregulation triggers the unfolded protein response (UPR). Both, CERS2 and TBC1D20 were chosen as target genes of miR-1978 being involved in the regulation of vesicular and non-vesicular protein secretion, respectively. Their effects on antibody production and specific productivity were first assessed by siRNA-mediated gene knockdown. Recapitulating the positive effects on specific productivity in the transient approach, long-term depletion of the target genes was obtained by shRNAs. Names and sequences of the siRNAs and shRNAs are listed in FIG. 1B.

Example 2: Selected NGS Hits are Validated by qPCR Analysis

Figure 2A:
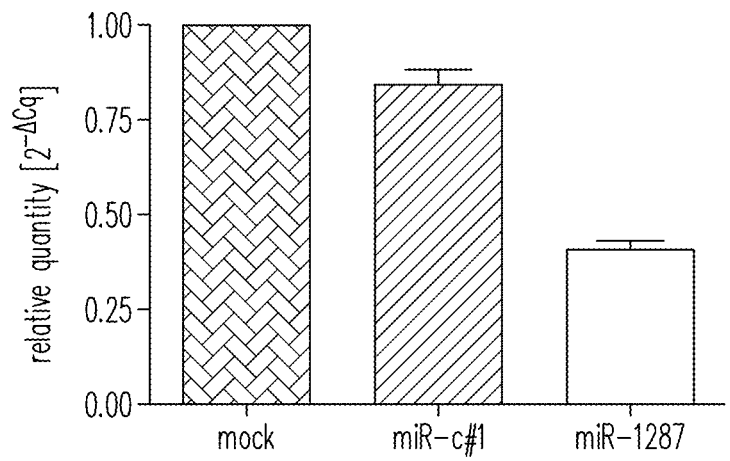
Figure 2B:
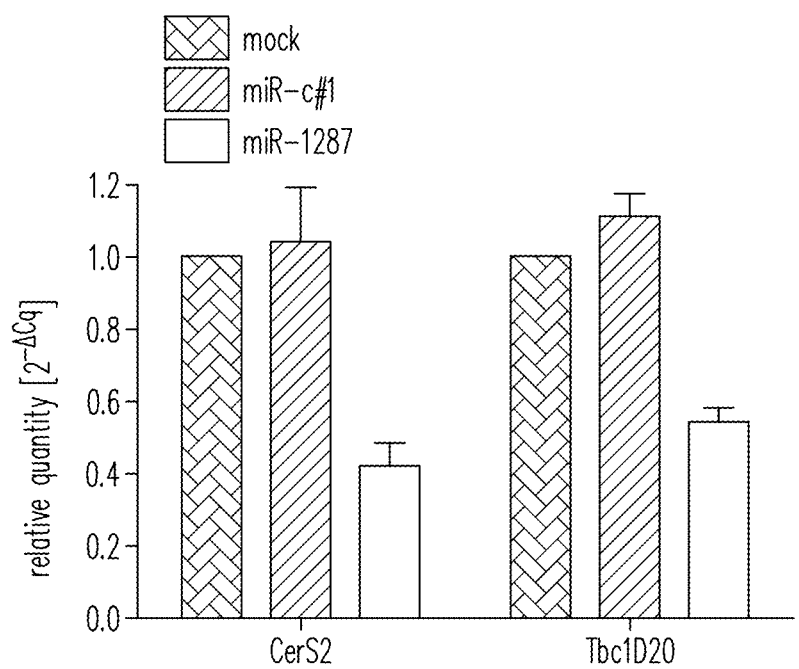
Figure 2C:
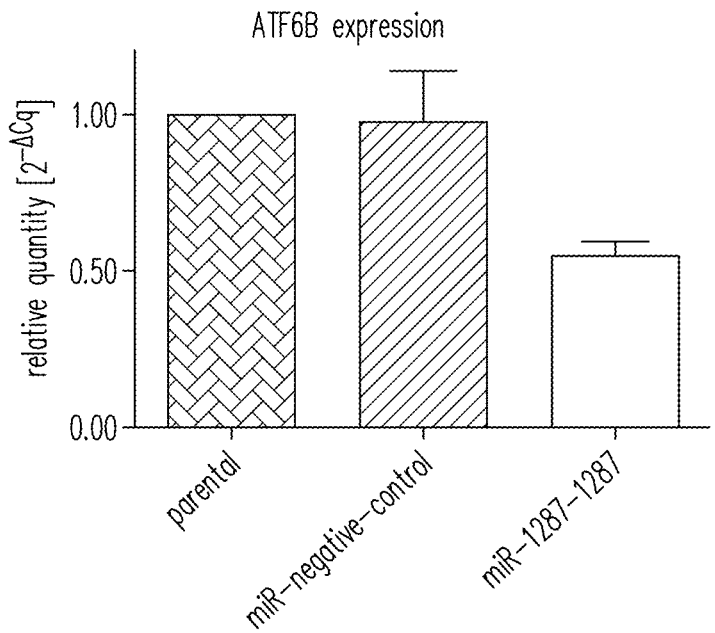
Figure 2D:
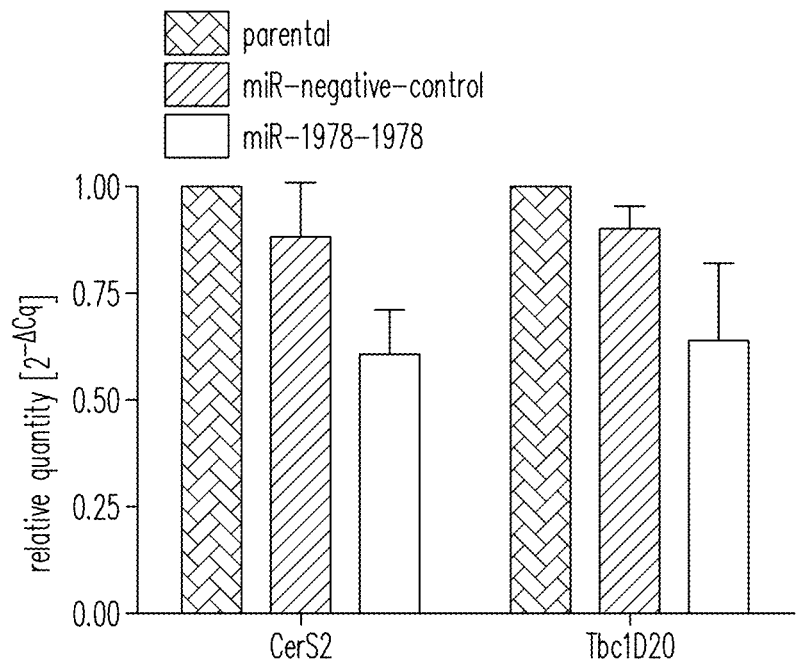

To validate the NGS hits ATF6B and CERS2/TBC1D20 as direct target genes of the miRNAs miR-1287 and miR-1978, respectively, their expression level was analyzed by qPCR. CHO-mAb1 cells were transfected with each of the two microRNAs as described above. One day after transfection, RNA was extracted to measure levels of mRNA of ATF6B, CERS2 or TBC1D20 by qPCR analysis (FIGS. 2A and B) as described above. Relative expression was calculated by normalizing to the reference gene beta actin. Additionally, changes in the expression level of the genes of interest were analyzed by qPCR in CHO-mAb1 cells stably overexpressing the respective miRNAs. These cell pools were generated by transfecting CHO-mAb1 cells with a GFP-containing expression vector further encoding miR-1287 or miR-1978 (pcDNA6.2-GW/emGFP-miR-1287-1287 and pcDNA6.2-GW/emGFP-miR-1978-1978) (FIGS. 2C and D). Both, CHO-mAb1 cells transiently and stably expressing miR-1287 showed a reduced expression level of ATF6B, indicating a direct targeting by the miRNA. CHO-mAb1 cells expressing miR-1978 transiently as well as cell pools with stable miR-1978 overexpression showed decreased mRNA levels of CERS2 and TBC1D20. Thus, all the three NGS hits were validated as direct target genes of the respective miRNAs.

Example 3: Effective siRNA Mediated Knockdown of ATF6B, CERS2 and TBC1D20

Expression of miR-1287 and miR-1978 strongly improved the specific productivity of a recombinant antibody expressing CHO cell line (CHO-mAb1). To investigate if the depletion of the validated miR-1287 target gene ATF6B and the validated miR-1978 targets CERS2 and TBC1D20 also positively affects the specific productivity of recombinant antibody producing CHO cells, CHO-mAb1 cells were transfected with siRNAs specific for the respective target mRNAs. Three independent siRNAs were used for downregulation of ATF6B and two siRNAs for CERS2 and TBC1D20, respectively. One day after transfection RNA was extracted and mRNA levels of ATF6B, CERS2 and TBC1D20 were quantified by qPCR analysis. Relative expression was calculated by normalizing to the reference gene beta actin (FIG. 3). CHO-mAb1 cells transiently transfected with siRNAs specific for ATF6B had strongly reduced levels of ATF6B mRNA compared to untransfected control cells (and compared to cells transfected with non-targeting control siRNA in a separate experiment, data not shown). The knockdown efficiency was similar for all three independent siRNAs. Transient transfection of CHO-mAb1 cells with siRNA specific for CERS2 and siRNA specific for TBC1D20 in combination resulted in reduced expression of CERS2 and TBC1D20 in comparison to untransfected control cells (and compared to cells transfected with non-targeting control siRNA in a separate experiment, data not shown). Thus, all the siRNAs for ATF6B and for CERS2 as well as for TBC1D20 induced an effective knockdown of the respective target genes.

Example 4: siRNA-Mediated Knockdown of ATF6B Increases the Specific Productivity of CHO-mAb1 Cells To investigate if the knockdown of ATf6B improves the specific productivity of CHO-mAb1 cells stably expressing the mAb1 antibody cells were transfected with three independent siRNAs specific for ATF6B (siAtf6b #1 (SEQ ID NO: 9), siAtf6b #2 (SEQ ID NO: 10) and siAtf6b #3 (SEQ ID NO: 11)). The cells were cultivated for four days in a total volume of 1 mL (24 well format) with triplicate samples. Antibody concentrations in the supernatant of the transfected cells were determined on day 3 and 4 post transfection by ELISA as described above. In addition, cell density and viability were determined each day as described above, enabling the calculation of the specific productivity. Knockdown of ATF6B resulted in an improved specific productivity at day 4 (FIG. 4), compared to untransfected control cells (and compared to cells transfected with non-targeting control siRNA in a separate experiment, data not shown).

Example 5: Combined siRNA-Mediated Knockdown of CERS2 and TBC1D20 Increases the Specific Productivity of CHO-mAb1 Cells Up to 1,5-Fold To explore whether the knockdown of the two miR-1978 targets CERS2 and TBC1D20 has a positive impact on the specific productivity of CHO-mAb1 cells, these cells were first transfected with specific siRNAs for either CERS2 or TBC1D20 and in a second experiment cells were transfected with both siRNAs together. The experiment was conducted as described in Example 4. Determination of the specific productivity at day 3 and 4 revealed that a single knockdown of either CERS2 or TBC1D20 only slightly improved the specific productivity whereas a combined knockdown of the two target genes increased specific productivity up to 1.5 fold (FIG. 5).

Example 6: Three Independent siRNAs for ATF6B Improve Specific Productivity of CHO-mAb2 Cells To explore whether the increased specific productivity was specific to mAb1-producing CHO cells or could equally be seen in another IgG-producing CHO cell line, CHO-mAb2 cells were transiently transfected with each of the three independent siRNAs specific for ATF6B, siAtf6b #1 (SEQ ID NO: 9), siAtf6b #2 (SEQ ID NO: 10), siAtf6b #3 (SEQ ID NO: 11). The experiment was conducted as described in Example 4. Remarkably, all the three siRNAs increased the specific productivity at day 3 and 4 post transfection 1.2-1.6 fold (FIG. 6).

Example 7: Combined Knockdown of CERS2 and TBC1D20 Improves Specific Productivity of CHO-mAb2 Cells Furthermore, we were interested if the combined knockdown of CERS2 and TBC1D20 also leads to an increased specific productivity of CHO-mAb2 cells. The experiment was conducted as described in Example 4 using siRNA specific for TBC1D20, siTbc1D20#1 (SEQ ID NO:7) and siRNA specific for CERS2, siCerS2#1 (SEQ ID NO: 8). Similar to CHO cells stably expressing the mAb1 antibody, specific productivity was increased up to 1.5 fold compared to mock transfected control cells (FIG. 7), providing evidence that this improvement by transient downregulation of CERS2 and TBC1D20 is independent of the cell clone, the medium and the antibody produced.

A similar increase in specific productivity was also observed for CHO-DG44 cells stably expressing human serum albumin (data not shown).

Example 8: Analysis of shRNA Expression in CHO-mAb2 Cells by Flow Cytometry

CHO-mAb2 cells were stably transfected with a plasmid encoding a GFP cassette plus a shRNA sequence comprising a nucleotide sequence specifically targeting ATF6B (shAtf6b #1; SEQ ID NO: 15) or a combination of two individual shRNA sequences comprising sequences specifically targeting CERS2 (shCerS2#1; SEQ ID NO: 13 and shCerS2#2; SEQ ID NO: 14) and TBC1D20 (shTbc1D20#1; SEQ ID NO: 12) (pcDNA6,2-GW/emGFP-shAtf6b #1, pcDNA6,2-GW/emGFP-shTbc1D20#1-shCerS2#1 and pcDNA6,2-GW/emGFP-shCerS2#2-shTbc1D20#1). After selection with blasticidin S (the blasticidin resistance gene is encoded by the pcDNA6,2-GW/emGFP vector) cells were sorted based on their GFP fluorescence. Control cells were untransfected parental cells. To validate the expression of stably transfected shRNAs, cells were analyzed by flow cytometry for GFP expression, which correlates with shRNA expression, and GFP positive populations were detected for at least 42 days (FIG. 8). This shows that CHO cells are able to stably overexpress shRNAs for at least 6 weeks.

Example 9: Analysis of shRNA Expression in Stably Transfected IgG-Producing CHO Cells by Quantitative PCR CHO-mAb2 cells were stably transfected with a plasmid encoding a GFP cassette plus a shRNA sequence comprising a nucleotide sequence specifically targeting ATF6B or a combination of two individual shRNA sequences comprising sequences specifically targeting CERS2 and TBC1D20 (pcDNA6.2-GW/emGFP-shAtf6b #1, pcDNA6.2-GW/emGFP-shTbc1D20#1-shCerS2#1 or pcDNA6.2-GW/emGFP-shCerS2#2-shTbc1D20#1), as described above. After selection with blasticidin S (the resistance gene is encoded on the pcDNA6.2-GW/emGFP vector) cells were sorted based on their GFP fluorescence. Cell pools stably expressing the control vector (pcDNA6.2-GW/emGFP-neg. control) and untransfected parental cells served as negative controls. To validate the expression of stably transfected shRNAs, we isolated RNA from all cells and performed qPCR analysis of the ATF6B, CERS2 and TBC1D20 mRNA level, respectively, as described above. Compared to control vector transfected cells and parental cells the cells transfected with shRNA-encoding plasmids had reduced levels of mRNA of ATF6B or reduced levels of mRNA of both CERS2 and TBC1D20 (FIG. 9). This demonstrates that stable genomic integration of plasmid-encoded shRNAs leads to decreased levels of the respective target gene in CHO cells.

Example 10: Fed-Batch Cultivation of CHO-mAb2 Cells Stably Expressing a shRNA for ATF6B CHO-mAb2 cells were stably transfected with expression vectors containing a shRNA sequence comprising a nucleotide sequence specifically targeting ATF6B (pcDNA6.2-GW/emGFP-shAtf6b #1) and cells were sorted based on their GFP expression, as described above. One pool of cells expressing a shRNA sequence targeting ATF6B and two independent pools of cells transfected with a negative control vector were used during fed-batch cultivation. Cell density, viability and product formation (µg/ml) was determined on days 3-6 by cell counting with trypan blue exclusion and ELISA analysis, respectively, as described above. Specific productivity was calculated. Interestingly, cells expressing a shRNA specific for ATF6B showed improved antibody titer, improved specific productivity and an increased viable cell density compared to the cells transfected with a negative control vector (FIG. 10). Further, cell viability was unaltered (data not shown). This proves that stable pools of CHO cells depleted of ATF6B have an

Example 11: Fed-Batch Cultivation of CHO-mAb2 Cells Stably Expressing a Combination of shRNAs Specific for CERS2 and TBC1D20

CHO-mAb2 cells were stably transfected with expression vectors containing shRNA sequences comprising sequences specifically targeting CERS2 and TBC1D20 (pcDNA6.2-GW/emGFP-shTbc1D20#1-shCerS2#1 or pcDNA6.2-GW/emGFP-shCerS2#2-shTbc1D20#1) and cells were sorted based on their GFP expression, as described above. Two independent combinations of shRNAs targeting the CERS2 and TBC1D20 mRNAs and two independent pools of cells transfected with a negative control vector were used during fed-batch cultivation in two independent experiments. Cell density, viability and product formation was determined on days 3-11 by cell counting with trypan blue exclusion and ELISA analysis, respectively, as described above. Specific productivity was calculated. Both cell pools expressing shRNAs against CERS2 and TBC1D20 showed improved antibody expression and specific productivity compared to the cell pools transfected with the negative control vector (FIG. 11). This proves that stable pools of CHO cells depleted of both CERS2 and TBC1D20 have an increased titer and specific productivity capacity.

Example 12: Analysis of Antibody Glycosylation and Antibody Aggregate Formation To analyse product quality we first analysed the structure and composition of the Fc-glycosylation of IgGs produced in the shRNA expressing CHO-mAb2 cell pools described in Examples 10 and 11 above. The glycans were released from the purified antibody after reduction by enzymatic digestion with PNGase F. The composition of the Fc-glycosylation of the IgG antibody was analyzed after PNGaseF release and fluorescent labelling using microchip-based capillary electrophoresis (CE) with the ProfilerPro Glycan Profiling system on a LabChip GXII instrument (PerkinElmer) according to the manufacturer's protocol. Electropherograms were analyzed by the LabChip GX software to identify and quantify the individual sugar structures. The percentage of the glycol-forms was calculated from the chromatographic peak areas. All values were normalized to 100% total sugar structures per sample. The results in FIG. 12 show that the depletion of ATF6B (FIG. 12A), CERS2 and TBC1D20 (FIG. 12B) did not affect glycosylation of the mAb2 antibody. In addition to antibodies purified from cells expressing shAtf6b #1, no change in antibody glycosylation was observed in antibodies purified from cells expressing shAtf6b #2 (data not shown).

Figure 12A:
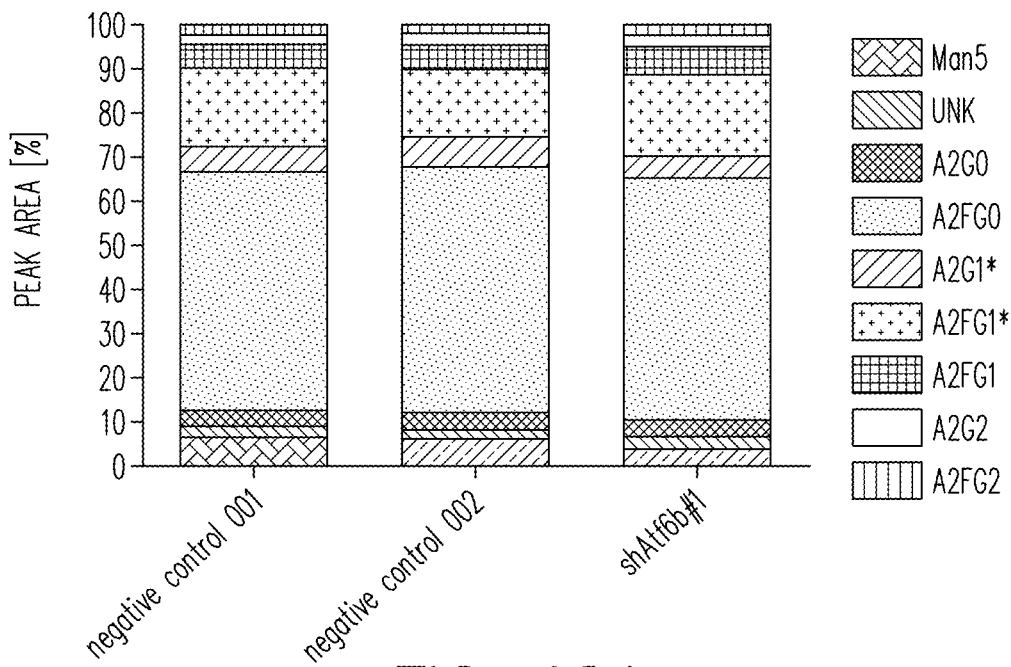
Figure 12B:
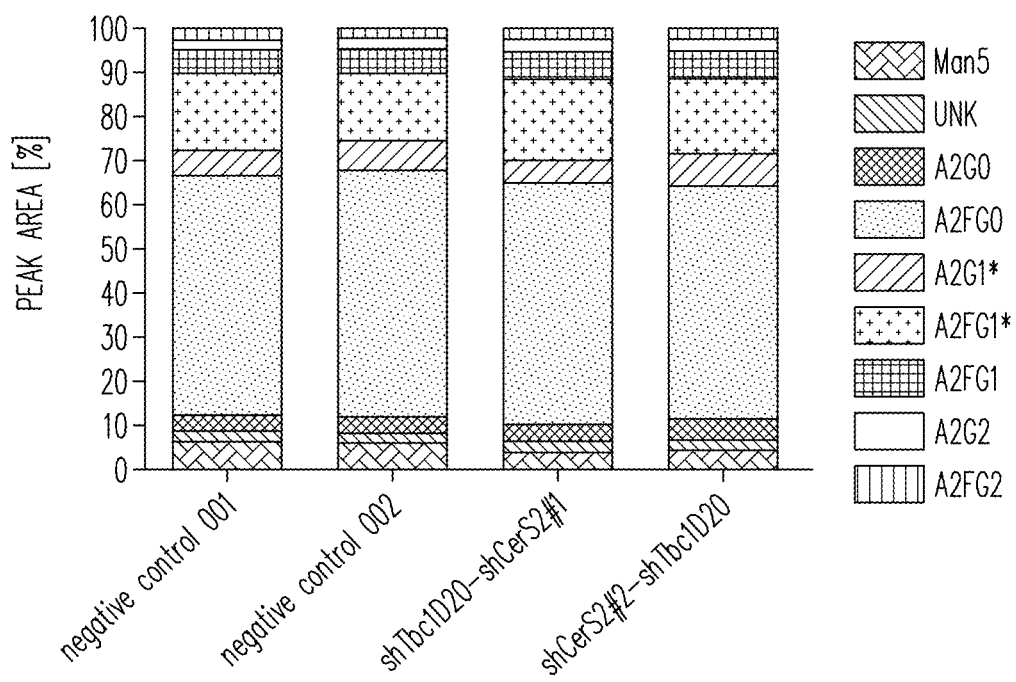
Figure 12C:
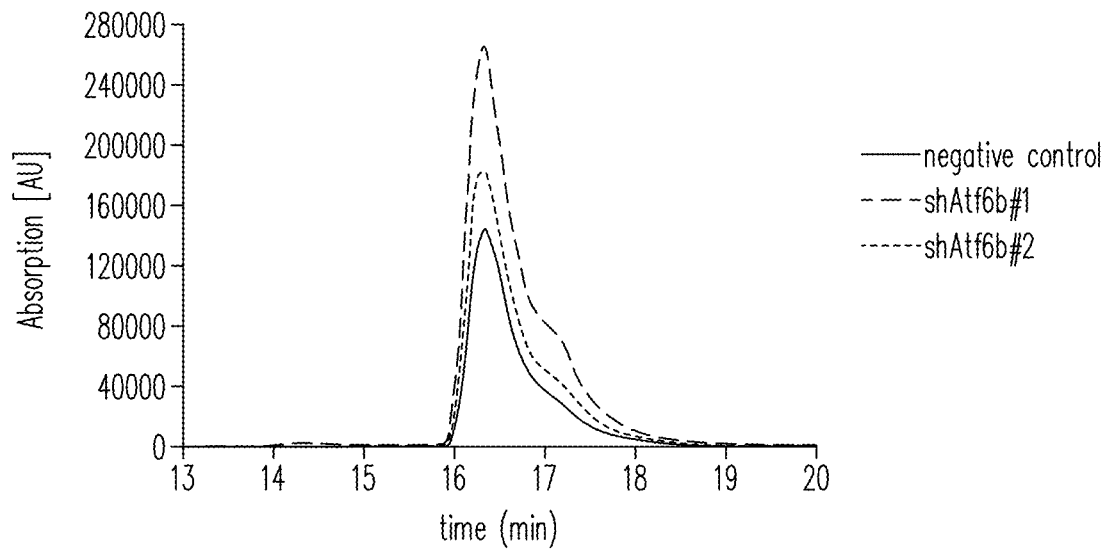

To further prove that product quality was maintained, the formation of aggregates was analyzed by HPLC at the end of the fed-batch run. CHO-mAb2 cells, stably expressing shAtf6b #1 or shAtf6b #2 (pcDNA6.2-GW/emGFP-shAtf6b #1 or pcDNA6.2-GW/emGFP-shAtf6b #2) or a negative control sequence were cultivated under fed-batch conditions for 7 days. The secreted antibody was purified from the supernatants and analyzed by HPLC. FIG. 12C shows that the antibody preparations from the different cells (shAtf6b #1 or shAtf6b #2 expressing cells as well as the negative controls) were very similar, with a proportion of aggregates of less than 1.5%.

Figure 12D:
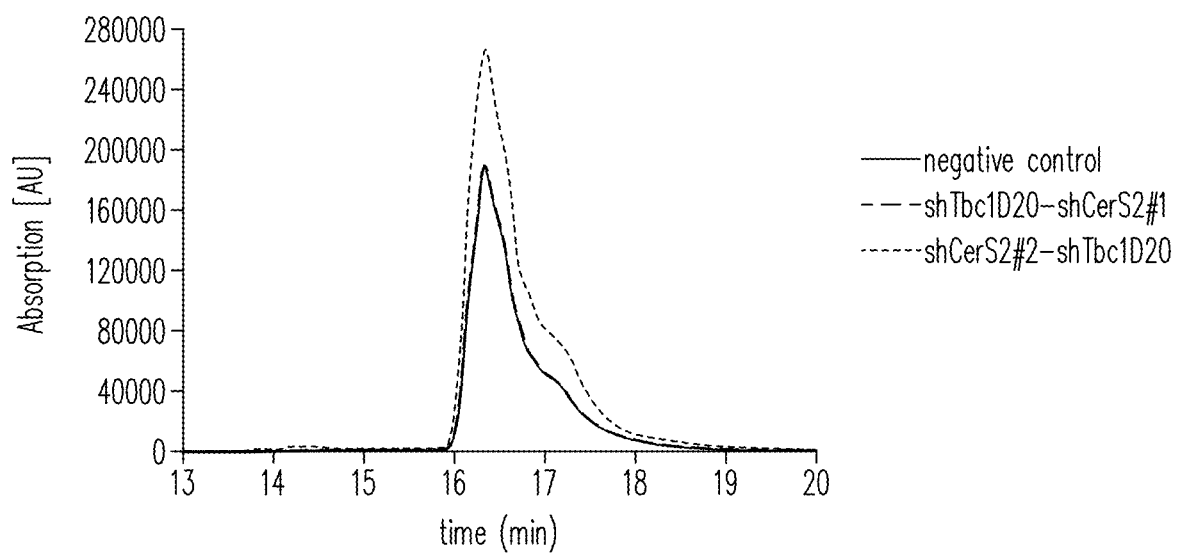

A second pool of cells, stably expressing shTbc1D20-shCerS2#1 (pcDNA6.2-GW/emGFP-shTbc1D20#1-shCerS2#1) and shCerS #2-shTbc1D20 (pcDNA6.2-GW/emGFP-shCerS2#2-shTbc1D20#1) or a negative control sequence were cultivated under fed-batch conditions for 11 days. The secreted antibody was purified from the supernatant and analyzed by HPLC. FIG. 12D shows that the antibody preparations from the different cells (shTbc1D20-shCerS2#1 or shCerS #2-shTbc1D20 expressing cells as well as the negative controls) were very similar, with a proportion of aggregates of less than 1.5%.

Example 13: Expression of Glucose Regulated Protein 78 (GRP78/BiP), CHOP and the ER-Associated Degradation (ERAD) Component HERPUD1 is Increased in ATF6B Knockdown As ATF6 acts as a transcription factor during ER stress, we explored whether ATF6B knockdown resulted in any changes of UPR-related genes. The mRNA level of three bona fide UPR markers—glucose regulated protein 78 (GRP78), homocysteine inducible ER protein with ubiquitin-like domain 1 (Herpud1) and CCAAT-enhancer-binding protein homologous protein (CHOP or DDIT3, NCBI Reference Sequence XM_007648092.1) were analyzed—after treatment with the ER stress inducing reagent Tunicamyin (TM).

Stably transfected cells were produced as described in Example 8. In brief CHO-mAb2 cells were stably transfected with a plasmid encoding a GFP cassette plus a shRNA sequence comprising a nucleotide sequence specifically targeting ATF6B (pcDNA6.2-GW/emGFP-shAtf6b #1 or pcDNA6.2-GW/emGFP-shAtf6b #2) encoding shAtf6b #1 comprising the sequence of SEQ ID NO: 15 (UCCAUCUUCACACUGAGGACC) and shAtf6b #2 comprising the sequence of SEQ ID NO: 37 (UUCACUUCCAGAACCUCCUCU). Cell pools stably expressing the control vector (pcDNA6.2-GW/emGFP-neg. control) served as negative controls. To validate the expression of stably transfected shRNAs, RNA was isolated and qPCR analysis of the ATF6B mRNA level was performed, as described above. Cells transfected with shRNA-encoding plasmids had reduced levels of ATF6B mRNA compared to negative control (FIG. 13A). This again demonstrates that stable genomic integration of plasmid-encoded shRNAs targeting ATF6B leads to decreased expression of the respective target gene in CHO cells.

To investigate whether expression of downstream UPR-related genes are affected CHO-mAb2 cells expressing negative control sequences or shRNAs specific for ATF6B were treated with or without tunicamycin (TM). The mRNA levels of GRP78, Herpud1 and CHOP in untreated cells and TM treated cells were quantified by qPCR (FIG. 13B). Expression of both GRP78 and Herpud1 was significantly enhanced in cells stably transfected with the shRNAs specific for ATF6B compared to cell pools expressing the negative control construct (black bars), whereas CHOP expression was only slightly enhanced. These results indicate that the knockdown of the transcription factor ATF6B triggers the UPR at the transcriptional level.

We further analysed whether expression of downstream UPR-related genes are also affected in a fed-batch culture. The CHO-mAb2 cells stably expressing ATF6B-specific shRNAs or the negative control construct were cultivated in shake flasks with daily feeding. On day 5 mRNA levels of the UPR-related genes GRP78/BiP, CHOP and Herpud1 were analysed. In accordance with the results obtained in seed stock cultures, mRNA levels of the UPR-related genes GRP78/BiP and Herpud1 were elevated in shATF6B expressing cells when compared to control cells (FIG. 13C). Further, shAtf6b #1 and shAtf6b #2 transfected cells showed an increased antibody concentration in the supernatant (1.36-fold) and increased viable cell density at day 7 compared to negative control (data not shown), while the viability was unchanged until day 7 and the glycosylation pattern was unaltered (data not shown).

Example 14: TBC1D20 Knockdown Enhances Rab1 Activity and CERS2 Knockdown Alters the Ceramide Composition in Recombinant CHO Cells TBC1D20 is a GTPase activating protein (GAP) for the small GTPase Rab1. We therefore investigated whether TBC1D20 knockdown in CHO-mAb2 cells results in enhanced levels of active Rab1 using a GST pull down assay.

Cloning of p115-GST Expression Construct

To generate a p115-GST fusion protein, p115 (derived from pEGFP-N2-p115 as described in Brandon et al. 2006; Mol. Biol. Cell., 17(7): 2996-3008) was subcloned into the vector pGex-6P-1 (GE Healthcare) using KpnI with BamHI and SalI with NotI, respectively. The integrity of the construct was verified by Sanger sequencing (GATC Biotech AG).

Protein Expression and Extraction

The p115-GST fusion protein was expressed in *Escherichia coli*, followed by protein extraction. Briefly, transformants were selected in Luria Broth (LB) medium with 100 µg/mL ampicillin and expression was stimulated by adding 0.3 mM Isopropyl-β-D-thiogalactopyranosid (IPTG), when the culture reached an OD600 of 0.8-1.0. Bacteria were harvested by centrifugation and the pellet was frozen on dry ice for 30 minutes. The pellet was resuspended in lysis buffer (50 mM Tris-HCl at pH 7.5, 1 mM EDTA, 1 mM DTT and complete protease inhibitor (Roche)) and 0.1 µg/mL lysozyme was added. After incubation for 30 minutes on ice with gentle shaking, 5 mM MgCl2 and 20 ng/mL DNAse were added for further 30 minutes on ice, followed by centrifugation at 3000 g for 30 minutes. The protein extraction supernatant was then incubated with 1 mL 50% glutathione beads (GE Healthcare) (1 h, 4° C.). Beads were pelleted (5 min at 500 g, 4° C.), washed three times with 4 ml washing buffer (lysis buffer plus 100 mM NaCl), resuspended in 4 mL resuspension buffer (washing buffer without EDTA), pelleted (5 min at 500 g, 4° C.), washed once more and finally resuspended in 0.5 mL of resuspension buffer resulting in 1 mL of a 50% slurry of GST-p115-beads.

GST Pull Down Assay

CHO-IgG cells were transfected with siTbc1D20, siCerS2 and siTbc1D20 in combination or NT control via nucleofection. 72 hours after transfection, 1×10$^6$ cells were lysed in 1 mL homogenization buffer (10 mM HEPES pH 7.4, 150 mM NaCl, 5 mM MgCl$_2$, 1% Triton-X-100, 1 mM DTT, 5% glycerol, phosphatase inhibitor cocktail and complete protease inhibitor cocktail (Roche)) and incubated for 10 minutes on ice. Each lysate was mixed with 25 µL of 50% GST-p115-beads and incubated for 1 hour at 4° C. with gentle shaking. Beads were pelleted and washed three times with homogenization buffer. Beads were resuspended in 20 µL homogenization buffer with 10 µL gel loading buffer, incubated at 95° C. for 5 minutes, vortexed briefly and pelleted. Proteins were separated on a 12% acrylamide gel, transferred to nitrocellulose membranes and detected with an anti-Rab1 antibody (antibodies—online.com). The fusion protein was detected with an anti-GST antibody (GE Healthcare). Aliquots of the cell lysates (input) were also analyzed by immunoblotting using an anti-actin antibody (Sigma-Aldrich) to confirm that equal protein amounts had been subjected to the pulldown assays Three days post transfection active Rab1 was extracted from cell homogenates using the pull-down assay with the p115-GST fusion protein, making use of its binding affinity to the Rab1 effector protein p115 fused to GST. CHO-mAb2 cells transfected with siTbc1D20 alone or in combination with siCerS2 showed enhanced amounts of active Rab1 (FIG. 14 A). Quantification using Image J software confirmed that Rab1 activity was increased 2-fold in cells transfected with siTbc1D20 alone or in combination with siCerS2 (FIG. 14B). Knockdown control (qPCR) at day 2 post transfection revealed a reduction of Tbc1D20 mRNA by 50% in cells transfected with siTbc1D20 alone or in combination with siCerS2 (FIG. 14C). These findings confirm that the knockdown of the Rab1 GAP TBC1D20 amplified Rab1 activity in CHO-mAb2 cells.

We further analysed ceramide composition in cells transfected with siCerS2 alone or in combination with siTbc1D20. Ceramide synthesis at the ER and its subsequent transport to the Golgi complex are essential steps in the secretory pathway. CERS2 is one of the six ceramide synthase isoforms expressed in mammalian cells. Each isoform uses a restricted subset of fatty acyl-CoAs as substrates for the ceramide synthesis. CERS2 preferentially generates very long chain ceramides, particularly C22 and C24-ceramides. Because of its crucial role in the secretory pathway, it is conceivable that an altered ceramide composition of ER membranes could affect sorting and trafficking of cargo proteins.

To investigate whether the ceramide composition is altered in CERS2 knockdown cells, CHO-mAb2 cells were transfected with siCerS2#1 (SEQ ID NO: 8) alone, in combination with Tbc1D20#1 (SEQ ID NO: 7) or with a non-targeting siRNA pool (siRNA NT-control, SEQ ID NOs: 38 to 41) as a control and analysed using a fluorescent ceramide synthase activity assay.

Fluorescent Ceramide Synthase Activity Assay

At day 3 post nucleofection, 1.5×10$^6$ cells were pelleted, resuspended in 1 mL lysis buffer (20 mM HEPES at pH 7.4, 25 mM KCl, 2 mM MgCl$_2$, 250 mM Sucrose and Complete protease inhibitor cocktail (Roche)) and mechanically lysed using a 26 G needle (Terumo). Protein concentration was determined using the bicinchoninic acid (BCA) assay (Bio-Rad). To measure ceramide synthase activity, a fluorescent assay was conducted as described by Kim et al (Kim et al., 2012) with minor modifications. Briefly, 50 µg homogenate protein was incubated in reaction buffer (20 mM Hepes, pH 7.4, 25 mM KCl, 2 mM MgCl$_2$, 0.5 mM DTT, 0.1% (w/v) fatty acid-free BSA, 10 µM NBD-sphinganine, 50 µM fatty acid-CoA and 250 mM Sucrose) with shaking at 35° C. for 30 min (for C16-ceramide quantification) and 120 min (for C24-ceramide quantification). The reactions were stopped with 250 µL chloroform/methanol (2:1), vortexed, centrifuged and the lower phase was transferred to a 5 mL glass tube. The upper aqueous phase was reextracted as described and both organic phases were combined and dried under a steam of nitrogen, followed by resuspension in 100 µL methanol. 2×2 µL of each reaction were applied onto aluminum-backed Silica Gel 60 TLC plates and separated by chromatography (chloroform/methanol/water, 8:1:0.1 v/v/v). Fluorescence of the products was detected using a Typhoon Trio+ Scanner (GE Healthcare). The products C16-dihydroceramide and C24-dihydroceramide were separated by thin layer chromatography and detected using a fluorescence scanner (FIG. 14D). Band intensity of C16- and C24-dihydroceramides was quantified using Image J software (FIG. 14E).

In comparison to the control, the knockdown of CERS2 and the combined knockdown of CERS2 and TBC1D20 resulted in a decreased level of C24-ceramide and an increased amount of C16-ceramide (FIGS. 14D and E). Quantification revealed that the fraction of C24-ceramide was reduced on average by 67.6% after knockdown of CERS2 and 68.8% after combined knockdown of CERS2 and TBC1D20. C16-ceramide was increased by 73.0% in cells transfected with siCerS2 and 19.1% in cells transfected with siCerS2 and siTbc1D20. Since the reduction of C24-ceramide was apparently stronger than the enhancement of C16-ceramide, it is possible that further LC ceramides (for example C14- or C18-ceramide) are additionally affected. The efficiency of siRNA-mediated knockdown was confirmed by qPCR as described above (FIG. 14F). Thus, the knockdown of CERS2 results in an altered ceramide composition with an increased ratio of C16-ceramide to C24-ceramide.

Example 15: Stable Knockdown of CERS2 Alters the Ceramide Composition in Recombinant CHO Cells CHO-mAb2 cells were stably transfected with expression vectors containing shRNA sequences comprising sequences specifically targeting CERS2 and TBC1D20 (pcDNA6.2-GW/emGFP-shTbc1D20#1-shCerS2#1 or pcDNA6.2-GW/emGFP-shCerS2#2-shTbc1D20#1) as described in Example 11. Cells were lysed one day after subcultivation and analysed for ceramide composition using a fluorescent ceramide synthase activity assay as described in Example 14.

The double knockdown of CERS2 and TBC1D20 by both independent shRNA combinations resulted in a strong decrease of C24-ceramide compared to control cells (shTbc1D20#1-shCerS2#1: 51.7%, shCerS2#2-shTbc1D20#1 52.1%). At the same time, the amount of C16-ceramide increased dramatically by 97.7% (shTbc1D20#1-shCerS2#1) and 74.5% (shCerS2#2-shTbc1D20#1), confirming the results obtained in the transient experiment (FIGS. 14D and E).

Example 16: CRISPR/Cas9-Mediated Knockout of ATF6B in CHO-mAb2 Cells

So far, we could show that transient and stable knockdown of ATF6B in CHO-mAb2 cells enhanced antibody secretion in comparison to non-transfected cells or cells transfected with a negative control plasmid. To investigate whether the total depletion of ATF6B protein could further improve productivity, knockout cells are generated by mutating the ATF6B gene to attain a premature stop of transcription and thus prevent ATF6B protein formation. Applying the CRISPR/Cas9 system, three independent gRNA sequences targeting the ATF6B gene to generate CHO cell clones stably depleted of ATF6B are used. Target sites are selected by identifying protospacer adjacent motifs (PAM) in the first two exons present in both ATF6B transcript variants. Three guide RNAs are designed that each have 20 complementary nucleotides to the sequence upstream of the PAM sites. Each gRNA is cloned into the GeneArt® CRISPR Nuclease Vector with OFP Reporter (Life Technologies). The vector contains a CMV promoter driven expression cassette for a Caspase 9 type 2 nuclease and an OFP gene and a further expression cassette for the guide RNA that is driven by a U6 polII type promoter. The vector is amplified in competent *E. coli* and purified as described before. CHO-mAb2 cells are transfected one day after subcultivation via nucleofection with the Cell Line Nucleofector Kit V (Lonza) as described before. Cleavage efficiency is detected using the GeneART® Genomic Cleavage Detection Kit (Life Technologies) according to the manufacturer's instructions. To generate stable cell clones CHO-mAb2 cells are transfected with the described gRNA and Cas9 containing vector and, additionally, a single-stranded CMV promoter driven puromycin or alternatively a fluorescence marker gene. This selection marker gene is embedded in flanking regions complementary to genomic regions flanking the target site of interest. Only cells in which the genomic ATF6B target site is cleaved by the Cas9 nuclease followed by integration of the selection marker gene by homology directed repair (HDR) bear the resistance or fluorescence marker, respectively. Single cell clones are generated by FACS sorting for OFP positive cells and subsequent cultivation in medium (Boehringer Ingelheim). Efficient depletion of ATF6B protein is controlled, e.g., by PCR or by Western blotting using a specific anti-ATF6B antibody and efficient mutation in the ATF6B gene is analyzed by sequencing the genomic loci of interest.

Example 17: CRISPR/Cas9-Mediated Knockout of CERS2 and TBC1D20 in Combination in CHO-mAb2 Cells We could show before that transient and stable knockdown of CERS2 and TBC1D20 in CHO-mAb2 cells enhanced antibody secretion in comparison to non-transfected cells or cells transfected with a negative control plasmid. To investigate whether the total depletion of both CERS2 and TBC1D20 proteins could further improve productivity, knockout cell lines are generated by mutating the CERS2 and TBC1D20 genes to attain a premature stop of transcription and thus prevent CERS2 and TBC1D20 protein formation. Applying the CRISPR/Cas9 technology three independent gRNAs targeting CERS2 and three independent gRNAs targeting TBC1D20 are used to mutate the respective genes. Target sites are selected by identifying protospacer adjacent motifs (PAM) in the first two exons present in all six CERS2 transcript variants or two TBC1D20 transcript variants, respectively. Three guide RNAs are designed for each gene that have 20 complementary nucleotides to the sequence upstream of the PAM sites. Each gRNA is cloned into the GeneArt® CRISPR Nuclease Vector with OFP Reporter (Life Technologies) as described above. CHO-mAb2 cells are transfected as described before and cleavage efficiency is detected using the GeneART® Genomic Cleavage Detection Kit (Life Technologies) according to the manufacturer's instructions. To generate stable cell clones CHO-mAb2 cells are transfected with the described gRNA and Cas9 containing vector and, additionally, a single-stranded CMV promoter driven puromycin or alternatively a fluorescence marker gene. This selection marker gene is embedded in flanking regions complementary to genomic regions flanking the target site of interest. Only cells in which the genomic CERS2 or TBC1D20 target site is cleaved by the Cas9 nuclease followed by integration of the selection marker gene by homology directed repair (HDR) bear the resistance or fluorescence marker, respectively. Single cell clones are generated by FACS sorting for OFP positive cells and subsequent cultivation in medium (Boehringer Ingelheim). Efficient depletion of CERS2 or TBC1D20 protein is controlled, e.g., by PCR or by Western blotting using a specific anti-CERS2 antibody or anti-TBC1D20 antibody, respectively, and efficient mutation in the genome is analyzed by sequencing the genomic loci of interest.

The invention is encompassed by the following items:

1. A mammalian cell having enhanced secretion of a recombinant therapeutic protein comprising
    (a) reduced expression of the host cell proteins TBC1 domain family member 20 (TBC1D20) and ceramide synthase 2 (CERS2); or
    (b) reduced expression of the host cell protein activating transcription factor 6 beta (ATF6B), wherein the mammalian cell further comprises one or more expression cassette(s) encoding a recombinant secreted therapeutic protein.

2. The mammalian cell of item 1, having reduced ATF6B protein expression and further comprising one or more expression cassette(s) encoding a recombinant secreted therapeutic protein.

3. The mammalian cell of items 1 or 2, wherein the expression of the host cell proteins TBC1D20 and CERS2, or of the host cell protein ATF6B, is reduced by at least 30%, at least 40%, at least 50%, at least 75%, or 100%, compared to a control mammalian cell.

4. The mammalian cell of any one of items 1 to 3, wherein the secretion of the recombinant therapeutic protein is enhanced by at least 10%, at least 20%, at least 30%, at least 40%, at least 50%, at least 75%, at least 100% or at least 200%, compared to a control mammalian cell.

5. The mammalian cell of any one of the preceding items, wherein:
    (a) the gene encoding the host cell protein comprises a genetic modification that inhibits expression of said host cell protein, or
    (b) the mammalian cell comprises a RNA oligonucleotide that inhibits expression of the gene encoding said host cell protein by RNA-interference, and
    wherein the protein expression of TBC1D20 and CERS2 or the protein expression of ATF6B in the mammalian cell is reduced compared to the same mammalian cell not containing said genetic modification(s) or RNA oligonucleotide(s).

6. The mammalian cell of item 5, wherein the RNA-interference is mediated by small hairpin RNA (shRNA) or short interfering RNA (siRNA).

7. The mammalian cell of item 6, wherein the mammalian cell has been transfected with one or more expression vector(s) comprising a nucleotide sequence encoding said siRNA(s) or shRNA(s).

8. The mammalian cell of item 7, wherein the mammalian cell is stably transfected with one or more expression vector(s) comprising a nucleotide sequence encoding said siRNA(s) or shRNA(s).

9. The mammalian cell of any one of items 6 to 8, wherein the siRNA is
    (a) siTbc1D20#1 (SEQ ID NO: 7) or siCerS2#1 (SEQ ID NO: 8), or a combination thereof; or
    (b) one or more of siAtf6b #1 (SEQ ID NO: 9), siAtf6b #2 (SEQ ID NO: 10), and siAtf6b #3 (SEQ ID NO: 11).

10. The mammalian cell of any one of items 6 to 8, wherein the shRNA comprises
    (a) shTbc1D20#1 (SEQ ID NO: 12) or one or more of shCerS2#1 (SEQ ID NO: 13) and shCerS2#2 (SEQ ID NO: 14), or a combination thereof; or
    (b) one or more of shAtf6b #1 (SEQ ID NO: 15) and shAtf6b #2 (SEQ ID NO: 37), preferably shAtf6b #1 (SEQ ID NO: 15).

11. The mammalian cell of item 5, wherein the genetic modification in the gene(s) encoding the host cell protein(s) TBC1D20, CERS2 or ATF6B is independently
    (a) a gene deletion; or
    (b) a mutation in the gene that inhibits expression of the host cell protein.

12. The mammalian cell of item 11, wherein the mutation is a deletion, addition or substitution.

13. The mammalian cell of item 12, wherein:
    (a) the mutation is in the coding region of the gene; and/or
    (b) the mutation is in the promoter or a regulatory region of the gene.

14. The mammalian cell of any one of the preceding items, wherein:
    (a) the host cell protein TBC1D20 has sequence identity of at least 80% to the amino acid sequence of SEQ ID NO: 4 and the host cell protein CERS2 has sequence identity of at least 80% to the amino acid sequence of SEQ ID NO: 5; or
    (b) the host cell protein ATF6B has sequence identity of at least 80% to the amino acid sequence of SEQ ID NO: 6.

15. The mammalian cell of item 14, wherein
    (a) the host cell protein TBC1D20 has the amino acid sequence of SEQ ID NO: 4 and the host cell protein CERS2 has the amino acid sequence of SEQ ID NO: 5; or
    (b) the host cell protein ATF6B has the amino acid sequence of SEQ ID NO: 6.

16. A mammalian cell having enhanced secretion of a recombinant therapeutic protein comprising reduced expression of the host cell proteins TBC1D20 and CERS2.

17. The mammalian cell of item 16, further comprising one or more expression cassette(s) encoding a recombinant secreted therapeutic protein.

18. The mammalian cell of items 17, wherein the secretion of the recombinant therapeutic protein is enhanced by at least 10%, at least 20%, at least 30%, at least 40%, at least 50%, at least 75%, at least 100% or at least 200%, compared to a control mammalian cell.

19. The mammalian cell of items 16 to 18, wherein the expression of the host cell proteins TBC1D20 and CERS2 is reduced by at least 30%, at least 40%, at least 50%, at least 75%, or 100%, compared to a control mammalian cell.

20. The mammalian cell of any one of items 16 to 19, wherein:
    (a) the gene encoding the host cell protein comprises a genetic modification that inhibits expression of said host cell protein, or
    (b) the mammalian cell comprises a RNA oligonucleotide that inhibits expression of the gene encoding said host cell protein by RNA-interference, and
    wherein the protein expression of TBC1D20 and CERS2 in the mammalian cell is reduced compared to the same mammalian cell not containing said genetic modifications or RNA oligonucleotides.

21. The mammalian cell of item 20, wherein the RNA-interference is mediated by small hairpin RNA (shRNA) or short interfering RNA (siRNA).

22. The mammalian cell of item 21, wherein the mammalian cell has been transfected with one or more expression vector(s) comprising a nucleotide sequence encoding said siRNA(s) or shRNA(s).

23. The mammalian cell of item 22, wherein the mammalian cell has been stably transfected with one or more expression vector(s) comprising a nucleotide sequence encoding said siRNA(s) or shRNA(s).

24. The mammalian cell of any one of items 21 to 23, wherein the siRNA is siTbc1D20#1 (SEQ ID NO: 7) or siCerS2#1 (SEQ ID NO: 8), or a combination thereof.

25. The mammalian cell of any one of items 21 to 23, wherein the shRNA comprises shTbc1D20#1 (SEQ ID NO: 12) or one or more of shCerS2#1 (SEQ ID NO: 13) and shCerS2#2 (SEQ ID NO: 14), or a combination thereof.

26. The mammalian cell of item 20, wherein the genetic modification in the genes encoding the host cell proteins TBC1D20 and CERS2 is independently
   (a) a gene deletion; or
   (b) a mutation in the gene that inhibits expression of the host cell protein.

27. The mammalian cell of item 26, wherein the mutation is a deletion, addition or substitution.

28. The mammalian cell of item 27, wherein
   (a) the mutation is in the coding region of the gene; and/or
   (b) the mutation is in the promoter or a regulatory region of the gene.

29. The mammalian cell of any one of items 16 to 28, wherein the host cell protein TBC1D20 has sequence identity of at least 80% to the amino acid sequence of SEQ ID NO: 4 and the host cell protein CERS2 has sequence identity of at least 80% to the amino acid sequence of SEQ ID NO: 5.

30. The mammalian cell of any one of items 16 to 29, wherein the host cell protein TBC1D20 has the amino acid sequence of SEQ ID NO: 4 and the host cell protein CERS2 has the amino acid sequence of SEQ ID NO: 5.

31. The mammalian cell of any one of the preceding items, wherein the said recombinant secreted therapeutic protein is
   (a) an antibody, preferably a monoclonal antibody, a bi-specific antibody or a fragment thereof, or
   (b) an Fc-fusion protein.

32. The mammalian cell of any one of the preceding items, wherein the cell is a rodent or a human cell.

33. The mammalian cell of item 32, wherein the rodent cell is a hamster cell.

34. The mammalian cell of item 33, wherein the hamster cell is a CHO cell, preferably a CHO-DG44 cell, a CHO-K1 cell or a glutamine synthetase (GS)-deficient derivative thereof.

35. A method of producing a mammalian cell with enhanced secretion of a recombinant therapeutic protein comprising
   (a) reducing expression of the host cell proteins TBC1D20 and CERS2, or of the host cell protein ATF6B in the mammalian cell by introducing
      (i) a genetic modification into a gene encoding the host cell protein that inhibits expression of said host cell protein, or
      (ii) a RNA oligonucleotide into the mammalian cell that inhibits expression of the gene encoding said host cell protein by RNA-interference, and
   (b) introducing one or more gene(s) encoding a recombinant secreted therapeutic protein.

36. The method of item 35, further comprising the following steps:
   (c) selecting cells with enhanced secretion of the recombinant therapeutic protein; and
   (d) optionally culturing the cells obtained in step (c) under conditions which allow expression of one or more gene(s) encoding a recombinant secreted therapeutic protein.

37. The method of items 35 or 36, wherein the protein expression of TBC1D20 and CERS2 or the protein expression of ATF6B in the mammalian cell is reduced compared to the same mammalian cell not containing said genetic modification(s) or RNA oligonucleotide(s).

38. The method of any one of items 35 or 37, comprising reducing TBC1D20 and CERS2 protein expression in the mammalian cell.

39. The method of any one of items 35 or 37, comprising reducing ATF6B protein expression in the mammalian cell.

40. The method of any one of items 35 to 39, wherein the RNA-interference is mediated by small hairpin RNA (shRNA) or short interfering RNA (siRNA).

41. The method of item 40, comprising transfecting the mammalian cell with one or more expression vector(s) comprising a nucleotide sequence encoding said siRNA(s) or shRNA(s).

42. The method of item 41, wherein the mammalian cell is stably transfected with one or more expression vector(s) comprising a nucleotide sequence encoding said siRNA(s) or shRNA(s).

43. The method of any one of items 40 to 42, wherein the siRNA is
   (a) siTbc1D20#1 (SEQ ID NO: 7) or siCerS2#1 (SEQ ID NO: 8), or a combination thereof; or
   (b) one or more of siAtf6b #1 (SEQ ID NO: 9), siAtf6b #2 (SEQ ID NO: 10), and siAtf6b #3 (SEQ ID NO: 11).

44. The method of any one of items 40 to 42, wherein the shRNA comprises
   (a) shTbc1D20#1 (SEQ ID NO: 12) or one or more of shCerS2#1 (SEQ ID NO: 13) and shCerS2#2 (SEQ ID NO: 14), or a combination thereof; or
   (b) one or more of shAtf6b #1 (SEQ ID NO: 15) and shAtf6b #2 (SEQ ID NO: 37), preferably shAtf6b #1 (SEQ ID NO: 15).

45. The method of item 35, wherein the genetic modification in the gene(s) encoding the host cell protein(s) TBC1D20 and CERS2, or ATF6B is independently
   (a) a gene deletion; or
   (b) a mutation in the gene that inhibits expression of the host cell protein.

46. The method of item 45, wherein the mutation is a deletion, addition or substitution.

47. The method of item 46, wherein:
   (a) the mutation is in the coding region of the gene; and/or
   (b) the mutation is in the promoter or a regulatory region of the gene.

48. The method of any one of items 35 to 47, wherein:
   (a) the host cell protein TBC1D20 has sequence identity of at least 80% to the amino acid sequence of SEQ ID NO: 4 and the host cell protein CERS2 has sequence identity of at least 80% to the amino acid sequence of SEQ ID NO: 5; or
   (b) the host cell protein ATF6B has sequence identity of at least 80% to the amino acid sequence of SEQ ID NO: 6.

49. The method of any one of items 35 to 48, wherein
(a) the host cell protein TBC1D20 has the amino acid sequence of SEQ ID NO: 4 and the host cell protein CERS2 has the amino acid sequence of SEQ ID NO: 5; or
(b) the host cell protein ATF6B has the amino acid sequence of SEQ ID NO: 6.

50. The method of any one of items 35 to 49, wherein the said recombinant secreted therapeutic protein is
(a) an antibody, preferably a monoclonal antibody, a bi-specific antibody or a fragment thereof, or
(b) an Fc-fusion protein.

51. The method of any one of items 35 to 50, wherein the cell is a rodent or a human cell.

52. The method of item 51, wherein the rodent cell is a hamster cell.

53. The method of item 52, wherein the hamster cell is a CHO cell, preferably a CHO-DG44 cell, a CHO-K1 cell or a glutamine synthetase (GS)-deficient derivative thereof.

54. The method of any one of items 35 to 53, wherein step (a) may be performed before or after step (b).

55. The method of any one of items 35 to 54, wherein the selection step of step (c) is performed in the presence of a selection agent.

56. The method of any one of items 35 to 55, further comprising an amplification step (b'), comprising amplifying the one or more gene(s) introduced in step (b) together with an amplifiable selectable marker gene and culturing the mammalian cell in the presence of an agent which allows the amplification of the amplifiable selectable marker gene.

57. The method of items 56, wherein the amplifiable selectable marker gene encodes the amplifiable selectable markers dihydrofolate reductase or glutamine synthetase.

58. The method of any one of items 35 to 57, wherein the expression of the host cell proteins TBC1D20 and CERS2 or of the host cell protein ATF6B is reduced by at least 30%, at least 40%, at least 50%, at least 75%, or 100% compared to a mammalian cell produced by the method of any one of items 35 to 56 using the same starting material, but omitting step (a).

59. The method of any one of items 35 to 58, wherein the secretion of the recombinant therapeutic protein is enhanced by at least 10%, at least 20%, at least 30%, at least 40%, at least 50%, at least 75%, at least 100% or at least 200% compared to a mammalian cell produced by the method of any one of items 35 to 58 using the same starting material, but omitting step (a).

60. A method for the production of a recombinant secreted therapeutic protein in a mammalian cell comprising
(a) providing the mammalian cell of any one of items 1 to 34 wherein the cell is transfected with a recombinant secreted therapeutic protein or providing the mammalian cell produced by the method of any one of the items 35 to 59,
(b) culturing the mammalian cell of step (a) in a cell culture medium at conditions allowing production of the recombinant secreted therapeutic protein,
(c) harvesting the recombinant secreted therapeutic protein, and optionally
(d) purifying the recombinant secreted therapeutic protein.

61. Use of the mammalian cell of any one of items 1 to 34 or the mammalian cell produced by the method of items 35 to 59 for increasing the yield of a recombinant secreted therapeutic protein.

62. The use of item 61, wherein the recombinant secreted therapeutic protein is (a) an antibody, preferably a monoclonal antibody, a bi-specific antibody or a fragment thereof, or
(b) an Fc-fusion protein.

SEQUENCE TABLE

SEQ ID NO 1: Tbc1D20 Chinese Hamster cDNA
SEQ ID NO 2: CerS2 Chinese Hamster cDNA
SEQ ID NO 3: Atf6b Chinese Hamster cDNA
SEQ ID NO 4: TBC1D20 Chinese Hamster protein
SEQ ID NO 5: CERS2 Chinese Hamster protein
SEQ ID NO 6: ATF6B Chinese Hamster protein
SEQ ID NO 7: siTbc1D20#1
SEQ ID NO 8: siCerS2#1
SEQ ID NO 9: siAtf6b #1
SEQ ID NO 10: siAtf6b #2
SEQ ID NO 11: siAtf6b #3
SEQ ID NO 12: shTbc1D20#1
SEQ ID NO 13: shCerS2#1
SEQ ID NO 14: shCerS2#2
SEQ ID NO 15: shAtf6b #1
SEQ ID NO 16: shTbc1D20#1_oligonucleotide_forward
SEQ ID NO 17: shTbc1D20#1_oligonucleotide_reverse
SEQ ID NO 18: shCerS2#1_oligonucleotide_forward
SEQ ID NO 19: shCerS2#1_oligonucleotide_reverse
SEQ ID NO 20: shCerS2#2_oligonucleotide_forward
SEQ ID NO 21: shCerS2#2_oligonucleotide_reverse
SEQ ID NO 22: shAtf6b #1_oligonucleotide_forward
SEQ ID NO 23: shAtf6b #1_oligonucleotide_reverse
SEQ ID NO 24: mAb1 IgG1 heavy chain
SEQ ID NO 25: mAb1 IgG1 light chain
SEQ ID NO 26: mAb2 IgG1 heavy chain
SEQ ID NO 27: mAb2 IgG1 light chain
SEQ ID NO 28: hsa-miR-1287_oligonucleotide_forward
SEQ ID NO 29: hsa-miR-1287_oligonucleotide_reverse
SEQ ID NO 30: hsa-miR-1978_oligonucleotide_forward
SEQ ID NO 31: hsa-miR-1978_oligonucleotide_reverse
SEQ ID NO 32: hsa-miR-1287
SEQ ID NO 33: hsa-miR-1978
SEQ ID NO:34: negative control
SEQ ID NO 35: shAtf6b #2_oligonucleotide_forward
SEQ ID NO 36: shAtf6b #2_oligonucleotide_reverse
SEQ ID NO 37: shAtf6b #2
SEQ ID NO 38: siRNA NT-control #1
SEQ ID NO 39: siRNA NT-control #2
SEQ ID NO 40: siRNA NT-control #3
SEQ ID NO 41: siRNA NT-control #4
SEQ ID NO 42: qPCR primer (Atf6b) forward
SEQ ID NO 43: qPCR primer (Atf6b) reverse
SEQ ID NO 44: qPCR primer (Tbc1D20) forward
SEQ ID NO 45: qPCR primer (Tbc1D20) reverse
SEQ ID NO 46: qPCR primer (CerS2) forward
SEQ ID NO 47: qPCR primer (CerS2) reverse
SEQ ID NO 48: qPCR primer (CHOP) forward
SEQ ID NO 49: qPCR primer (CHOP) reverse
SEQ ID NO 50: qPCR primer (GRP78) forward
SEQ ID NO 51: qPCR primer (GRP78) reverse
SEQ ID NO 52: qPCR primer (Herpud1) forward
SEQ ID NO 53: qPCR primer (Herpud1) reverse

The invention claimed is:

1. A Chinese Hamster Ovary (CHO) cell engineered to have enhanced secretion of a recombinant therapeutic protein compared to a non-engineered CHO cell comprising
reduced expression of the host cell proteins TBC1 domain family member 20 (TBC1D20) and ceramide synthase 2 (CERS2);
wherein the engineered CHO cell further comprises one or more expression cassette(s) encoding a recombinant secreted therapeutic protein.

2. The engineered CHO cell of claim 1, further comprising one or more expression cassette(s) encoding a recombinant secreted therapeutic protein.

3. The engineered CHO cell of claim 1, wherein:
(a) the gene encoding the host cell protein comprises a genetic modification that inhibits expression of said host cell protein, or
(b) the CHO cell comprises a RNA oligonucleotide that inhibits expression of the gene encoding said host cell protein by RNA-interference, and
wherein the protein expression of TBC1D20 and CERS2 in the CHO cell is reduced compared to the same CHO cell not containing said genetic modification(s) or RNA oligonucleotide(s).

4. The engineered CHO cell of claim 3, wherein the genetic modification in the gene(s) encoding the host cell protein(s) TBC1D20 and CERS2 is independently
(a) a gene deletion; or
(b) a mutation in the gene that inhibits expression of the host cell protein, wherein said mutation is in the coding region of the gene and/or the promoter or regulatory region of the gene.

5. The engineered CHO cell of claim 1, wherein:
(a) the host cell protein TBC1D20 has sequence identity of at least 80% to the amino acid sequence of SEQ ID NO: 4 and the host cell protein CERS2 has sequence identity of at least 80% to the amino acid sequence of SEQ ID NO: 5.

6. The engineered CHO cell of claim 1, wherein the said recombinant secreted therapeutic protein is
(a) an antibody, a monoclonal antibody, a bi-specific antibody or a fragment thereof, or
(b) an Fc-fusion protein.

* * * * *